(12) United States Patent
Okura

(10) Patent No.: US 10,781,478 B2
(45) Date of Patent: *Sep. 22, 2020

(54) SYSTEMS, METHODS, AND COMPOSITIONS FOR ENHANCING THE SPECIFICITY OF NUCLEIC ACID HYBRIDIZATION

(71) Applicant: Patricia Okura, Seattle, CA (US)

(72) Inventor: Michael D. Okura, Honolulu, HI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/277,920

(22) Filed: Feb. 15, 2019

(65) Prior Publication Data

US 2019/0241937 A1 Aug. 8, 2019

Related U.S. Application Data

(63) Continuation of application No. 15/376,555, filed on Dec. 12, 2016, now Pat. No. 10,208,334, and a
(Continued)

(51) Int. Cl.
*C12Q 1/6832* (2018.01)
*C12Q 1/6837* (2018.01)
(Continued)

(52) U.S. Cl.
CPC ........ *C12Q 1/6832* (2013.01); *C12Q 1/6827* (2013.01); *C12Q 1/6837* (2013.01);
(Continued)

(58) Field of Classification Search
None
See application file for complete search history.

(56) References Cited

U.S. PATENT DOCUMENTS 6,150,103 A 11/2000 Ness
7,166,451 B1 1/2007 Yang
(Continued)

FOREIGN PATENT DOCUMENTS

WO WO 03/006675 A2 1/2003
WO WO 2012/142346 A1 10/2012

OTHER PUBLICATIONS

Spink et al, J. Am. Chem. Soc., vol. 119, pp. 10920-10928 (1997).
(Continued)

*Primary Examiner* — Robert T. Crow
(74) *Attorney, Agent, or Firm* — Intellectual Property Law Group LLP

(57) ABSTRACT

Systems, methods and compositions of matter according to the present invention, can be used in capture/enrichment, gene expression profiling and targeted sequencing. Provided are systems, methods and compositions concerning the enhancement of nucleic acid hybridization specificity and controlling the shapes of melting curves revealed by nucleic acid hybrid pairs to optimize nucleic acid analysis. These systems, methods and compositions comprise producing a positively charged surface or surface coating, on the surface of microarray slides or other types of surfaces similarly purposed, which enhances melting curve analysis to the point of allowing detection or differentiation of small changes in sequences between nucleic acid binding partners. The accuracy or resolution of melting curve analysis was to be sufficient to distinguish between the melting of perfect matched dsDNA and dsDNA with the smallest possible change in sequence, a one base pair mismatch.

18 Claims, 28 Drawing Sheets

Specification includes a Sequence Listing.

"How is a Positively Charged Microarray Surface Enhancing DNA Melting"

Related U.S. Application Data continuation-in-part of application No. 13/445,873, filed on Apr. 12, 2012, now Pat. No. 9,856,523.

(60) Provisional application No. 62/266,143, filed on Dec. 11, 2015, provisional application No. 61/474,727, filed on Apr. 12, 2011.

(51) Int. Cl.
*C12Q 1/6827* (2018.01)
*C12Q 1/6848* (2018.01)
*C12Q 1/6886* (2018.01)

(52) U.S. Cl.
CPC ......... *C12Q 1/6848* (2013.01); *C12Q 1/6886* (2013.01); *C12Q 2527/107* (2013.01); *C12Q 2600/156* (2013.01)

(56) References Cited

U.S. PATENT DOCUMENTS

| | | | |
|---|---|---|---|
| 9,103,785 B2* | 8/2015 | Okura | B01L 7/00 |
| 9,856,523 B2* | 1/2018 | Okura | C12Q 1/6837 |
| 10,208,334 B2* | 2/2019 | Okura | C12Q 1/6832 |
| 2002/0090614 A1 | 7/2002 | Zhang | |
| 2005/0042638 A1 | 2/2005 | Arnold | |
| 2007/0031870 A1* | 2/2007 | Newhouse | C12Q 1/6816 435/6.12 |
| 2009/0182120 A1 | 7/2009 | Utermohlen | |

OTHER PUBLICATIONS

Simi et al, Am J. Clin. Pathol., vol. 130, pp. 247-253 (2008).
European Search Report, dated Mar. 29, 2019, for corresponding European Application No. 16 87 4070.
Arnold Vainrub et al., "Surface Electrostatic Effects in Oligonucleotide Microarrays: Control and Optimization of Binding Thermodynamics", Biopolymers, Feb. 2003, vol. 68, pp. 265-270.

* cited by examiner

Real-Time Assembly Installed in Axon 4000a

Types of Melting Curves on Epoxide Coated Slides

Graph A: Combined data from multiple probe spots on chip treated with 5% polyethyleneimine Graph B: Analysis of individual probe spot from graph A.

FIG. 7
DNA Melting Curve Analysis
Two Types
1. Liquid Phase: In solution
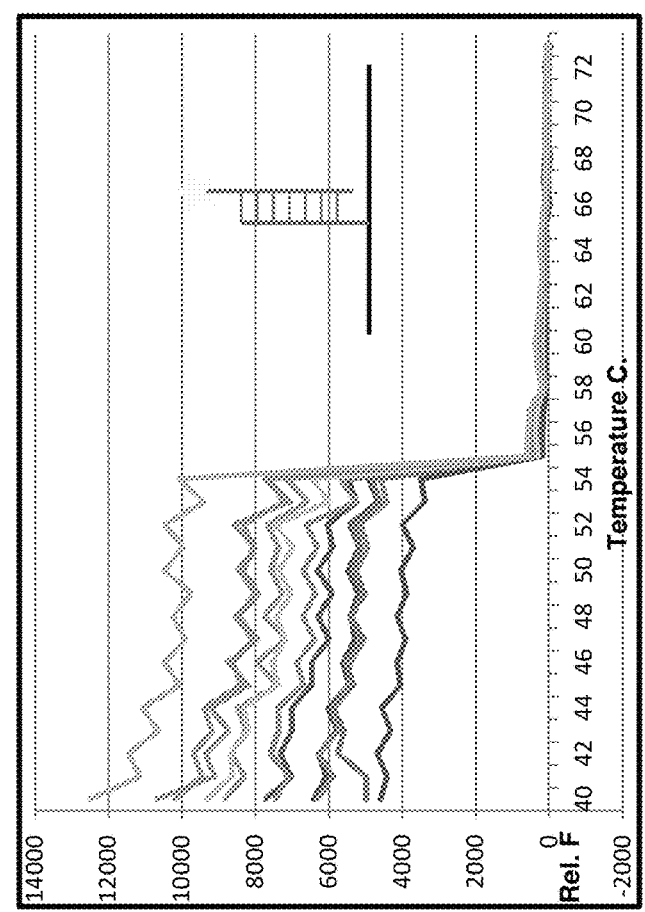
2. Solid Phase: On a solid surface
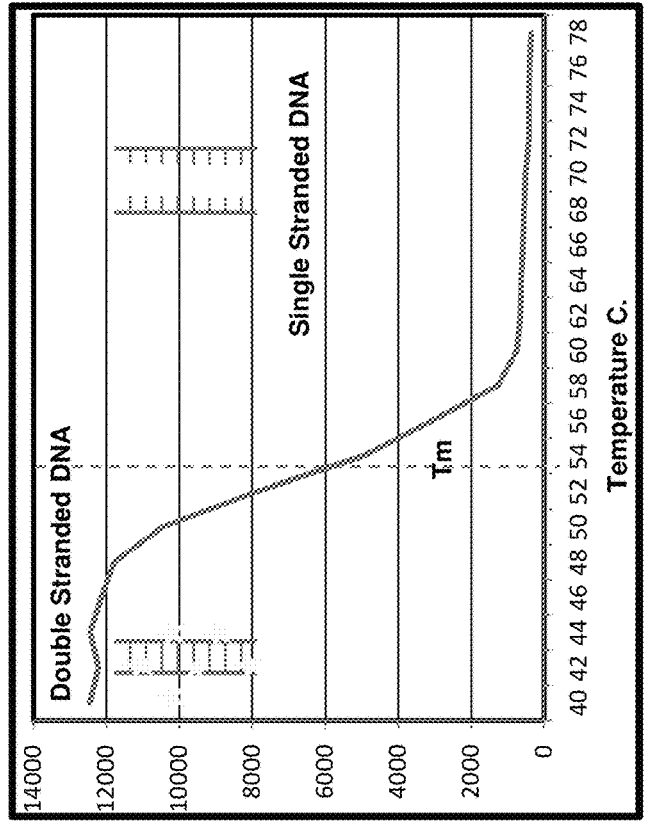

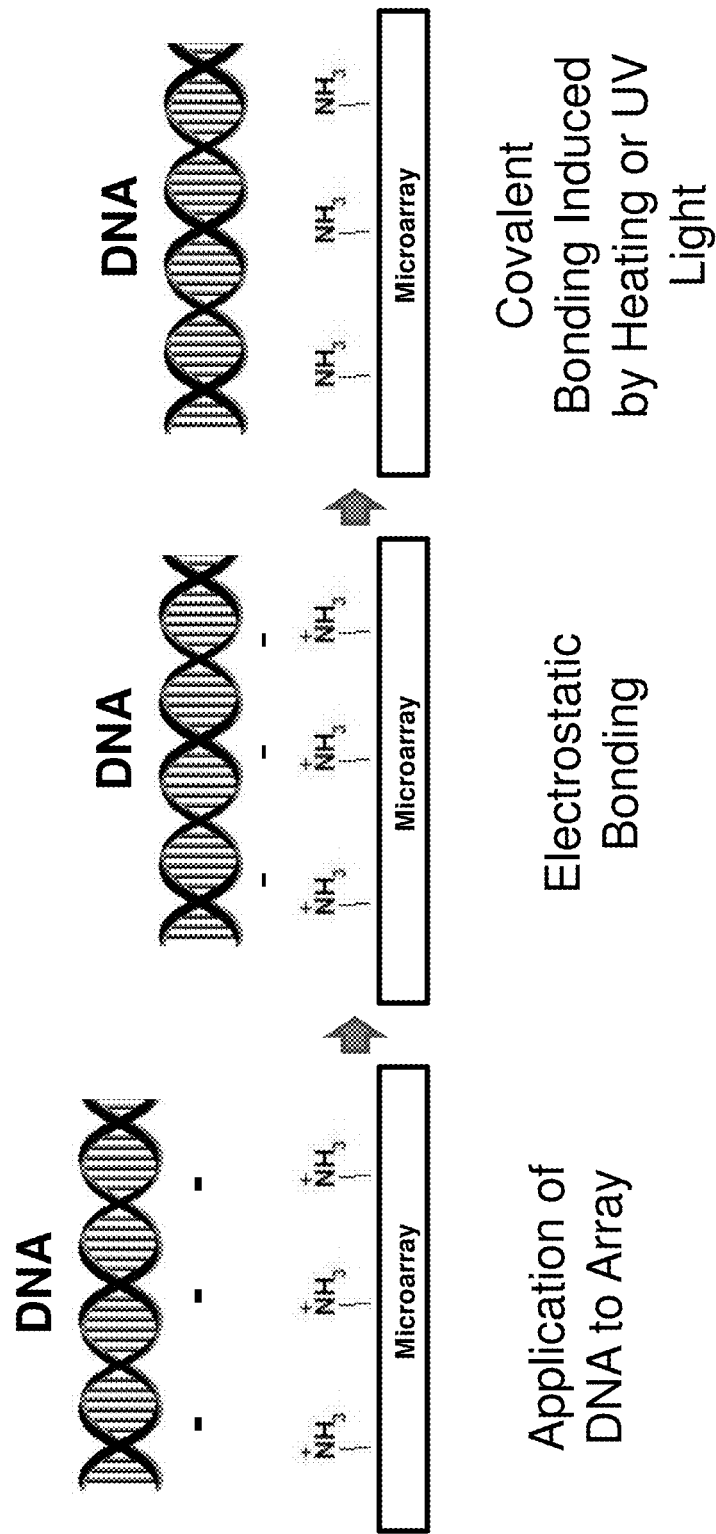

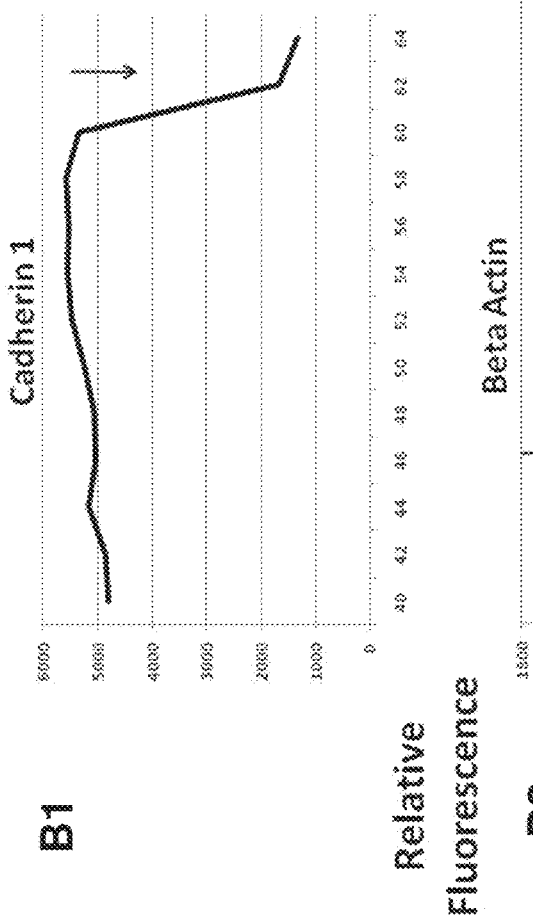
FIG. 11B
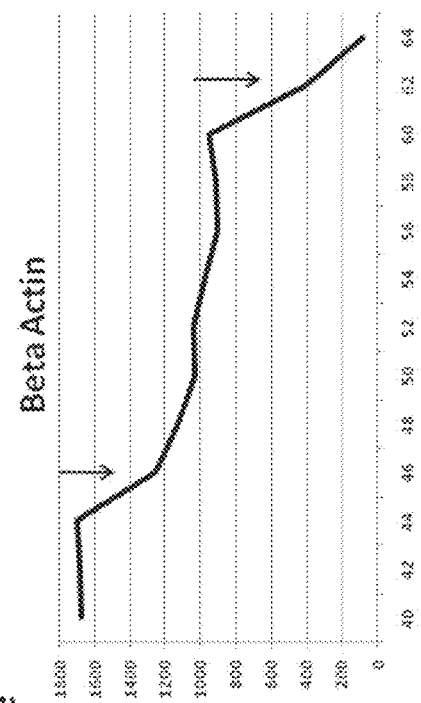
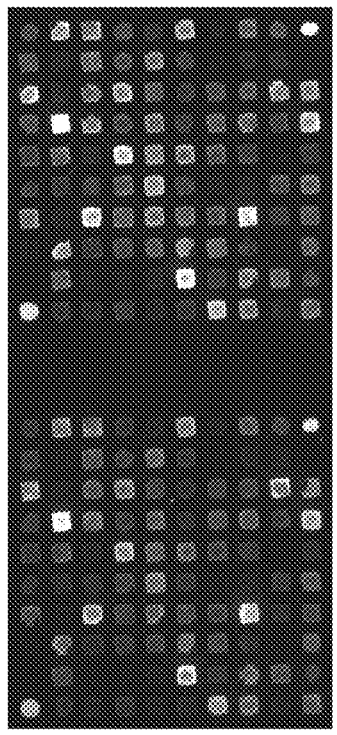
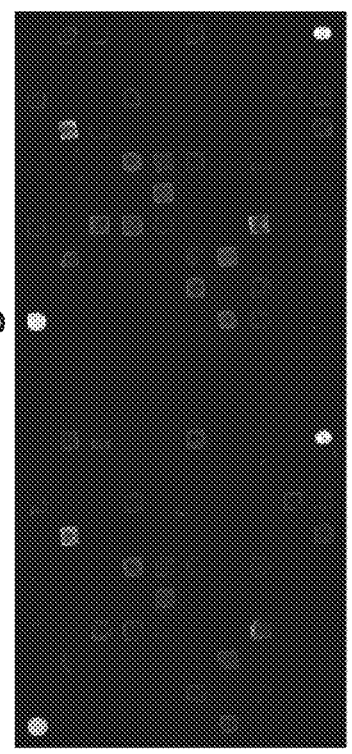
FIG. 11A

FIG. 13
Epoxy Surface Attachment Chemistry
(NEXTERION® Slide E Epoxysilane Coating)
1) Surface Attachment
2) Blocking or Deactivation of the surface with Ethanolamine
Linker:
- Amino Modifier C6 (IDT)
Probe Sequence:
- Mouse GAPDH Gene 25bp
- 5'-TAT GAC AAC TCA CTC AAG ATT GTC A -3'
- GC Content: 36%
- Melt Temp: 67.8°C (buffer w/ 0.375M NaCl)
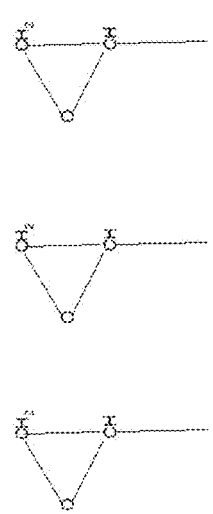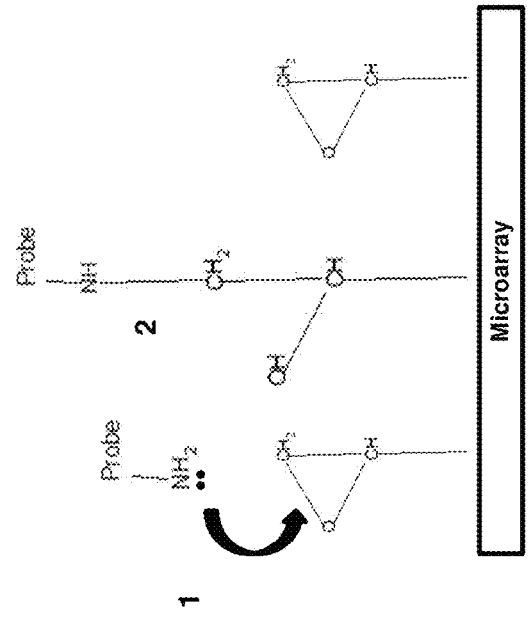

Epoxy Silane Attachment to Glass Microarray and the Formation of a Dipole Moment Results Comparison on Unblocked Epoxy Slides Before and After One Month

FIG. 19

"How is a Positively Charged Microarray Surface Enhancing DNA Melting"

A  Uncharged Surface

B  Confirmation of DNA near Positively Charged Surface

Common Conditions
• Temp Increase Rate
• Flow
• Buffer Composition

Modulated by ionic strength of the buffer

Attractive Electrostatic Forces

Surface Bound

Linker Bound

Only H-Bonding Holding Target DNA in Place

H-Bonding and Surface Electrostatic Forces Acting on Target DNA

FIG. 20
Potential for Diagnostic Applications in Oncology
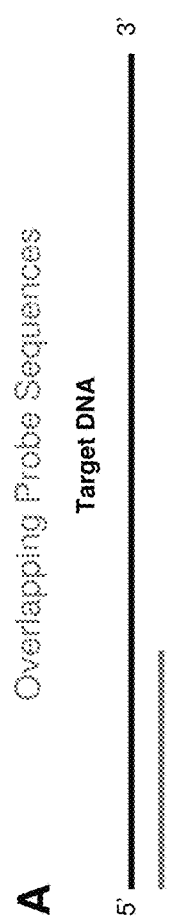
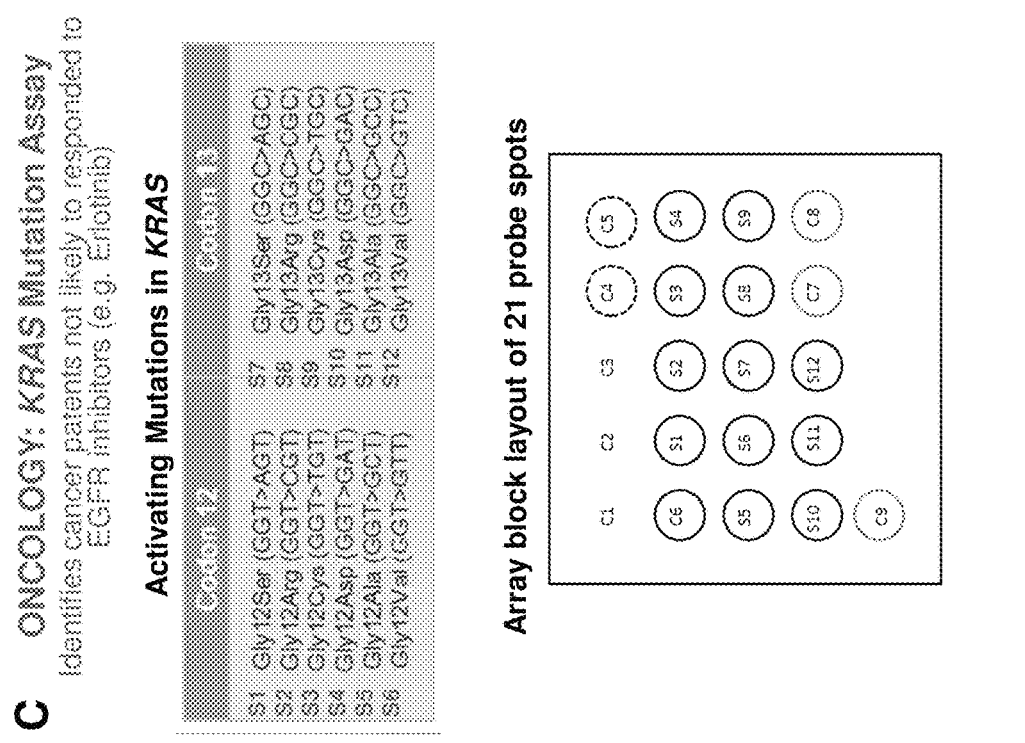

KRAS Mutation Assay
Identifies cancer patents not likely to responded to EGFR inhibitors (e.g. Erlotinib)

Results *KRAS* Mutation Assay

FIG. 23  Results *KRAS* Mutation Assay

DNA Melting Kinetics on Standard Microarray Surface Chemistry

FIG. 26
Comparison Liquid Phase PCR / Solid Phase PCR
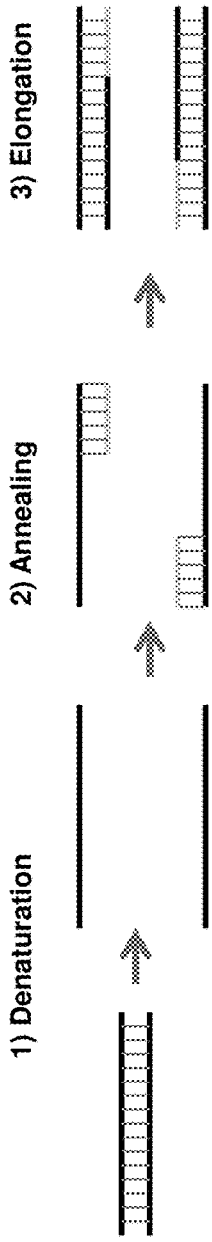
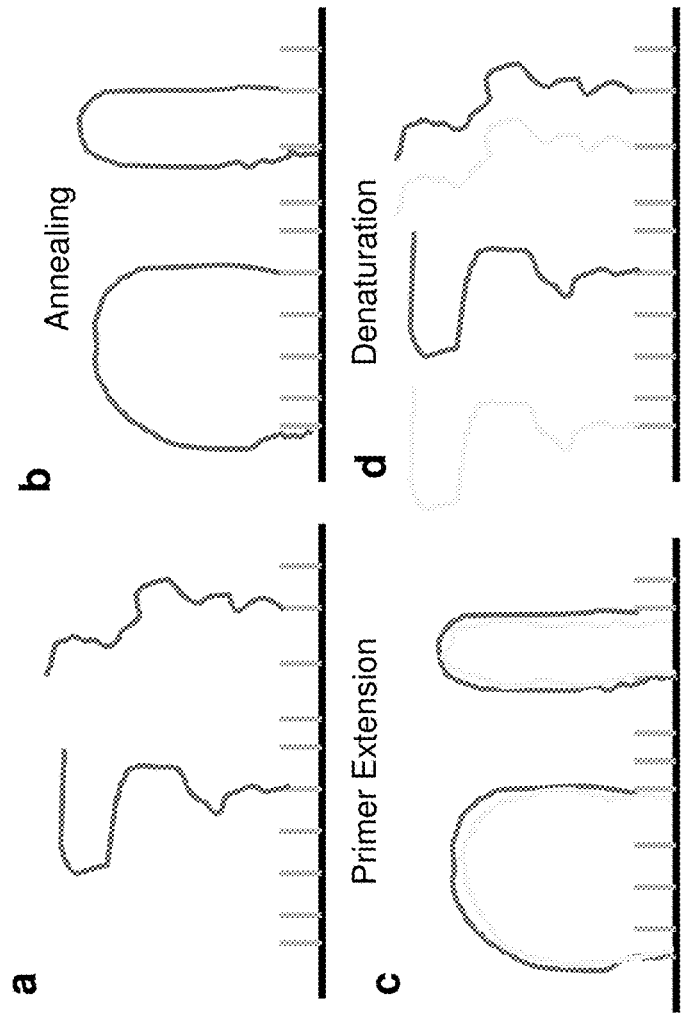

FIG. 27
Custom Nano-Particle Oligo
A) Nano-Particle Components
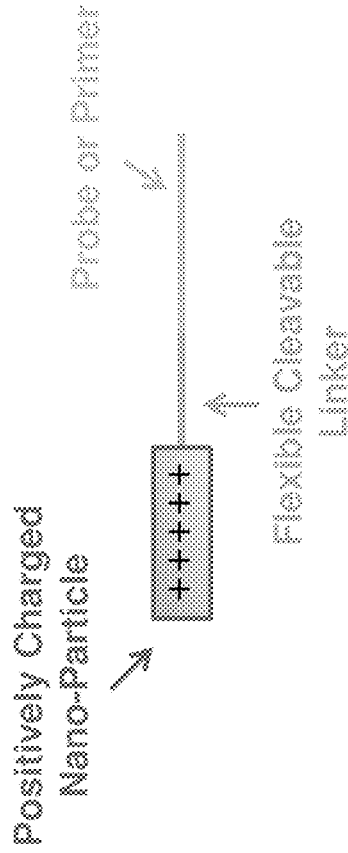
B) PCR Primer
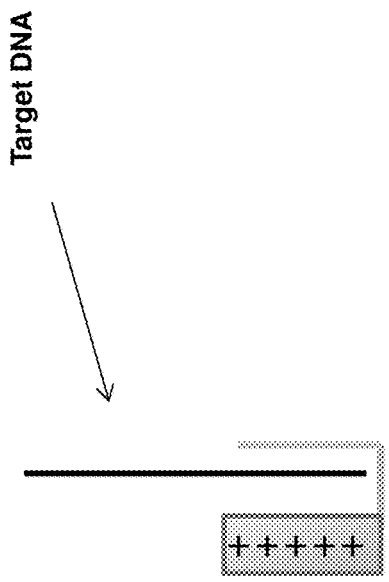
C) Microarray Probe
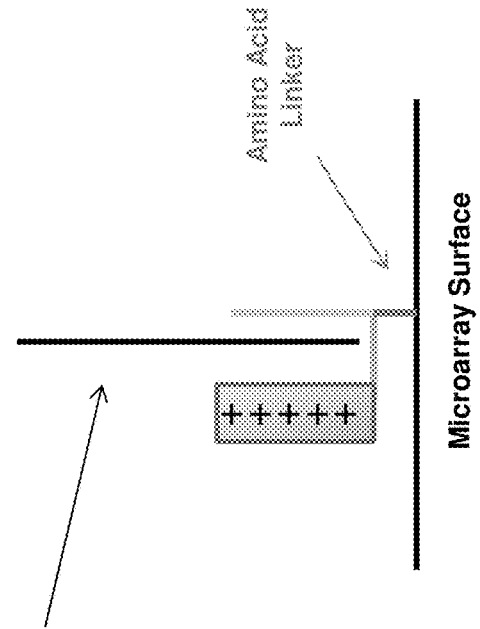

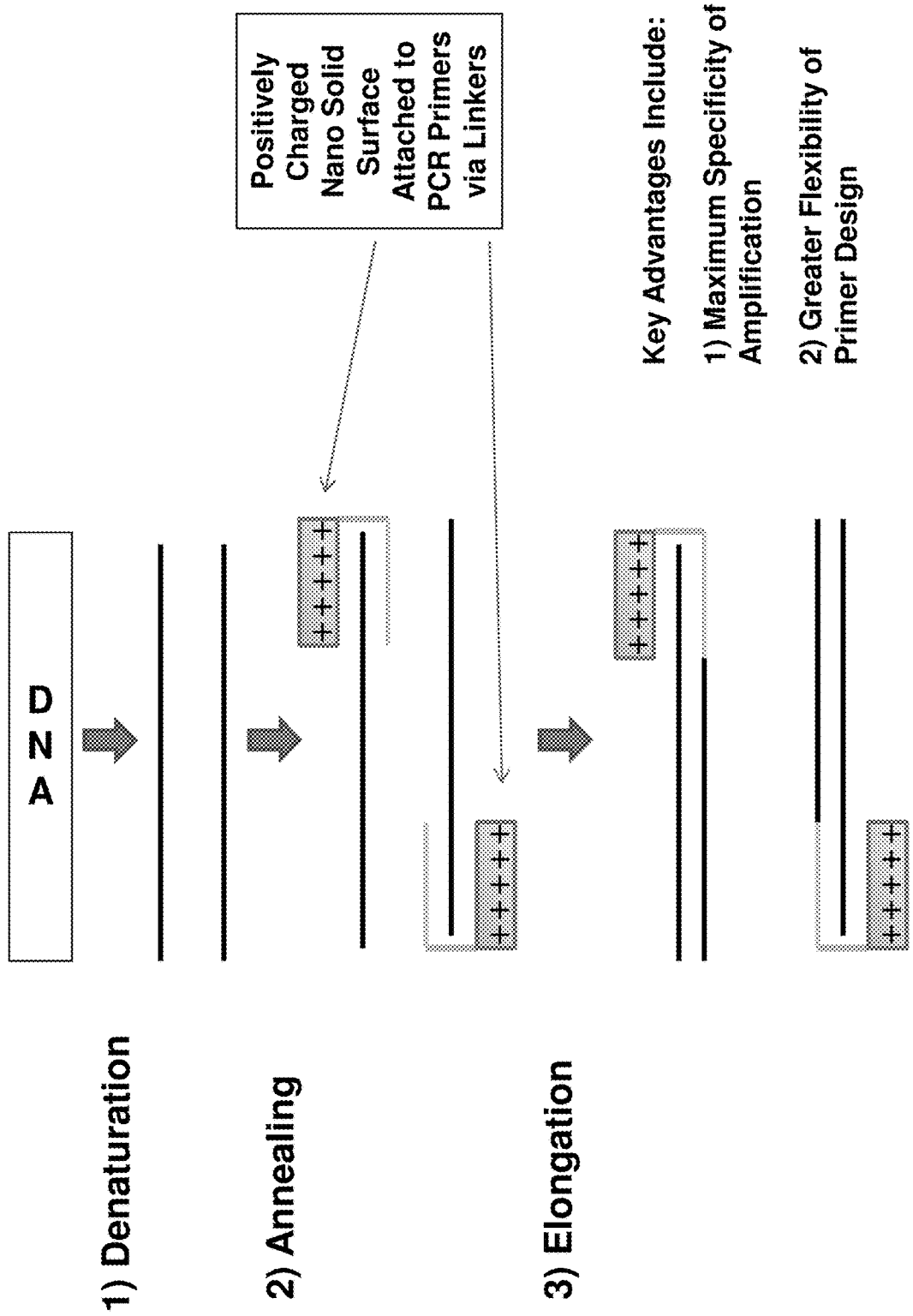

SYSTEMS, METHODS, AND COMPOSITIONS FOR ENHANCING THE SPECIFICITY OF NUCLEIC ACID HYBRIDIZATION

CROSS-REFERENCE TO RELATED APPLICATIONS

This application is a continuation of co-pending U.S. patent application Ser. No. 15/376,555, filed on Dec. 12, 2016. The application Ser. No. 15/376,55 claims priority to U.S. provisional patent application No. 62/266,143, filed on Dec. 11, 2015 and is a continuation-in-part of commonly owned U.S. patent application Ser. No. 13/445,873, filed on Apr. 12, 2012, now U.S. Pat. No. 9,856,523, issued on Jan. 2, 2018; which claims priority to U.S. provisional patent application No. 61/474,727, filed on Apr. 12, 2011. The entire contents of each of the foregoing applications are hereby incorporated by reference in their entirety as if fully set forth herein.

The entirety of the electronically filed sequence listing text file named Sequence_Listing_ST25.txt, created Sep. 14, 2018, 5 kB, is incorporated by reference herein.

FIELD OF THE INVENTION

The present invention generally relates to systems, methods and compositions for improving the specificity of nucleic acid hybridization. More particularly, to specifically in improving the accuracy of microarray technology, such as microarray gene expression profiling, single nucleotide polymorphism (SNP) analysis and any assay requiring hybridization, including PCR and Next Gen DNA sequencing.

BACKGROUND OF THE INVENTION

Nucleic acid hybridization methods are currently used to detect the presence of nucleic acid regions known or suspected to be associated with the natural functioning of a living organism or nucleic acid residues obtained from various sources. Nucleic acid hybridization can also be used to detect sections of nucleic acid regions known or believed to be associated with an organism's disease state, metabolic state or life stage that the organism is experiencing during its life cycle. The accuracy of hybridization typically can be revealed during melting curve analysis of hybridized nucleic acid regions. Still further, there is a need for systems, methods, and compositions of matter to improve the specificity of binding between nucleic acid regions of nucleic acid sources.

Microarray technology has been the dominant genomics methodology but suffered from problems with repeatability and inaccuracy. In the quest for superior methods for genomics analysis, an abundance of next generation sequencing (NGS) methods were developed since the late 2000s. This allowed sequencing the human genome to drop in price from about $3 billion (2004) to approximately $20 k per genome as of early 2010. Genomics is certainly one of the fastest developing areas of the life sciences but large gaps continue to exist in the price performance of NGS in relation to other genomics techniques. While there have been dramatic pricing drops for the actual sequencing process, the price of NGS when used for gene expression profiling and SNP analysis is not competitive with microarrays that range in the hundreds of dollars per assay.

Furthermore, NGS techniques were developed for whole genome sequencing and sequence all DNA present in the sample. Analysis of specific parts of the genome or a subset of genes requires capture-enrichment assays. These consist of standard microarray chips which hybridize specific sequences but allow other unwanted sequences to be washed away. While, enrichment can be over 100 fold using this methodology, only between 30% to 60% of the captured DNA can come from the desired sections of the genome. As a result, capture enrichment assays typically are not very efficient and the depth or redundancy of sequence coverage varies with each experiment.

The melting curve microarray originated as a method for improving the accuracy of microarray gene expression profiling. The use of its technology is envisioned to simplify and lower cost for single nucleotide polymorphism (SNP) analysis. Melting curve analysis of double stranded DNA (dsDNA) has been practiced since the early 1960s in single tube reactions also referred to as liquid phase reactions. These experiments were done in tubes or liquid phase with the DNA free in solution. Since the discovery of melting analysis, the bulk of research has been spent studying liquid phase reactions. A common limitation to liquid phase melting curves is the inability to achieve one base pair resolution of detection. However, the application of melting curve analysis to the microarray or solid phase reaction is a relatively new and not completely understood process.

At the present time, there exists a need for a method and apparatus that can utilize measurement of the melting of target DNA away from probes bound to a glass microarray and that should distinguish between perfect match and mismatches on an individual probe spot and approximate the relative amounts of each species at a very low cost. Still further, it would be advantageous to have systems, methods and compositions for enhancing the specificity of nucleic acid hybridization. Further, it would be advantageous to have a method that can simultaneously analyze DNA sequence data while functioning as capture-enrichment tool, has sensitivity, is not time-consuming and is efficient, safe, and effective. Moreover, these methods, systems and compositions can be useful for improving the specificity of nucleic acid hybridization and their applications in health care, environmental research, pharmaceutical industry and food industry and are applicable for many other diagnostic, biotechnical and scientific purposes.

SUMMARY

The present invention is directed to methods, systems, and compositions of matter are provided to enhance the inter-nucleic acid binding at the surface of a solid and to obtain melting curve patterns to optimize the matching between nucleic acid regions.

In accordance with the present invention, enhanced melting curves and "Charged Enhanced Specificity of Binding" (CESB) are provided. From hereinafter, this is termed "Charged Enhanced Specificity of Binding" (CESB).

Preferably, the enhanced melting curves are due to the additional attractive force the positively charged surface exerts on the DNA. Preferably, CESB can create hybridization conditions with maximum specificity and without any loss of sensitivity. More preferably, CESB can occur whenever a positively charged surface is present with the correct ion concentration in the buffer. In a preferred embodiment of the present invention, creating enhanced melting curves and CESB preferably requires a positively charged surface and interplay with the ion concentration of the buffer. Preferably, the surface charge density of the solid surface is even and consistent. If, for example, the surface charge density varied from spot to spot, the results would vary and be inconsistent.

In a preferred embodiment in accordance with the present invention, not only must quality control levels be higher than other applications such as classic microarrays, but special handling and packaging methods may be needed to preserve the surface chemistry.

In accordance with the present invention, the advantages of using the positively charged microarray surface not only create an enhanced melting curve that can detect the binding and melting of perfectly matched and 1 bp mismatched target, but also create conditions that separate the temperature ranges of melting leading to a temperature of hybridization with maximum levels of specificity for the detection of perfectly matched target DNA without loss of any sensitivity. Preferably, charge enhanced specificity of binding can be used to improve the specificity of any hybridization reaction provided the reaction can be done in a solid phase format. A list of methods that would benefit from CESB may include but is not limited to southern blots, northern blots, microarray, PCR and any form of next generation DNA sequencing incorporating a hybridization step.

In accordance with yet another preferred embodiment of the present invention, a novel method in cancer diagnostic assay for KRAS mutations has been developed and is provided. Typically, this assay comprises 12 different mutations occurring within 6 base pairs. Preferably, this test can be performed by melting curve analysis or by CESB during hybridization, or by CESB in a solid phase PCR format according to the methods disclosed in the present invention.

In yet another embodiment of the present invention, CESB and enhanced melting curves can be performed in the liquid phase format with special adaptations that allow a miniature solid surface with positive charge to be attached to a probe or primer. This allows liquid phase methods like PCR to benefit from CESB.

In one embodiment, the surface of a solid is exposed with a first solution having a composition to impart a positive charge to the surface. Thereafter, a first nucleic acid source or solution is exposed to the positively charged surface. Then, after removal of any unbound first nucleic acid, a second nucleic acid source or solution is offered to the first nucleic acid bound surface at conditions to produce a hybridized nucleic acid pair. After hybridization, the hybrid nucleic acid pair is heated sufficiently to reveal a melting curve. The method, system, and compositions also provide for adjusting the melting curve shape to attain a stepwise pattern by altering the composition and/or exposure of the first solution, and/or the solution containing the first nucleic acid source and/or exposure of the first nucleic acid solution, and/or the solution containing the second nucleic acid source.

In a preferred embodiment of the present invention, the melting curve shape is adjusted to attain a step wise pattern by altering the composition of at least one of the first solution, the first nucleic acid solution, and the second nucleic acid solution.

The positively charged particle comprises a surface coating of positively charged chemicals. Preferably, the positively charged chemicals can be selected from the group consisting of polyethyleneimine, epoxide, amine, epoxysilane and any chemical compound with a positive charge. More preferably, the positively charged chemical is polyethyleneimine and is present in the amount from about 1% to about 10%.

Typically, the nucleic acid can be a segment of DNA or RNA. The first nucleic acid can be a DNA or RNA fragment.

The first nucleic acid can be a probe. Preferably, the solid can be selected from the group consisting of polystyrene, microbeads, glass, metal, charcoal, colloidal gold, bentonite, polypropylene, plastics and silica. More preferably, the solid particle is glass. Even more preferably, the solid particle is a glass slide and is a micro array glass slide. The micro array glass slide comprises from about 10 to about 4.2 million probes.

The first nucleic acid can include a label. The label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, CASCADE BLUE fluorescent dye, Oregon Green, eosins, erythrosin, pyridyloxazoles, benzoxadiazoles, aminonapthalenes, pyrenes, maleimides, coumarins, Lucifer Yellow, Propidium iodide, porphyrins, CY3 cyanine dye, CY5 cyanine dye, CY9 cyanine dye, lanthanides, cryptates, and lanthanide chelates.

The reaction mixture can further include a buffer.

The present invention is also directed to methods and an apparatus for high accuracy genomic analysis platform utilizing hybridization and chemically enhanced dissociation that meets these needs. The methods and apparatus according to the present invention, can be used in capture/enrichment, gene expression profiling and targeted sequencing.

Embodiments of the present invention provide a solution to improving the accuracy and stringency of microarrays and/or other genomic analysis methods relying on nucleic acid hybridization and melting curve analysis. Methods are provided by controlling the surface chemistry of the slide and development of an improved microarray reader. In an advantageous embodiment, there is a method of producing, through initial synthesis, manufacture or through secondary applications, a positively charged surface or surface coating, on the surface of microarray slides or other types of surfaces used for similar purposes, such as micro beads, which enhances melting curve analysis to the point of allowing the detection or differentiation of small changes in sequences between nucleic acid binding partners. As example embodiments, polyethyleneimine, epoxide or a variety of other positively charged chemicals or even the use of an electrical current across the surface to generate a positive charge, can be used for the enhancement of DNA microarray melting curve analysis or other hybridization based assays.

The present invention is directed to a method of enhanced inter-nucleic acid binding at the surface of a solid, to capture/enrichment, detecting the presence, measuring the amount or verifying the sequence of a target polynucleotide of interest in a test sample. The method comprises exposing the surface with a solution sufficient to attain a positively charged surface; exposing a first nucleic acid solution to the positive charged surface to produce a first nucleic acid bound surface; wherein the first nucleic acid solution comprises a first probe. The method further comprises exposing a second nucleic acid solution to the first nucleic acid bound surface to produce a hybridized nucleic acid pair; wherein the second nucleic acid solution comprises the target polynucleotide; whereby the first probe is complementary to portions of the target polynucleotide sequence. The method further comprises heating the hybridized nucleic acid pair sufficiently to reveal a bi-phasic melting curve shape; whereby the positively charged surface improves stringency during hybridization of the nucleic acid pair by changing kinetics of unbinding of the target polynucleotide, correlating with temperature changes and thermal dissociation characteristics for analysis, to the point that detection, quantification or differentiation of small sequence differences between nucleic acid hybrids in the target polynucleotide and the first probe. By this method, the small sequence difference can be one base pair such that a temperature range of melting of one base pair mismatched target polynucleotide and temperature range of melting of perfectly matched target polynucleotide have different temperature ranges and no longer overlap. Furthermore, in this method, the positively charged surface of the solid changes the kinetics by narrowing the temperature range of melting between the one base pair mismatch and the perfectly matched target polynucleotide thereby producing a distinctive melting curve with a change in a slope of the curve effectively forming a biphasic melting curve consisting of two separate melting curves with a short section between the two curves where no melting occurs.

The present invention is directed to a method of capture/enrichment, detecting the presence, measuring the amount or verifying the sequence of a target polynucleotide of interest in a test sample. The method comprises the steps of forming a reaction mixture by combining in an assay medium: (i) a first reagent comprising a first probe bound to a solid particle, and (ii) an aliquot of the test sample suspected of containing the target nucleotide sequence. The first probe comprises a first single stranded nucleic acid fragment complementary to a first of two separated strands of a selected segment of the target nucleotide sequence. The solid particle is a positively charged solid particle. The first probe is complementary to mutually exclusive portions of the target polynucleotide sequence.

The reaction mixture is then subjected under denaturing conditions rendering the target polynucleotide sequence in the sample to be single stranded. The reaction mixture is then incubated under hybridization conditions to cause hybridization between the first probe and the first strand of the selected segment of the target polynucleotide sequence. In the presence of the target polynucleotide, substantially all of the first probe will be hybridized to the first strand of the selected segment of the target polynucleotide sequence producing bound target polynucleotide sequence. The reaction mixture is then exposed to disassociation conditions.

The reaction mixture is then monitored. Preferably, disassociation correlates with changes in the presence of the bound target polynucleotide providing disassociation curve analysis.

The positively charged solid particle enhances thermal disassociation characteristics for analysis, to the point of allowing the detection, amount or differentiation of small sequence differences between nucleic acid hybrids in the target polynucleotide and the first probe. The small sequence differences can be down to one base pair.

The target polynucleotide can be a segment of DNA or RNA. The first probe can be a DNA or RNA fragment. Typically, the first probe can be bound to the solid particle by a linker. Preferably, the solid particle can be selected from the group consisting of polystyrene, microbeads, glass, metal, charcoal, colloidal gold, bentonite, polypropylene, plastics and silica. More preferably, the solid particle is glass. Even more preferably, the solid particle is a glass slide and is a micro array glass slide. The micro array glass slide comprises from about 10 to about 4.2 million probes.

The positively charged particle comprises a surface coating of positively charged chemicals. Preferably, the positively charged chemicals can be selected from the group consisting of polyethyleneimine, epoxide, amine, epoxysilane and any chemical compound with a positive charge.

More preferably, the positively charged chemical is polyethyleneimine and is present in the amount from about 1% to about 10%.

The positively charged particle can comprise a surface coating of positively charged chemicals generated by use of an electrical current across the surface to generate a positive charge.

Typically, the target polynucleotide sequence can include a label. The label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, CASCADE BLUE fluorescent dye, Oregon Green, eosins, erythrosin, pyridyloxazoles, benzoxadiazoles, aminonapthalenes, pyrenes, maleimides, coumarins, Lucifer Yellow, Propidium iodide, porphyrins, CY3 cyanine dye, CY5 cyanine dye, CY9 cyanine dye, lanthanides, cryptates, and lanthanide chelates.

Preferably, the step of exposing the reaction mixture to disassociation conditions can be carried out over a temperature range from about 0° C. to about 100° C., with temperature increase increments of from about 0.01° C. to about 5.0° C.

The steps of forming, subjecting, incubating, exposing and monitoring were carried out by an automated micro array device.

The first probe can include a label. The label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, CASCADE BLUE fluorescent dye, Oregon Green, eosins, erythrosin, pyridyloxazoles, benzoxadiazoles, aminonapthalenes, pyrenes, maleimides, coumarins, Lucifer Yellow, Propidium iodide, porphyrins, CY3 cyanine dye, CY5 cyanine dye, CY9 cyanine dye, lanthanides, cryptates, and lanthanide chelates.

The reaction mixture can further include a buffer.

The present invention is directed to a micro array apparatus for genome sequence analysis comprising: a base structure comprises: a melting curve microarray reader cassette; wherein the cassette configured to hold microarray slides; a thermal control chamber comprising a heat control unit and a fluids control unit; wherein the heat control unit measures temperature data for melting curve analysis; an optical system for measuring the presence or absence, and concentration of labeled nucleic acid sample providing the concentration data for melting curve analysis; and an automatic focusing system. Preferably, a computerized Z-axis is added to the thermal control chamber to speed up a focusing procedure and allow automatic incremental adjustments of focus. Preferably, the melting curve data is sufficient to distinguish between the melting of different sequences of target DNA with one base pair sensitivity for each probe spot of a microarray, allowing for scanning of entire genome sequencing.

In summary, methods, systems and compositions of the present invention improves the accuracy of nucleic acid hybridization.

BRIEF DESCRIPTION OF THE DRAWINGS

These and other features, aspects, and advantages of the present invention will become better understood with reference to the following description, appended claims, and accompanying drawings where:

FIG. 7 illustrates an exemplary example of DNA melting curves in liquid phase solutions and solid phase according to an embodiment of the present invention.

FIG. 10 illustrates an exemplary example of application of DNA to an amine coated array according to an embodiment of the present invention;

FIG. 11A illustrates an exemplary comparison of microarray images obtained during a melting experiment between the temperatures of 45° and 65° C. according to the embodiments of the present invention.

FIG. 11B illustrates exemplary results of array hybridized with human cDNA stained with CY3 dye according to the embodiments of the present invention.

FIG. 13 illustrates an exemplary example of epoxysilane surface attachment and blocking or deactivation of the surface by ethanolamine according to an embodiment of the present invention.

FIG. 19 illustrates an exemplary diagram of how positively charged microarray surface can attract negatively charged nucleic acids directly above the charged surface, enhancing nucleic acid melting according to an embodiment of the present invention.

FIG. 20 illustrates an exemplary overview of the KRAS Mutation Assay according to an embodiment of the present invention; and an exemplary example of the preferred embodiment of the invention and the potential for diagnostic applications.

FIG. 26 illustrates exemplary binding mechanisms of liquid phase and solid phase PCR according to an embodiment of the present invention;

FIG. 27 illustrates an exemplary example of a custom synthesized oligo bound to a nano particle according to an embodiment of the present invention;

FIG. 28 illustrates an exemplary schematic diagram of hybrid liquid-solid phase PCR according to a preferred embodiment of the present invention.

DETAILED DESCRIPTION

According to the present invention, there is provided a method for improving the accuracy and stringency of microarrays and/or other genomic analysis methods relying on nucleic acid hybridization and melting curve analysis by controlling the surface chemistry of the slide. The method comprises producing a positively charged surface or surface coating, on the surface of microarray slides or other types of surfaces used for similar purposes, such as nano particles and micro beads, which enhances melting curve analysis to the point of allowing the detection or differentiation of small changes in sequences between nucleic acid binding partners. There is also provided an improved microarray reader machine, to collect melting curve data on microarray slides containing 1000 probe spots or more. In addition, the accuracy or resolution of melting curve analysis was to be sufficient to distinguish between the melting of perfect matched dsDNA and dsDNA with the smallest possible change in sequence, a one base pair mismatch.

In preferred embodiments of the present invention, the methods and apparatus according to the present invention, can be used in capture/enrichment, gene expression profiling and targeted sequencing. Particularly, in an embodiment of the present invention, there is a method of capture/enrichment of a target polynucleotide of interest in a test sample. In another embodiment of the present invention, there is a method of detecting the presence of a target polynucleotide of interest in a test sample. In yet another embodiment of the invention, there is a method of measuring the amount of a target polynucleotide of interest in a test sample. In another and more preferable embodiment of the present invention there is a method of verifying the sequence of a target polynucleotide of interest in a test sample.

Figure 1:
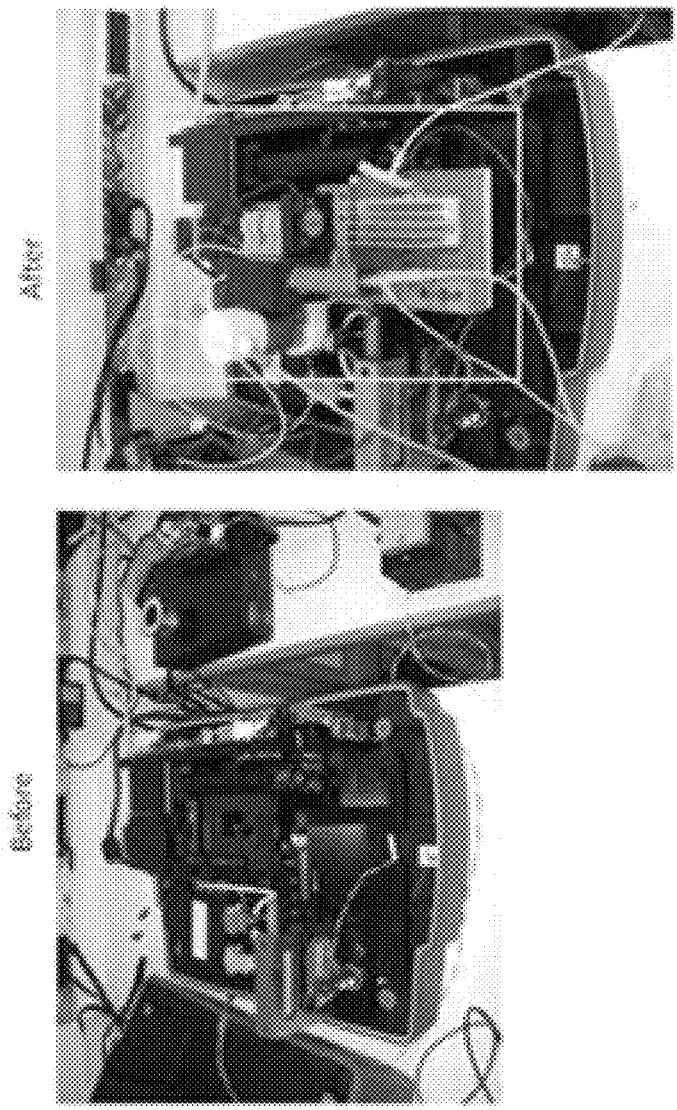
FIG. 1 illustrates an exemplary prototype melting curve microarray reader machine according to an embodiment of the present invention.

In one particular embodiment of the present invention, preliminary data obtained suggests that creating melting curve analysis on a microarray significantly improves the accuracy of microarrays. According to the present invention, FIG. 1 illustrates an exemplary device according to the present invention. With respect to FIG. 1, a cost saving measure the first melting curve microarray reader was a modified Axon 4000a (Molecular Devices, Sunnyvale, Calif.) machine in which heat control and fluidics were combined with existing scanning capability. Initial experiments utilized a commercial microarray chip "Check It Chips" with large 300 μM probe spots and 70 mer probe sequences for the human genome printed in blocks of 100 spots for a total of 2 blocks or 200 probe spots per array (commercially available from ARRAYIT Corporation, Sunnyvale, Calif.). According to the present invention, these slides typically have an amine coated surface and probes attached via UV cross linking. Human cDNA stained with CY3 dye (ARRAYIT Corp.) was used as target DNA for hybridization. Typically, melting experiments can be carried out in a temperature range from about 0° C. to about 100° C. Preferably, melting experiments were carried out over a temperature range from about 40° C. to about 70° C., preferably with temperature increase increments of 1° C. and fluidics buffer flush of 600 μl of 2.5×SSC.

Embodiments of the present invention provide a solution to improving the accuracy and stringency of microarrays and/or other genomic analysis methods relying on nucleic acid hybridization and melting curve analysis. Methods are provided by controlling the surface chemistry of, for example, a microarray slide and development of an improved microarray reader. In an advantageous embodiment, there is a method of producing, through initial synthesis, manufacture or through secondary applications, a positively charged surface or surface coating, on the surface of microarray slides or other types of surfaces used for similar purposes, such as micro beads, which enhances melting curve analysis to the point of allowing the detection or differentiation of small changes in sequences between nucleic acid binding partners. As example embodiments, polyethyleneimine, epoxide or a variety of other positively charged chemicals or even the use of an electrical current across the surface to generate a positive charge, can be used for the enhancement of DNA microarray melting curve analysis or other hybridization based assays.

In a preferred embodiment of the present invention, after hybridization has taken place, chemicals on the surface of the microarray that are positively charged exert an attractive effect on both strands of DNA (both probe and target) that is really a type of chemical bond. Typically, this is not an electrical field or electrical current. Preferably, this bond can be reversibly broken by heat. In accordance with the present invention, there may be multiple types of bonds forming and existing at the same time, which include but are not limited to ionic, electrostatic, and Van der Waals Forces.

In a preferred embodiment of the present invention, when energy in the form of heat is applied to the microarray, 2 different types of chemical bonds must be broken to allow the target polynucleotide to melt away or dissociate, the hydrogen bonds between the complementary probe and target polynucleotide, and the attractive force with the positively charged surface. Because there are 2 different types of bonds being broken at the same time, this causes a change in the way the target polynucleotide dissociates. Rather than melting apart over a range of temperature, for example, a 5° C. range, the target polynucleotide can melt away over a much shorter temperature range of, for example, 1° C. or even less. Note that in order to exert this effect, the positively charged surface bonds with the target polynucleotide and produces a beneficial effect.

In accordance to a preferred embodiment of the present invention, if two different sequences of polynucleotide (for example, DNA) are hybridized to the same probe sequence of a given probe spot, for example perfect match and 1 bp mismatch, the surface has positively charged chemicals, and heat is applied, the temperature ranges of melting of both the perfect match and one base pair mismatch will become narrower. The temperature ranges of melting of the two different target sequences will become so narrow that they no longer overlap. When this is graphed, it produces a 2-stepped curves or bi-phasic type melting curve where the 1 base pair mismatch melts first, then the downward slope stops for a short interval after the 1 base pair mismatch has completed melting but before the perfect match starts to melt. This change in slope indicates no DNA melting is taking place. Then the downward slope begins at a slightly higher temperature when the perfect match begins to melt.

The present invention is directed to a method of capture/enrichment, detecting the presence, measuring the amount or verifying the sequence of a target polynucleotide of interest in a test sample. The method comprises the steps of forming a reaction mixture by combining in an assay medium: (i) a first reagent comprising a first probe bound to a solid particle, and (ii) an aliquot of the test sample suspected of containing the target nucleotide sequence. The first probe comprises a first single stranded nucleic acid fragment complementary to a first of two separated strands of a selected segment of the target nucleotide sequence. The solid particle is a positively charged solid particle. The first probe is complementary to mutually exclusive portions of the target polynucleotide sequence.

The reaction mixture is then subjected under denaturing conditions rendering the target polynucleotide sequence in the sample to be single stranded. The reaction mixture is then incubated under hybridization conditions to cause hybridization between the first probe and the first strand of the selected segment of the target polynucleotide sequence. In the presence of the target polynucleotide, substantially all of the first probe will be hybridized to the first strand of the selected segment of the target polynucleotide sequence producing bound target polynucleotide sequence. The reaction mixture is then exposed to disassociation conditions.

The use of nucleic acid hybridization as an analytical tool is based on the double stranded duplex structure of DNA. The hydrogen bonds between the purine and pyrimidine bases of the respective strands in double stranded DNA can be reversibly broken. The two complementary strands of DNA resulting from this melting or denaturation of DNA will associate (also referred to as reannealing or hybridization) to reform the duplexed structure. Contact of a first single stranded nucleic acid, either DNA or RNA, which comprises a base sequence sufficiently complementary to a second stranded nucleic acid under appropriate conditions, will result in the formation of nucleic acid hybrids, as the case may be.

The reaction mixture is then monitored. Preferably, dissociation correlates with changes in the presence of the bound target polynucleotide providing disassociation curve analysis. The positively charged solid particle enhances thermal disassociation characteristics for analysis, to the point of allowing the detection, amount or differentiation of small sequence differences between nucleic acid hybrids in the target polynucleotide and the first probe. The small sequence differences can be down to one base pair.

Preferably, the target polynucleotide can be a segment of deoxyribonucleic acid (DNA) sequence or ribonucleic acid (RNA) sequence. The target polynucleotide sequence of interest can be any polynucleotide sequence present naturally in a sample. It can be in a material in or derived from a cellular system. The polynucleotide sequence can be any gene or polynucleotide sequence of interest (DNA or RNA).

In a preferred embodiment of the present invention, the first probe can be a nucleic acid fragment, preferably, a DNA or RNA fragment. More preferably, the first probe comprises a first single stranded nucleic acid fragment complementary to a first of two separated strands of a selected segment of the target polynucleotide sequence. The nucleic acid fragments can be produced or obtained by any method known to those of ordinary skill in the art, e.g., synthetic production methods or enzymatic production methods, both in vitro and in vivo. DNA and RNA probes preferably are single stranded nucleic acid molecules generally synthesized by gene machines or made using recombinant DNA methods known to those skilled in the art.

Preferably, the first probe will exhibit detectable hybridization at one or more points with the target polynucleotide sequence of interest. More preferably, the nucleic acid probe fragment attached to the solid particle can be of almost any length, provided that the fragment is long enough to form a stable nucleic acid hybrid with the selected segment of the target polynucleotide sequence. The first probe nucleic acid fragment will typically have a minimum 4-base sequence, one case greater than an amino acid codon. Preferably, the first probe nucleic acid fragment is from about 4 to about 80 nucleotides in length. The more nucleotides, the greater the specificity.

Typically, the first probe can be bound to the solid particle by a spacer linker.

Preferably, the solid particle can be any insoluble particle that is capable of attaching DNA or RNA. The DNA or RNA can be attached to the solid particle by any known methods known to those of ordinary skill of the art including but not limited to chemical bonds, including covalent bonds, ionic bonds and electrostatic attractions. Preferably, the solid particle can be selected from the group consisting of polystyrene, microbeads, glass, metal, charcoal, colloidal gold, bentonite, polypropylene, plastics and silica. More preferably, the solid particle is glass. Even more preferably, the solid particle is a glass slide and is a micro array glass slide.

In a more preferred embodiment of the present invention, any number of probes can be possible and can be tailored accordingly. For example, for simple applications, as little as 10 probe spots can be used, for example, on a micro array slide and for a high throughput, millions of probe spots can be used and tailored accordingly. Determining the number of probes to be used can be accomplished by any method known to those skilled in the art. Preferably, the micro array glass slide comprises from about 10 to about 4.2 million probes.

According to the present invention, probes comprise a single stranded nucleic acid fragment complementary to a first of two separated strands of a selected segment of a target polynucleotide sequence. The nucleic acid fragments can be fragments from deoxyribonucleic acid (DNA) or ribonucleic acid (RNA) sequences. Preferably the nucleic acid fragment is single stranded. The nucleic acid fragments can be produced or obtained by any method known to those of ordinary skilled in the art, e.g., synthetic production methods or enzymatic production methods, both in vitro and in vivo. DNA and RNA probes are single-stranded nucleic acid molecules generally synthesized by so called gene machines or made using recombinant DNA methods.

In yet another preferred embodiment of the present invention, the first probe strands are not attached directly to the solid particle, such as a microarray surface, but preferably attached by using a linker, which can elevate the DNA off the surface. More preferably, the linkers can be made primarily to allow the DNA to be at a greater distance off the surface of the slide, but can also have additional chemical properties, for example, if the linker were to have a positive charge, it may be able to replicate the results achieved with just a positively charged surface.

As used herein, the term "hybridization conditions" means those conditions which enable the hybridization between the first probe attached to the solid particle to a first strand of the selected segment of target polynucleotide sequence. According to the present invention, hybridization techniques and melting curve analysis are typically known to those skilled of ordinary skill in the art and can be used in the present invention.

The choice of solid particle can be governed by the effect of rate of hybridization and binding of the probe to the target DNA. The solid particle preferably should provide sufficient sensitivity in order to detect the amount of target nucleotide sequence available for hybridization. Other consideration will be the ease of synthesis of the probe, the availability of instrumentation, the ability to automate and convenience.

In yet a preferred embodiment of the present invention, by controlling the surface chemistry of the solid particle. More preferably, the solid particle will have a positively charged surface or surface coating, which enhances melting curve analysis to the point of allowing the detection or differentiation of small changes in sequences between nucleic acid binding partners, the detection or differentiation of small changes in sequences can be up to one base pair.

In yet another preferred embodiment of the present invention, any cationic or other positively charged chemicals can be used to coat the solid particle surface. More preferably, the positively charged particle comprises a surface coating of positively charged chemicals. Preferably, the positively charged chemicals can be selected from the group consisting of polyethyleneimine, epoxide, amine and including but not limiting any chemical compound known to those with ordinary skill in the art with a positive charge. More preferably, the positively charged chemical is polyethyleneimine and is present in the amount from about 1% to about 10%.

In yet an alternate preferred embodiment of the present invention, the positively charged particle can comprise a surface coating of positively charged chemicals generated by use of an electrical current across the surface to generate a positive charge that can be used for the enhancement of DNA micro array melting curve analysis or other hybridization based assays.

Typically, the target polynucleotide sequence can include a label. The label can be any label or tag known to those skilled in the art. The label can include dyes, radioactive labels, gold, silver, beads, antibody or any other label known to those skilled in the art to label or tag a polynucleotide sequence. Preferably, the label can be a fluorescent dye selected from the group consisting of 2-((iodoacetyl)amino) ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, CASCADE BLUE fluorescent dye, Oregon Green, eosins, erythrosin, pyridyloxazoles, benzoxadiazoles, aminonapthalenes, pyrenes, maleimides, coumarins, Lucifer Yellow, Propidium iodide, porphyrins, CY3 cyanine dye, CY5 cyanine dye, CY9 cyanine dye, lanthanides, cryptates, and lanthanide chelates. More preferably, CY3 is used as the dye.

In a more preferred embodiment of the present invention, the step of exposing the reaction mixture to disassociation conditions, means exposing the reaction mixture to any melting temperature or melting conditions known to those skilled in the art. Disassociation and melting can be used interchangeably from here throughout the specification. Disassociation or melting conditions can be any conditions known but not limited to those with skilled in the art, including heat, chemicals, electrical current or other types of fluid or sound waves. More preferably, disassociation means melting conditions.

In the disassociation conditions, the melting temperature can be calculated using the probe sequence and buffer composition. The melting temperature typically is the lowest temperature that will allow all of the target to be release from the probe. If the melting temperature is too low the target will not be released. Using a high melting temperature can have no negative effect on the results other than consuming more time and energy.

Preferably, when the determining the range of temperature for the melting (dissociation) reaction to take place it usually starts at or below the hybridization temperature and ends a little above the melting temperature.

Typically, the step of exposing the reaction mixture to disassociation conditions can be carried out over a temperature range from about 0° C. to about 100° C. Preferably, the step of exposing the reaction mixture to disassociation conditions can be carried out over a temperature range from about 40° C. to about 70° C., with temperature increase increments of from about 0.01° C. to about 5.0° C. Preferably, the temperature increase increments can be carried out from about 0.01° C. to about 5.0° C.

According to a preferred embodiment of the present invention, in the step of exposing the reaction mixture to melting conditions, the temperature range can vary depending on the probe sequence and probe length, and can be adjusted according to those skilled in the art. Typically, in the step of exposing the reaction to melting conditions, the experiment can be carried out over a temperature range from about 0° C. to about 100° C. Preferably, in the step of exposing the reaction to melting conditions, the experiment can be carried out over a temperature range from about 40° C. to about 70° C.

Typically, the range of temperature over which the experiment can be conducted is determined by the hybridization temperature and the melting temperature of the target sequence and probes. Before the melting reaction is conducted, hybridization can be performed and is accomplished at one specific temperature. Typically, the hybridization temperature can be a temperature suggested by the manufacturing company, for example, of the micro array and a common hybridization temperature typically can be 45° C. Preferably, the range of temperature can be determined by calculating or estimating the temperature in which the target polynucleotide sequence is most likely to bind its complementary first probe. This estimated temperature can vary according to the sequence of nucleic acids and type of buffer used during hybridization. It is well known to those with ordinary skill in the art, that the higher the GC content and the longer the sequence, the higher the hybridization temperature. Using a hybridization temperature lower than one calculated for the best specific hybridization can allow more non-specific binding to occur between probe and target. Using a hybridization temperature that is too high may not allow target to bind probes.

In yet another embodiment of the present invention, in the step of exposing the reaction mixture to disassociation or melting conditions, the temperature increase increments can be from about 0.01° C. to about 5.0° C. Preferably, the temperature increase increments can be from about 0.01° C. to about 3.0° C. The temperature increase increment can be varied according to those skilled in the art, to how much resolution is needed in the melting curve graph analysis. For example, typically, for the following experiments conducted, a 1° C. temperature increase worked well, however, a temperature increment increase of less than 1° C. could add more data points to the graph generated for analysis, thereby increasing the resolution of the melting curve however, would have consumed more time. Accordingly, using a temperature increase increment of more than 1° C. can speed up the experiment, however, there would be a decrease in the resolution of the melting curve. If the resolution of the melting curve was too low, determining the exact temperature in which target and probe melted apart (Tm) would not be possible. Preferably, the temperature increase increment is about 1° C.

The steps of forming, subjecting, incubating, exposing and monitoring preferably are carried out by an automated microarray device.

The first probe can include a label. The label can be any label or tag known to those skilled in the art. The label can include dyes, radioactive labels, gold, silver, beads, antibody or any other label known to those skilled in the art to label or tag a polynucleotide sequence. Preferably, the label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, CASCADE BLUE fluorescent dye, Oregon Green, eosins, erythrosin, pyridyloxazoles, benzoxadiazoles, aminonapthalenes, pyrenes, maleimides, coumarins, Lucifer Yellow, Propidium iodide, porphyrins, CY3 cyanine dye, CY5 cyanine dye, CY9 cyanine dye, lanthanides, cryptates, and lanthanide chelates.

More preferably, CY3 is used as the dye. The fluorescent polynucleotide probes are especially useful in automatic or semiautomatic recording of the results combined with continuous flow systems and instruments.

Preferably, the reaction mixture can further include a buffer. Any buffer known to those of ordinary skill in the art can be used. More preferably, the buffer is selected based on the buffer ionic strength, which can affect the reaction.

The present invention is directed to a microarray apparatus for genome sequence analysis comprising: a base structure comprises: a melting curve microarray reader cassette; wherein the cassette configured to hold microarray slides; a thermal control chamber comprising a heat control unit and a fluids control unit; wherein the heat control unit measures temperature data for melting curve analysis; an optical system for measuring the presence or absence, and concentration of labeled nucleic acid sample providing the concentration data for melting curve analysis; and an automatic focusing system. Preferably, a computerized Z-axis is added to the thermal control chamber to speed up a focusing procedure and allow automatic incremental adjustments of focus. Preferably, the melting curve data is sufficient to distinguish between the melting of different sequences of target DNA with one base pair sensitivity for each probe spot of a microarray, allowing for scanning of entire genome sequencing. The optical system preferably provides fluorescence intensity data, whereas the heat control unit typically provides the reaction mixture temperature data.

In an embodiment of the present invention, FIG. 11A illustrates comparison of microarray images obtained during a melting experiment between the temperatures of 45° and 65° C. As FIG. 11A depicts, repeated cycles of temperature increase, buffer flush, and scans melted away most of the bound target DNA on the slide away by 65° C. confirming release of target DNA.

According to a preferred embodiment of the present invention, in the step of exposing the reaction mixture to melting conditions, the temperature range can vary depending on the probe sequence and probe length, and can be adjusted according to those skilled in the art. Typically, in the step of exposing the reaction to melting conditions, the experiment can be carried out over a temperature range from about 0° C. to about 100° C., preferably from about 40° C. to about 70° C.

In yet another embodiment of the present invention, in the step of exposing the reaction mixture to melting conditions, the temperature increase increments can be from about 0.01° C. to about 5.0° C. Preferably, the temperature increase increments can be from about 0.01° C. to about 3.0° C. The temperature increase increment can be varied according to those skilled in the art, to how much resolution is needed in the melting curve graph analysis. For example, typically, for the following experiments conducted, a 1° C. temperature increase worked well, however, a temperature increment increase of less than 1° C. could add more data points to the graph generated for analysis, thereby increasing the resolution of the melting curve however, would have consumed more time. Accordingly, using a temperature increase increment of more than 1° C. can speed up the experiment, however, there would be a decrease in the resolution of the melting curve. If the resolution of the melting curve is too low, determining the exact temperature in which target and probe melted apart (Tm) would not be possible. Preferably, the temperature increase increment is about 1° C.

In yet another embodiment of the present invention, FIG. 11B depicts results of array hybridized with human cDNA stained with CY3 dye. Melting analysis was performed over the temperature range of 40°-64° C. with readings at 2° C. intervals. Graph A (Cadherin 1 probe) depicts a melting curve showing one large melting point (arrow) at about 63° C. indicating the presence of one major hybridization product. However, Graph B (Beta Actin probe) depicts at least two major melting points (arrows) at 46° and 62° C. This result indicates the presence of multiple hybridization products. Conventional microarray analysis is not capable of making this distinction. The relative abundance of each hybridization product can be inferred from the graph. FIG. 11B shows when actual melting curves were plotted by compiling the fluorescence intensity data at each temperature of scanning for each probe spot, well-formed curves were obtained. Remarkably, these curves exhibited a sharp slope or drop at which DNA melted away from the array which allowed easy discernment of the temperature of melting (Tm) as shown by the arrows (FIG. 11B) and the ability to detect more than one type of target attached to the individual probe spot. The melting curve for the Beta Actin probe spot (FIG. 11B) depicts two distinct melting curves indicating that at least two different types of target DNA were bound.

With this preliminary data in mind, the objectives of the present invention include improving a melting curve microarray reader machine, both instrumentation and software and to demonstrate the ability of the machine to collect melting curve data on microarray slides containing 1000 probe spots or more. In addition, the accuracy or resolution of melting curve analysis was to be sufficient to distinguish between the melting of perfect matched dsDNA and dsDNA with the smallest possible change in sequence, a one base pair mismatch.

According to preferred and particular embodiments of the present invention, systems, methods, and compositions to optimize high-accuracy hybridization between nucleic acid regions of separate DNA or RNA molecules are also provided. Systems include modification of a binding membrane with positive charge to enhance the sticking of nucleic acids contained within a sample to be analyzed with a detection nucleic acid probe. Methods for using the positive charge modified membrane and related compositions are described. Compositions used to enhance the binding and subsequent de-binding in melting curve analysis are also described. Other embodiments according to the present invention, include the teachings of systems, methods, and compositions of matter concerning the enhancement of nucleic acid hybridization specificity and controlling the shapes of melting curves revealed by nucleic acid hybrid pairs to optimize nucleic acid analysis.

According to a preferred embodiment of the present invention, the use of solid phase nucleic acid melting analysis in the presence of a positively charged solid surface preferably are used to enhance the melting curves generated by double stranded nucleic acids.

In yet another preferred embodiment of the present invention, this enhancement involves narrowing the temperature ranges of melting of perfect match and one base pair mismatch such there is no overlap of each melting range. Preferably, once the temperature ranges of melting are separated for the two species of nucleic acids, they become easily detectable after binding the same probe spot using melting curve analysis which is evidenced by a change in the slope of the graph. Preferably, this type of graph is a 2 stepped curve or enhanced melting curve which could distinguish the presence of both perfect math and one base pair mismatch binding. Typically, this detection is not possible using standard microarray surfaces which are normally chemically blocked and neutral in charge.

According to a more preferred embodiment of the present invention, any chemical coating which produces a positively charged surface can be used to coat the solid support or particle. Preferably, the positively charged surface comprises an active surface coating of chemicals forming a positive charge on the surface of the particle. Preferably, the solid support is a slide. The chemical coating includes but is not limited to amines, polyethyleneimine (PEI), epoxysilane and any chemical compound with a positive charge formed on the surface of the particle. It is known to those skilled in the art, that the chemical epoxysilane is neutral in charge but produces a layer of positive charge by forming a dipole during the attachment to the glass microarray surface. The presence of the positively charged solid surface can introduce an attractive force that the negatively charged target strand of nucleic acids must overcome during the melting process in addition to the hydrogen bonds already present between the probe and target strands of DNA. It is believed that this additional attractive force produced by the positively charged surface is responsible for enhancement of the melting curves both narrowing the ranges of melting and further separating the temperatures of melting between the perfect match and 1 base pair mismatch. In a preferred embodiment of the present invention, the solid support is selected from the group consisting of polystyrene, microbeads, glass, metal charcoal, colloidal gold, bentonite, polypropylene, plastics and silica. Preferably, the solid support or particle is glass. More preferably, the solid support is a glass slide.

In a preferred embodiment of the present invention, when the positively charged support or particle comprises an active surface coating of chemicals forming a positive charge on the surface of the support or particle, and the chemical is polyethyleneimine, the polyethyleneimine is present in the amount from about 1% to about 10%. It is reasonable to assume that the level of positive charge on PEI coated arrays of 1%, 5%, and 10% were different, with the higher concentrations having higher levels of positive charge. While positive charge is need to produce the enhanced 2 stepped melting curves, the amount of positive charge needed appears to not be limited to just one specific level of positive charge but can vary to some degree. This is evidenced by the ability of both 1% and 10% PEI coatings being able to produce 2 stepped melting curves but with different characteristics.

Figure 16:
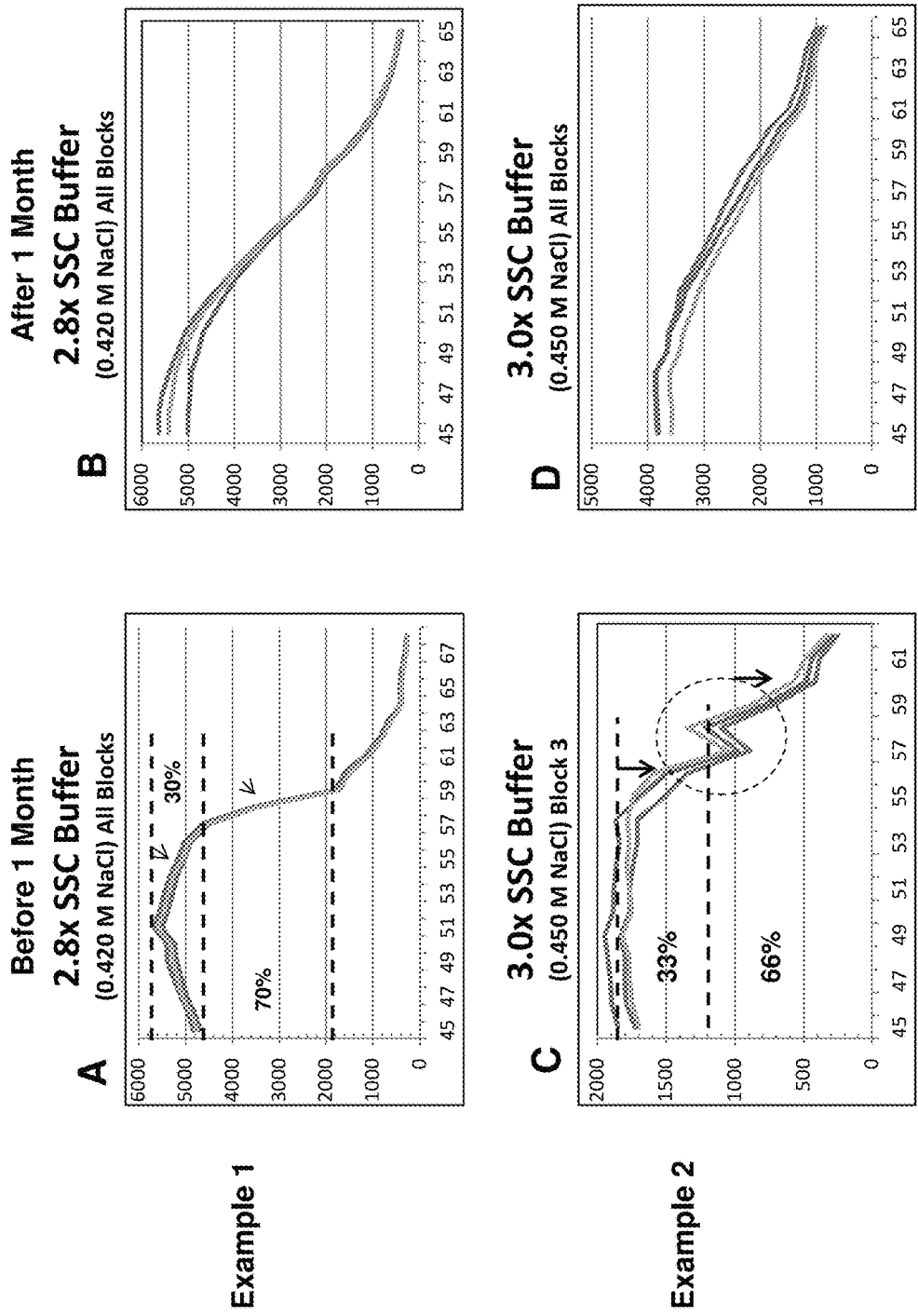
FIG. 16 illustrates stability comparisons of unblocked epoxy slides before and after one month according to an embodiment of the present invention.

In accordance with the present invention, the positive charge needs to be in an appropriate range in order to work—neither too strong nor too weak. No defined amount of chemical charge has been determined but it was clear from experimentation that enhancement of the melting curves was optimal at certain surface chemical concentrations. Furthermore, the chemical composition of the buffer surrounding the nucleic acids can play a role in helping to regulate the effect of the positive charge on the DNA. Preferably, a buffer with a high concentration of ions was thought to shield the nucleic acids somewhat from the attractive force of the positively charged surface reducing the effective attractive force. More preferably, altering the concentration of ions in solution is another way to fine tune the amount of surface attraction the DNA experiences towards the positively charged surface. Another issue that was noted was an inconsistency of the epoxy microarrays in their ability to generate 2 stepped curves. It was speculated that the epoxy surface may react with chemicals in the air causing the surface to become chemically altered and that this effect took place after several days of exposure to the open air (FIG. 16).

In yet another aspect of the present invention, preferably, the solid support (i.e. micro array surface) is surface bound to the DNA as opposed to a flexible linker bound probe DNA. For example, when the solid surface is amine coated, the probe DNA is attached to the solid support by binding positively charged amine surface coating via its negatively charged phosphate backbone. This preliminary bonding is known to those skilled in the art as electrostatic bonding and can be made into a stronger covalent bond by use of heat or uv light (FIG. 10). Typically, the probe molecule is not free to move up and down and cannot contribute to in-homogenous bonding and widening of the melting curve.

In accordance with the present invention, the advantages of using the positively charged microarray surface not only create an enhanced melting curve that can detect the binding and melting of perfectly matched and 1 bp mismatched target, but also create conditions that separate the temperature ranges of melting leading to a temperature of hybridization with maximum levels of specificity for the detection of perfectly matched target DNA without loss of any sensitivity. From hereinafter, this is termed "Charged Enhanced Specificity of Binding" (CESB).

Preferably, charge enhanced specificity of binding can be used to improve the specificity of any hybridization reaction provided the reaction can be done in a solid phase format. A list of methods that would benefit from CESB may include but is not limited to southern blots, northern blots, microarray, PCR and any form of next generation DNA sequencing incorporating a hybridization step. It is well known to those skilled in the art that PCR is one of the most commonly used methods, and the specificity enhancement is the preferred method according to an embodiment of the present invention.

In accordance with the present invention, enhanced melting curves and CESB are provided. Preferably, the enhanced melting curves are due to the additional attractive force the positively charged surface exerts on the DNA. In order for enhancement to occur, the level of positive change preferably must be optimal and the level of ions in the buffer solution must also be optimal. These levels can vary to some degree. Preferably, CESB can create hybridization conditions with maximum specificity and without any loss of sensitivity. More preferably, CESB can occur whenever a positively charged surface is present with the correct ion concentration in the buffer. In a preferred embodiment of the present invention, creating enhanced melting curves and CESB preferably requires a positively charged surface and interplay with the ion concentration of the buffer. Preferably, the consistency of surface charge density of the solid surface is even and consistent. In a preferred embodiment in accordance with the present invention, not only must quality control levels be higher than other applications such as classic microarrays, but special handling and packaging methods may be needed to preserve the surface chemistry.

In accordance with yet another preferred embodiment of the present invention, a novel method in cancer diagnostic assay for KRAS mutations has been developed and is provided. Typically, this assay comprises 12 different mutations occurring within 6 base pairs. Preferably, this test can be performed by melting curve analysis or by CESB during hybridization, according to the methods disclosed in the present invention.

In yet another embodiment of the present invention, CESB and enhanced melting curves can be performed in the liquid phase with special adaptations that allow a miniature solid surface with positive charge to be attached to a probe or primer. This allows liquid phase methods like PCR to benefit from CESB.

According to a preferred embodiment of the present invention, the following issues were addressed and disclosed: 1) determining what is causing the inconsistencies in the ability of the expoxysilane sides to produce 2 stepped melting curves, 2) examining the effect of the ion concentration on the shape of the melting curves, 3) refining a model of how the positive charge enhances the melting curves, 4) using the enhanced melting curves to create a molecular diagnostic test, and 5) proposing future applications for the technology.

In an embodiment of the present invention, a novel cost-effective method to detect the melting of different sequences of target DNA with one base pair sensitivity for each probe spot of a microarray, is disclosed, and represents a powerful genomic analysis tool with the ability to perform a type of DNA sequence determination or low resolution sequencing at the same cost as a microarray. When used in this format, it functions as more than just a microarray, as it allows for the quick and efficient scanning of the entire genome for the few very important genetic differences that exist between samples. Afterwards, if a more detailed analysis is needed, NGS could be performed on the same DNA sample that was hybridized and then selected when melted off the microarray chip. This novel method and application, for example, would be ideal for rapid screening of a population for genetic differences at a much lower cost than sequencing the entire genome. It is known to those skilled in the art, that single nucleotide polymorphisms typically are detected by sequencing DNA first before rapid low cost screening tests are developed to detect known SNPs. Therefore, SNP detection would be limiting to the population already sequenced. Screening with a melting curve microarray would reduce costs so low the entire population could be screened and in theory detect all SNPs in the population. Another application might be tracking the progress of an infectious disease outbreak or biological weapons attack. In this scenario, a large number of infected patients might be screened to allow characterization of virulence factors, drug resistance, or just obtain epidemiologic information about how the outbreaks progress. NGS is a shot gun approach providing global information from which specific information can be gleaned and is not practically cheap enough to sequence entire populations. Melting curve microarray screening in turn can focus in on only producing the relevant genomic information needed, saving time, energy and cost.

The present invention provides for technology related to surface chemistry of the array that produces enhanced melting curves. Additional research involves identifying improvements in the chemical coating of the microarray slide with the aim of yielding more durable, sensitive, and consistent results. Additionally, the stringency of the hybridization/melting process needs to be documented. The eluted target DNA from each microarray should be sequenced via NGS to confirm exactly what bound the probe DNA and exactly what is being melted away at given temperatures. Confirmatory testing would facilitate developing specific applications.

Accordingly, the developed method of the present invention serves to identify one base pair differences between different types of target DNA bound to a single probe spot. This has been accomplished on microarray slides containing 600-800 probe spots. An initial attempt to perform this analysis on commercial microarray chips containing over 30,000 probe spots was made but failed for reasons likely related to labeling of the target DNA and not the actual melting analysis. During initial development simplicity of array target density and composition was chosen to avoid any difficulty with interpretation of results. As such, custom microarray slides with 1000 or more probe spots were not ordered. However, it is likely that this technique will work on slides containing a minimum of 1000 probe spots provided the spots were large enough in diameter (>150 µM). It is expected that further development in ability to control the surface chemistry of the slides will help in other applications of the method, such as the characterization of tuberculosis isolates.

According to the present invention, the technology bridges the gap between microarray and Next Generation Sequencing (NGS and can achieve the accuracy of NGS systems at microarray prices. This technology competes with microarrays but can work with or compete against NGS depending on the application. Preferably, the technology can be used as a capture/enrichment platform, and can more specifically and efficiently capture target DNA than conventional microarray capture systems. More preferably, this technology elutes nonspecific and extraneous DNA at low melting temperatures while retaining stably bound desired target DNA. For NGS, this can increase the efficacy of enrichment while reducing NGS sequencing cost by avoiding the sequencing of unwanted DNA. Additionally, because actual sequencing data can also be obtained by melting curves analysis on the array, the technology can simultaneously capture and re-sequence DNA by association, thereby obviating NGS sequencing.

In a most preferred embodiment of the present invention, disclosed are novel assays to consistently resolve one base pair differences between different types of target DNA in a complex mixture. Typically, these results are unlikely to be accomplished under standard microarray, standard PCR, or variations of PCR such as allele specific PCR. In a preferred embodiment of the present invention, real application of melting curve analysis in a microarray format with a positively charged surface to a diagnostic assay. Previously, there have been challenges to overcome resolving one base pair differences between different types of DNA in a complex mixture. The first challenge is that a 2 base pair mismatch is unlikely to bind under the current hybridization conditions. The second challenge is that typically, assays are unable to differentiate different KRAS activation mutants if the mutation is in the exact same base pair position. The optimal way to clarify this result is to use probes specific for the possible mutations. However, this was resolved in accordance with a method of the present invention with the KRAS assay using C6 wild type and S1 mutant probes. It is known to those skilled in the art, that it may not be possible to obtain by standard methods. Previous techniques typically have known to be unreliable and unable to consistently resolve one base pair differences between different types of target DNA in a complex mixture.

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

EXPERIMENTAL

Experiments with ARRAYIT Check it Chips

Initial experiments utilized a commercial microarray chip "Check It Chips" with large 300 µM probe spots and 70 mer probe sequences for the human genome printed in blocks of 100 spots for a total of 2 blocks or 200 probe spots per array (commercially available from ARRAYIT Corporation, Sunnyvale, Calif.). According to the present invention, these slides typically have an amine coated surface which is positively charged and attracts the negatively charged nucleic acid probes. The probes are then covalently bonded to the amine surface by UV cross linking. In order to neutralize the positively charged amine coated surface after probe attachment and before hybridization of the target, a blocking agent typically is used. The Check It Chips microarray kit did not come with blocking agent, no blocking was performed, and the surface of the array was assumed to be positively charged. Human cDNA stained with CY3 dye (ARRAYIT Corp.) was used as target DNA for hybridization. Typically, melting experiments can be carried out in a temperature range from about 0° C. to about 100° C. Preferably, melting experiments were carried out over a temperature range from about 40° C. to about 70° C., preferably with temperature increase increments of 1° C. and fluidics buffer flush of 600 µl of 2.5×SSC buffer. Alternatively, a 10% solution of 2-Mercaptoethanol in 2.5× SSC buffer (0.375M NaCl) was made and used as the melting/flush buffer to reduce photobleaching of the CY3 dye. This solution was made by diluting a stock 20× concentration of SSC with a combination of distilled water and a stock concentration of 2-Mercaptoethanol in order to make a 10% solution of 2-Mercaptoethanol in 2.5×SSC buffer.

Fabrication of Custom Microarray Chips

The hybridization, washing and melting cycles of the melting curve microarray, according to an embodiment of the present invention, requires a strong and durable covalent attachment of probe molecules to ensure repeatability between assays. The epoxysilane coated microarray slides Nexterion Slide E (Schott, Louisville, Ky.) were selected as a most durable product to attach the probes. Probe DNA sequences were 25 base pairs in length (bp) and contained a modified amino 5' terminus containing a 6 amino acid linker. All probe sequences were custom synthesized by IDT (Coralville, Iowa). Slides were professionally printed using a Nexterion Slide E protocol by two different vendors, the Functional Genomics Lab of University of Illinois (Urbana-Champaign, Ill.) and Microarray Inc. (Huntsville, Ala.). Microarrays were fabricated using standard pin printing techniques known to those skilled in the art, producing 150 µM diameter probe spots. However, chemical deactivation with ethanolamine of unreacted epoxy groups after printing was not performed on the first batch of slides from the Functional Genomics Lab and the slides were shipped with an unblocked reactive surface. Subsequent epoxy microarrays were order from Microarray Inc. in both ethanolamine deactivated surfaces and non-deactivated surfaces.

Probe Sequences and Microarray Layout

Microarrays were fabricated with between 6-8 repeating blocks down the array slide with approximately 100 probes spots per block. The general layout is summarized in Table 1. The first row of each block contained a set of control probe spots. These consisted of positive control spots affixed with CY3 dye which ranged in concentration from 5 µM to 20 µM, blank space(s), an *E. coli* gene as a negative control, and the gene sequence of interest, mouse GAPDH, in antisense orientation. The mouse GAPDH probe spot was repeated in sense orientation between rows 1-10.

TABLE 1

Probe Spot Layout for Custom Arrays

| Row | Col | Gene | Orientation and Sequence |
|---|---|---|---|
| 1 | 1 | Cy3 Dye Control *E. coli* Ecs2686 Flagellar Biosynthesis Gene 20 µM | 5'-TCT TAT TCA GCC TGA CTG GTG GGA A-3'-CY-3 SEQ ID NO: 1 |
|  | 2 | Cy3 Dye Control *E. coli* Ecs2686 Flagellar Biosynthesis Gene 10 µM | 5'-TCT TAT TCA GCC TGA CTG GTG GGA A-3'-CY-3 SEQ ID NO: 1 |
|  | 3 | Cy3 Dye Control *E. coli* Ecs2686 Flagellar Biosynthesis Gene 5 µM | 5'-TCT TAT TCA GCC TGA CTG GTG GGA A-3'-CY-3 SEQ ID NO: 1 |
|  | 4 | Blank | Blank |
|  | 5 | *E. coli* Ecs2686 Flagellar Biosynthesis Gene | Sense 5'-TCT TAT TCA GCC TGA CTG GTG GGA A-3' SEQ ID NO: 1 |
|  | 6 | Mouse GAPDH Gene Antisense Control | Antisense 5'-TGA CAA TCT TGA GTG AGT TGT CAT A-3' SEQ ID NO: 2 |
|  | 7-10 | Mouse GAPDH Gene | Sense 5'-TAT GAC AAC TCA CTC AAG ATT GTC A-3' SEQ ID NO: 3 |
| 2-10 | 1-10 | Mouse GAPDH Gene | Sense 5'-TAT GAC AAC TCA CTC AAG ATT GTC A-3' SEQ ID NO: 3 |

Target DNA Sequences

Target DNA consisting of 25 mer synthesized oligos (IDT) with CY3 dye modifications added to the 5' terminus are shown in Table 2. A one base pair mismatch or SNP was added to the targeted DNA at position 13 causing a G to A mutation.

TABLE 2

List of Target Sequences

| Oligo/Orientation | Sequence |
| --- | --- |
| Mouse GAPDH Gene Antisense Perfect Match | 5'-TGA CAA TCT TGA GTG AGT TGT CAT A-3' SEQ ID NO: 2 |
| Mouse GAPDH Gene Antisense One bp Mismatch | 5'-TGA CAA TCT TGA ATG AGT TGT CAT A-3' SEQ ID NO: 4 |

Fabrication of Custom Microarray Chips for KRAS (V-Ki-Ras2 Kirsten Rat Sarcoma Viral Oncogene Homolog) Analysis The epoxysilane coated microarray slides Nexterion Slide E (Schott, Louisville, Ky.) were used. Probe DNA sequences were 25 base pairs in length (bp) and contained a modified amino 5' terminus containing a 6 amino acid linker. All probe sequences were custom synthesized by IDT (Coralville, Iowa) and in sense orientation. Slides were professionally printed using a Nexterion Slide E protocol by Microarray Inc. (Huntsville, Ala.). Each probe spot block consisted of 21 probe spots in a layout of 10 blocks. The probe spot layout and probe sequences of each block are shown in Table 3. A batch of 100 slides was fabricated using standard pin printing techniques known to those skilled in the art, producing 150 μM diameter probe spots. However, chemical deactivation with ethanolamine of unreacted epoxy groups after printing was not performed and the slides shipped with a reactive surface.

TABLE 3

KRAS Probes for Codons 12 and 13 (Sense Orientation) and Probe Spot Block Layout for KRAS Arrays (Mutated bases in bold font).

| Row | Col | Code | Gene/Mutation | Sequence |
| --- | --- | --- | --- | --- |
| 1 | 1 | C1 | Dye Control: Cy3 Dye attached to *E. coli* sequence Ecs2686 Flagellar Biosynthesis Gene, at 20 uM concentration | 5'-TCT TAT TCA GCC TGA CTG GTG GGA A-CY-3' SEQ ID NO.: 1 |
| 1 | 2 | C2 | Dye Control: Cy3 at 10 uM conc. | 5'-TCT TAT TCA GCC TGA CTG GTG GGA A-CY-3' SEQ ID NO.: 1 |
| 1 | 3 | C3 | Dye Control: Cy3 at 5 uM conc. | 5'-TCT TAT TCA GCC TGA CTG GTG GGA A-CY-3' SEQ ID NO.: 1 |
| 1 | 4 | C4 | Negative Control: Blank Space | None |
| 1 | 5 | C5 | Negative Control: *E. coli* sequence Ecs2686 Flagellar Biosynthesis Gene | 5'-TCT TAT TCA GCC TGA CTG GTG GGA A-3' SEQ ID NO.: 1 |
| 2 | 1 | C6 | Positive Control: KRAS Wild Type | 5'-GTT GGA GCT GGT GGC GTA GGC AAG A-3' SEQ ID NO.: 5 |
| 2 | 2 | S1 | Mutation: Gly12Ser (GGT > AGT) | 5'-GTT GGA GCT AGT GGC GTA GGC AAG A-3' SEQ ID NO.: 6 |
| 2 | 3 | S2 | Mutation: Gly12Arg (GGT > CGT) | 5'-GTT GGA GCT CGT GGC GTA GGC AAG A-3' SEQ ID NO.: 7 |
| 2 | 4 | S3 | Mutation: Gly12Cys (GGT > TGT) | 5'-GTT GGA GCT TGT GGC GTA GGC AAG A-3' SEQ ID NO.: 8 |
| 2 | 5 | S4 | Mutation: Gly12Asp (GGT > GAT) | 5'-GTT GGA GCT GAT GGC GTA GGC AAG A-3' SEQ ID NO.: 9 |
| 3 | 1 | S5 | Mutation: Gly12Ala (GGT > GCT) | 5'-GTT GGA GCT GCT GGC GTA GGC AAG A-3' SEQ ID NO.: 10 |
| 3 | 2 | S6 | Mutation: Gly12Val (GGT > GTT) | 5'-GTT GGA GCT GTT GGC GTA GGC AAG A-3' SEQ ID NO.: 11 |
| 3 | 3 | S7 | Mutation: Gly13Ser (GGC > AGC) | 5'-GTT GGA GCT GGT AGC GTA GGC AAG A-3' SEQ ID NO.: 12 |

TABLE 3-continued

KRAS Probes for Codons 12 and 13 (Sense Orientation) and Probe Spot Block
Layout for KRAS Arrays (Mutated bases in bold font).

| Row | Col | Code | Gene/Mutation | Sequence |
|---|---|---|---|---|
| 3 | 4 | S8 | Mutation: Gly13Arg (GGC > CGC) | 5'-GTT GGA GCT GGT CGC GTA GGC AAG A-3'<br>SEQ ID NO.: 13 |
| 3 | 5 | S9 | Mutation: Gly13Cys (GGC > TGC) | 5'-GTT GGA GCT GGT TGC GTA GGC AAG A-3'<br>SEQ ID NO.: 14 |
| 4 | 1 | S10 | Mutation: Gly13Asp (GGC > GAC) | 5'-GTT GGA GCT GGT GAC GTA GGC AAG A-3'<br>SEQ ID NO.: 15 |
| 4 | 2 | S11 | Mutation: Gly13Ala (GGC > GCC) | 5'-GTT GGA GCT GGT GCC GTA GGC AAG A-3'<br>SEQ ID NO.: 16 |
| 4 | 3 | S12 | Mutation: Gly13Val (GGC > GTC) | 5'-GTT GGA GCT GGT GTC GTA GGC AAG A-3'<br>SEQ ID NO.: 17 |
| 4 | 4 | C7 | Dye Control: Cy5 Dye attached to *E. coli* sequence Ecs2686 Flagellar Biosynthesis Gene, at 20 uM concentration | 5'-TCT TAT TCA GCC TGA CTG GTG GGA A-CY-5<br>SEQ ID NO.: 1 |
| 4 | 5 | C8 | Dye Control: Cy5 at 10 uM | 5'-TCT TAT TCA GCC TGA CTG GTG GGA A-CY-5<br>SEQ ID NO.: 1 |
| 5 | 1 | C9 | Dye Control: Cy5 at 5 uM | 5'-TCT TAT TCA GCC TGA CTG GTG GGA A-CY-5<br>SEQ ID NO.: 1 |

Target KRAS DNA Sequences

Target KRAS DNA consisting of 25 mer synthesized oligos (IDT) with CY3 dye modifications added to the 5' terminus are shown in Table 4. Mutations in bold font.

TABLE 4

List of KRAS Target Sequences

| Oligo/Orientation | Sequence |
|---|---|
| KRAS Wild Type Antisense | 5'-5Cy3/TCT TGC CTA CGC CAC CAG CTC CAA C-3'<br>SEQ ID NO.: 18 |
| KRAS S1 Mutation Antisense | 5'-5Cy3/TCT TGC CTA CGC CAC TAG CTC CAA C-3'<br>SEQ ID NO.: 19 |

Hybridization of Microarray Chips

Before hybridization was started a pre-hybridization wash of printed microarrays was performed using Nexterion E Pre-Hyb solution (Schott AG) according to the manufacturer's instructions. Briefly, microarray slides were transferred to clean Coplin jars containing solution preheated at 42° C. for approximately 10 minutes. Pre-hybridized slides were then washed with distilled water (dH2O) for 30 seconds and this process was repeated up to five times until no foaming appeared in the solution. Slides were then washed in 2-propanol for 2 minutes and quickly air dried before hybridization.

A 100 μl hybridization mixture was made from 76 μl hybridization buffer with formamide (ARRAYIT HybIt® 2, ARRAYIT Corp.), 16 μl dH2O, and 8 μl of target DNA at 250 μM concentration. If the target sample consisted of a mixture of 50% perfect match and 50% 1 bp mismatch, then 4 μl of each was combined. Between 33 μl to 50 μL of hybridization mixture was applied to each slide before placing a cover slip over the sample. Microarrays were placed in hybridization chambers (ARRAYIT, Corp.) and incubated at 45° C. for 16-24 hours with mild agitation via a rotating shaker in a hybridization oven without humidification.

Alternatively, if a polyethyleneimine (PEI) coating was placed over the epoxy coated slides, a variation of the pre-hybridization procedure above was followed. The pre-hybridization wash was followed but the 2-propanol wash was omitted. Then the surface of the slides was incubated at room temperature with concentrations of branched PEI diluted in 2.5×SSC buffer that ranged from 1% to 10% PEI for 20 min. The slides were washed 3× with 2.5×SSC buffer and then hybridization was followed exactly as described above.

Post Hybridization Processing

Nexterion E Post Hyb wash solutions of low, medium, and high stringency were used (Schott AG). A Coplin dish was filled with low stringency buffer pre-warmed to 45° C., slides were submerged for 5 minutes, allowing the cover slip to become detached within 30 seconds of being submerged. Subsequently the slides were incubated for 5 minutes each in a series of room temperature buffers consisting of 2 successive washes in medium stringency buffer and 2 successive washes in high stringency buffers. Then, slides were rinsed several times in a dish containing dH2O.

Washed slides were carefully and quickly placed (DNA probe spots facing down) into Custom cassettes of the present invention containing 450 μl of SSC buffer which would be the same concentration of the melting phase of the experiment and ranged in concentration from 2.0×4.0× so as not to allow the slides to dry out. The window of the cassette was made from cover slip glass and alternatively optical grade plastic (Grace-Bio Labs, Bend, Oreg.). The cassettes were sealed with water tight and heat resistant tape (Grace-Bio Labs) and completely filled with SSC buffer which was the same concentration of the melting phase of the experiment using a micropipette inserted into the in-port of the cassette, being careful to avoid leaving any air space or air bubbles in the cassette.

Melting Assay and Data Processing

A modified Axon 4000a microarray scanner according to the present invention, operated using custom software that interfaced the existing GENEPIX software included with the Axon reader. Before starting each experiment, the plumbing system was flushed with 2.5×SSC buffer, the thermal control chamber was pre warmed to 44° C., and the scanner focused. The general programmed parameters for the experiment called for successive temperature incubations and washes over a range of 40° C. to 70° C. with temperature increase increments of 1° C., a temperature hold time of 1 minute, and a 2.5×SSC buffer flush of 600 μl. A scan was then made at 532 nm with starting PMT settings ranging between 600-700 and scan files saved to the hard drive of the computer. As the experiment progressed, after each temperature increase there was an automatic PMT increase of 3 units followed by an automatic focus adjustment increment. These cycles were continued until the last temperature was reached for the range of the experiment.

For each 1° C. increment of temperature change during the experiment a scan file was produced. Typical experiments generated over 20 scan files. Each scan was analyzed using the GENEPIX software according to the manufacturer's instructions. Briefly, for the first scan at a temperature of 40° C., the file was analyzed with the microarray manufacturers GAL file and GENEPIX software with a fixed surface area of the spot circle. Once the first scan was analyzed, a GPS file was generated by the GENEPIX software. The GPS file contained the software parameters used for analysis of the first scan. In order to ensure consistency of data analysis, the same GPS file was used to analyze all remaining scans from the experiment.

The resulting scan file produced for each 1° C. increment of temperature contained all the statistical data in a GENEPIX software spreadsheet format termed a GPR file. For each GPR file the column containing the Mean F532-B532 (Mean Fluorescence 532-Background 532) was copied and transferred to a MICROSOFT EXCEL software spread sheet. This procedure may be computed by hand but data compiling software was written to automate the task. All graphs were generated with the EXCEL software program.

Processing of PHALANX ONEARRAY Whole Human Genome Chips

Human cDNA samples consisting of CY3 or CY5 dye labeled liver cDNA and heart cDNA samples were obtained from Dr. Chad Walton at the University of Hawaii and were prepared using standard methodologies. These samples were hybridized and processed using the HUMAN ONEARRAY microarrays from PHALANX (Palo Alto, Calif.) in accordance with the manufacturer's protocol.

Summary of Results:

Improvements to the Microarray Scanner

Figure 2:
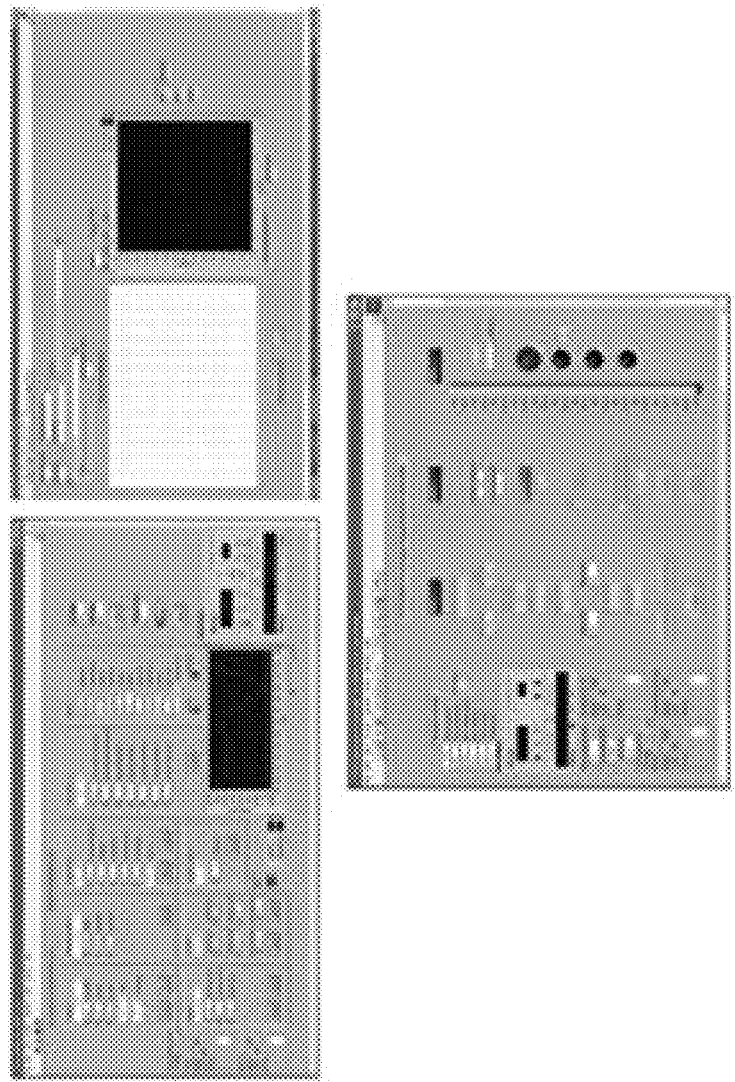
FIG. 2 illustrates screenshots of three custom software programs, according to embodiments of the present invention.
Figure 8B:
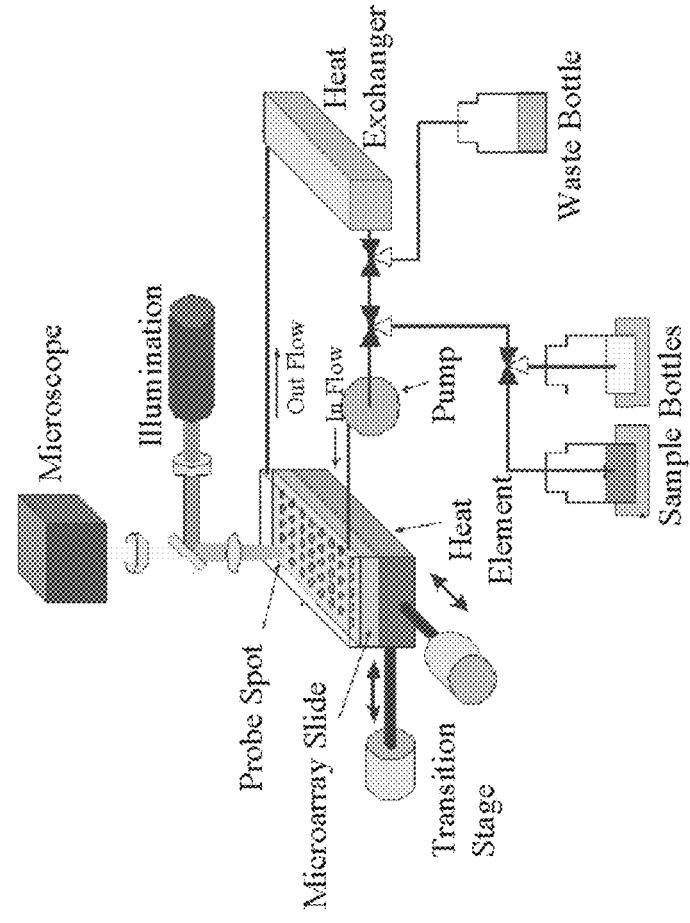
FIG. 8B illustrates the thermal control chamber and heating block of the modified microarray scanner, according to the embodiments of the present invention.
Figure 9B:
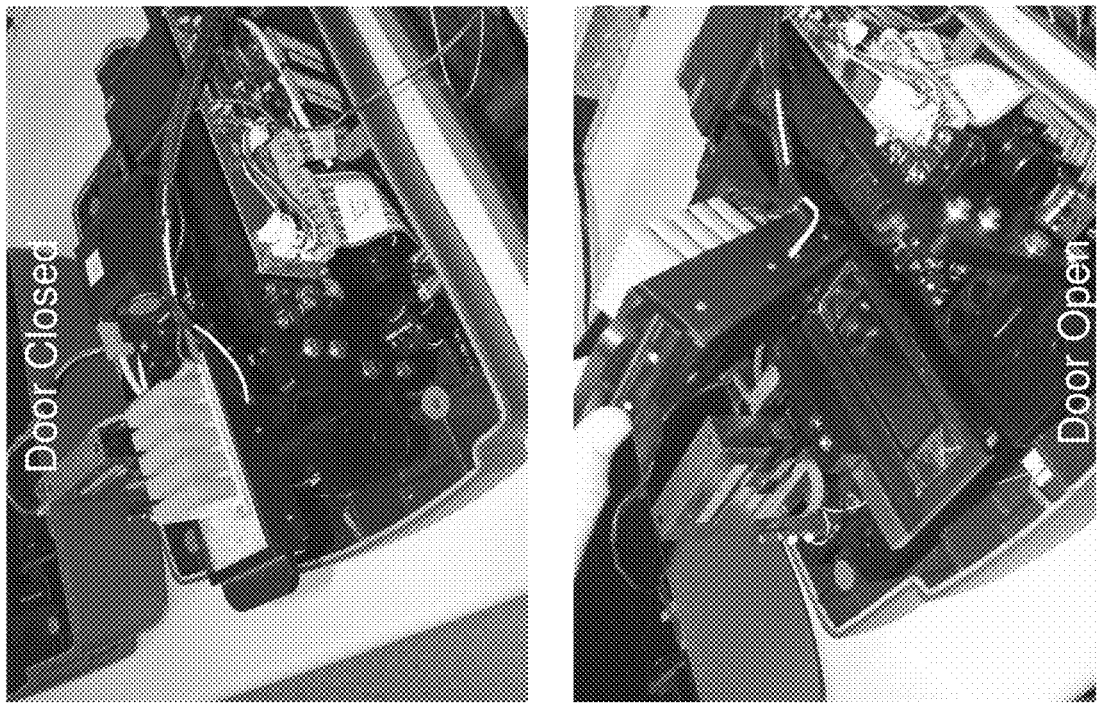
FIG. 9B illustrates the microarray installed in the modified microarray scanner of FIG. 8B according to an embodiment of the present invention.
Figure 9A:
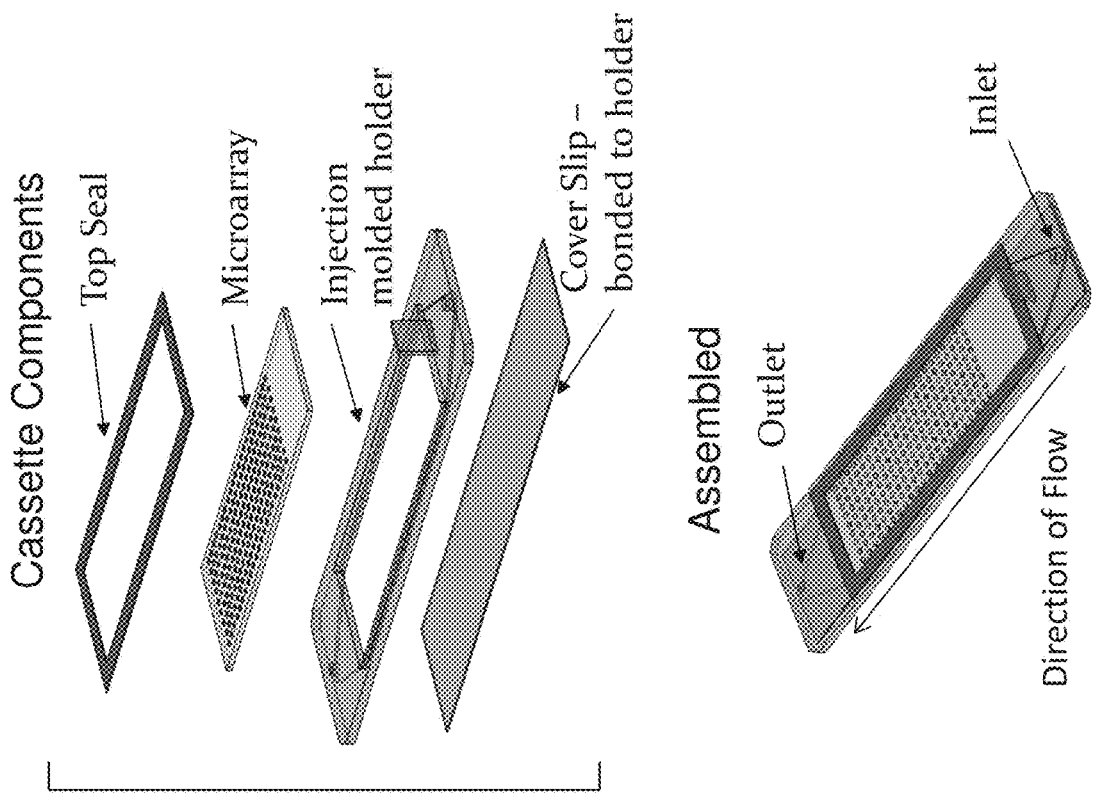
FIG. 9A illustrates the redesigned array cassette of the modified microarray scanner of FIG. 9B according to an embodiment of the present invention.

According to an embodiment of the present invention, there is provided an improved microarray reader, including a redesigned cassette port (FIG. 8B) and cassette (FIG. 9A). The flow and heating characteristics of the device are improved making use and loading of the machine easier. FIG. 9B shows a loaded cassette in place with the objective lens of the reader below the cassette. Three novel software programs were written to operate the machine and help analyze the data (FIG. 2). Furthermore, computerized Z-axis was added to the thermal control block to speed up the focusing procedure and allow automatic incremental adjustments of focus during experiments (figure not shown).

Analysis of Custom Microarray Chips Produced by the W. M. Keck Center for Comparative and Functional Genomics Aside from control probe spots, the microarray chips produced by the Keck Center at University of Illinois at Urbana-Champaign were, composed entirely of probes to detect the binding of the mouse GAPDH gene sequence. GAPDH is a housekeeping gene that is normally expressed at high levels within mouse cells because of its involvement with glycolysis. Eight blocks or about 800, 150 μM probe spots were replicated on a microarray slide. Duplicate blocks allowed verification of the consistency of results and the large probe spots made scanning detection easier. Arrays were hybridized with excess of target DNA which contained a complementary 25 mer labeled with CY3 dye.

Figure 3:
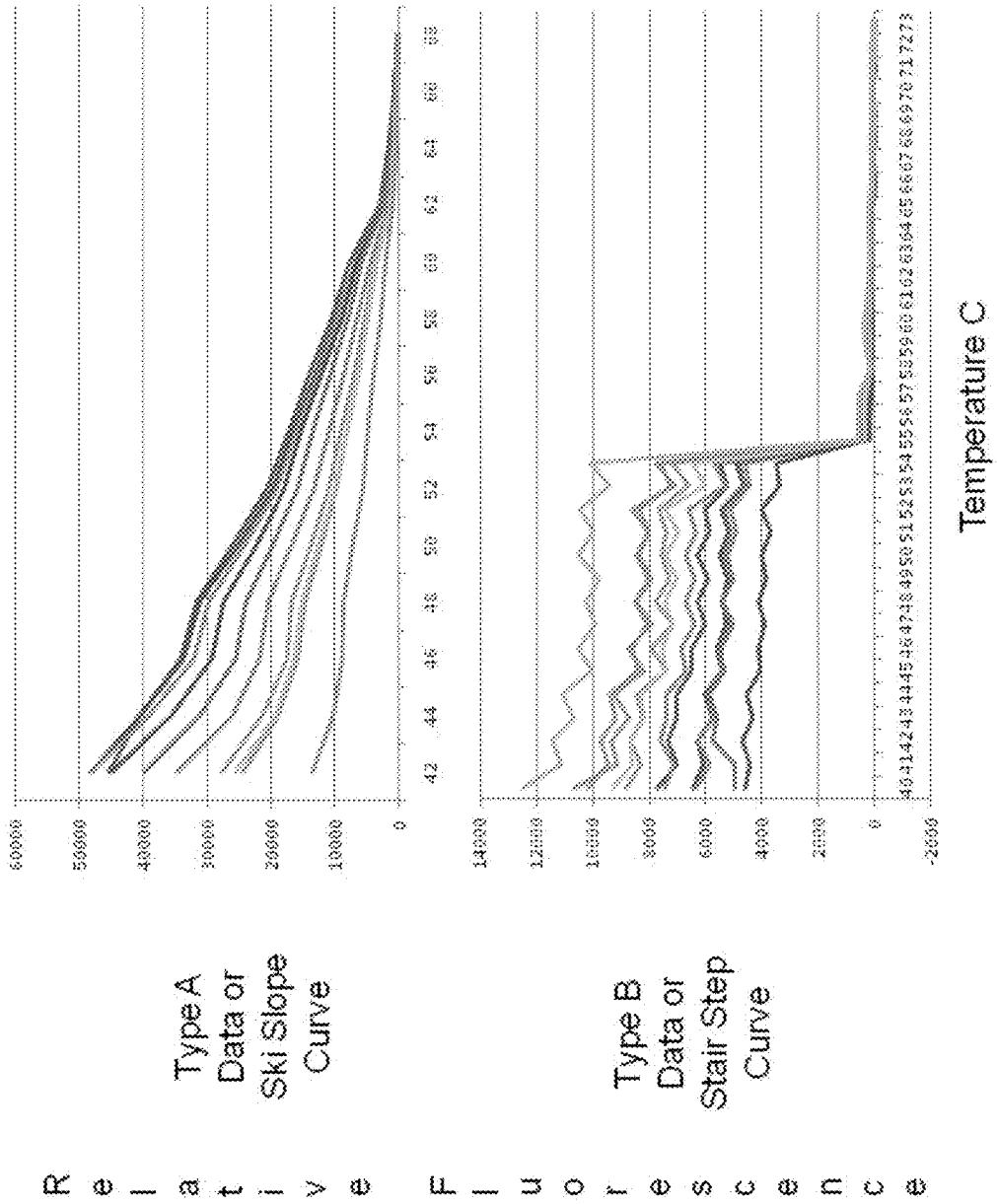
FIG. 3 illustrates a comparison of the initial results obtained with the Keck Center Microarray Chips according to the present invention. A total of 10 probe spots are displayed in each graph. All data is raw and unadjusted.

Unexpected results for the array system of the present invention were achieved after starting experiments with the Keck Center microarray chips. Two very different types of data were obtained with these chips and are shown in FIG. 3. The very first chip analyzed produced a ski slope curve or type A data which represented a gentle downward slope until nearly all of the probe was melted from the chip, in the mid to high 60° C. range. This is unprocessed or raw data without adjustment. A casual inspection of the curve does not reveal a prominent melting point, which would be indicated by a steep downward drop. Rather a shallow downward curve is present ranging from 42° to 68° C. As such it is not possible to determine a specific Tm for the bound target DNA. It appears to melt off over a range of greater than 20° C. Note that all 10 probe spots displayed in the graph follow about the same shape of melting curve showing consistency of results. Furthermore, these results were representative of the data obtained from all 8 blocks on the chip. The second chip analyzed in the same experiment under identical conditions produced a stair step or type B curve. The type B data produced a very steep drop-off melting curve. Completely melting off over less than 2.5° C. with a Tm at approximately 55° C. All 10 probe spots in the graph started at different intensities indicating that different concentrations of target bound, but all target melted at exactly the same temperature, showing consistency of results. This data is representative of the 8 blocks on the chip.

As two very different types of curves were generated under identical conditions, experiments were repeated until all chips from the Keck Center were used. As experiments progressed these two distinctly different types of graphs were generated repeatedly with the type A data being about 5 times more common than the type B data. The type B or stair step type data is more preferable since the Tm is easily calculated. Moreover, type B data from the Keck Center chips was also similar to data obtained using commercially made microarray chips (ARRAYIT Corp., see FIG. 11B). Due to some kind of significant procedural difference occurring in the machine, methodology or reagents, further experimentation was conducted.

Accordingly, an improvement to the focus adjustment of the machine of the present invention was implemented. The focus was controlled by 3 set-screws that made the stock instrument very difficult to adjust. It is noted that an out of focus machine produced unreadable data and if the focus began to drift during an experiment the data ended up being distorted. Additionally, as the focus issue was examined, it was found that during an experiment, as the temperature of the buffer 2.5×SSC buffer increased, the refractive index of the buffer also changed causing the focus to go out of adjustment. To correct this problem, a dynamic focus adjusting system was installed which included adding a z-axis to the thermal control block. Once this component was installed the focus was steady as judged by the positive control CY3 dye labeled probe spots that remained steady in intensity over the entire experiment (data not shown).

Figure 4:
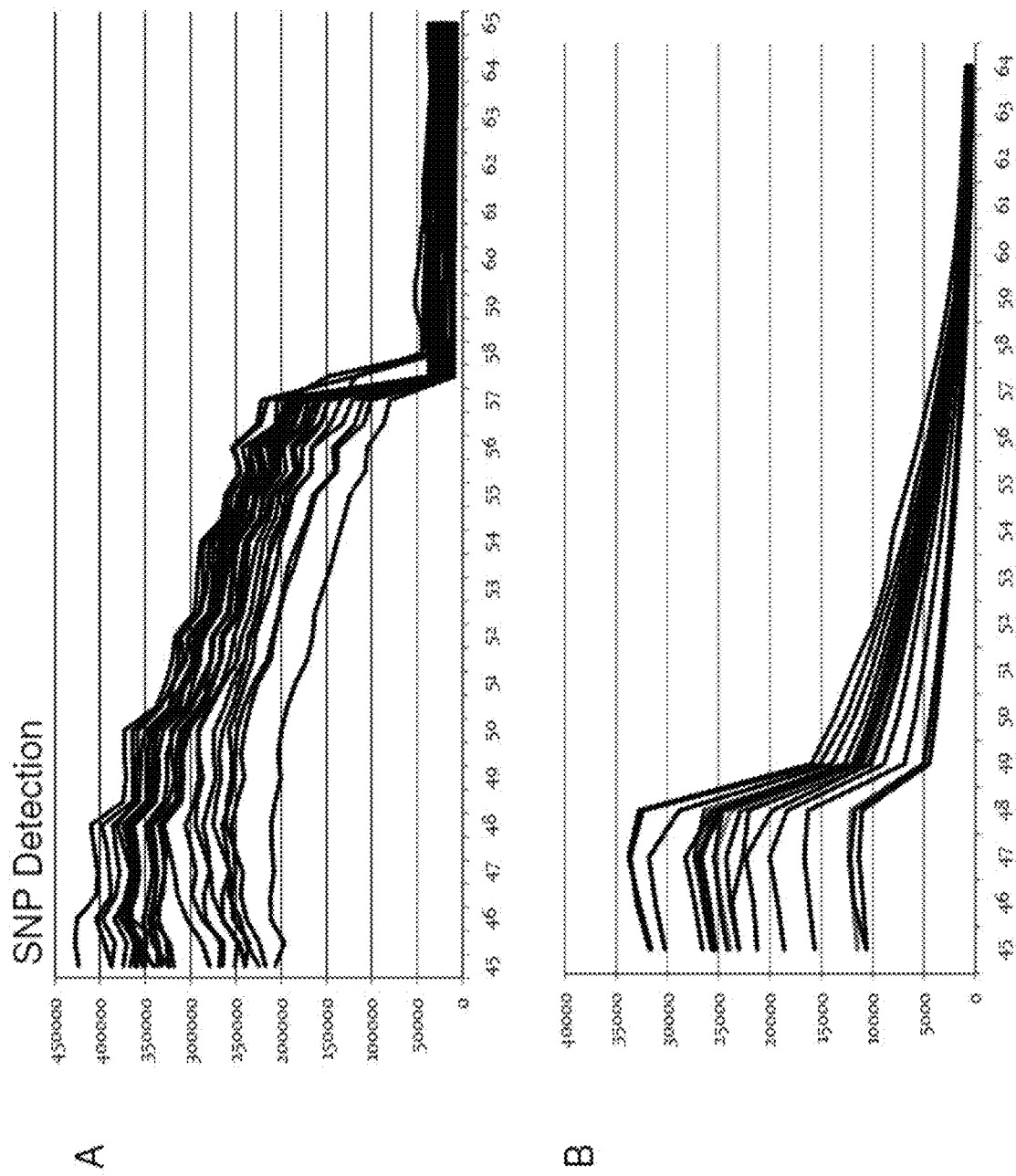
FIG. 4 illustrates a comparison of the melting curves between perfectly matched target and 1 base pair mismatch target binding the 25 mer mouse GAPDH probe sequence according to the present invention. Graph A shows melting curve analysis from a microarray with identical probe spots containing the same 25 mer probe. Note the extremely sharp melting curve and Tm of about 57° C. Graph B is a microarray with the same probe type as graph A but hybridized with target containing a 1 bp mismatch or SNP. Note that the Tm is about 48.5° C. a difference of 8.5° C. compared to graph A.

Further experiment was conducted with remaining Keck Center chips in which the type of target DNA was switched from perfect match to one base pair mismatch or a SNP. All other experimental parameters were the same. Again the type A data was the most common melting curve obtained but some type B data was also observed as shown in FIG. 4. When target DNA containing a one base pair mismatch was used, the measured melting temperature of the target was approximately 48.5° C. or 8.5° C. lower than the perfectly match target (graph A in FIG. 4). The predicted difference in melting temperature using commercially made software for this same reaction under liquid phase conditions was 4.4° C. Therefore, the method of the present invention appeared to both sharpen the melting curve and increase the difference in Tm between perfectly matched and one base pair mismatched targets enhancing detection of SNPs.

Analysis of Custom Microarray Chips Produced by Microarray Inc.

To confirm the results, including the unexplained type A data, or to verify a problem with the Keck Center chips, experiments were conducted on additional chips from another vendor. A set of experiments was conducted with an exact same type of microarray chip and was ordered from Microarray Inc. The best of the results showed sharper, easier to read melting curves with increased separation between perfectly matched and one base pair mismatched target, suggesting good SNP detection. Moreover, data obtained from experimentation as shown in FIG. 11B suggested that the technique was capable of discriminating between different types of target bound to the same probe spot. This is evident in FIG. 11B of the beta actin graph in the two distinct Tm's observed, indicating at least two types of target bound. The experiments using the chips from Microarray Inc. were started using a 50:50 mixture of perfectly matched and one base pair mismatched target DNA both labeled with CY3 dye and hybridized at the same time; the goal of this experiment being to detect the melting of both types target simultaneously on the same probe spot.

Initial experiments using Microarray Inc. chips produced a distinctly different melting curve shape depicted in FIG. 18B. This curve is a classic ski-slope curve with a short plateau at about 43° C. and a downward slope over a range of 44° C. to 64° C. The median Tm might be approximated by the arrow at about 55° C. but the target was composed of two different sequences and should in turn produce two different Tm's. Therefore the Tm for the perfect match and one base pair mismatch was not detected as separate curves but rather blended into one large curve. This result was repeated over several different experiments and is representative data of the 6 blocks printed on the chips. The repeatability of the Microarray Inc. chips was excellent but the sharp steep drop off melting curves that were obtained on the Keck Center chips was not observed.

All results obtained using the Keck Center chips and Microarray Inc. chips were re-evaluated. A key difference in the array fabrication procedure of the sets of chips was then identified. Microarray Inc. performed chemical deactivation of un-reacted epoxy groups with ethanolamine after printing was completed but before shipping to the end user. The Keck Center omitted the deactivation step and shipped the slides with an active surface allowing the end user to perform deactivation if desired. The manufacture of the slides Nexterion Slide E (Schott AG) recommended deactivation with ethanolamine. This prevented unwanted reactions with target DNA other than hydrogen bonds or background substances with the surface epoxide, which may include ozone or airborne hydrocarbons that would produce abnormal signal and distort the results.

This information allowed for interpretation of the results from both the Keck Center and Microarray Inc. slides. The Keck Center slides may have bound target via bonds other than hydrogen bonds or had the capacity to react with abundant levels of ozone and hydrocarbons present in the tropical air of developed areas of Hawaii and certainly present in the room air of the laboratory. The type A curve may possibly be related to the reaction of the chip surface with unwanted agents in the air causing background and unreadable results. Also, it may be possible that the type B results were attained if the chips were processed very quickly and placed in liquid buffer without allowing the room to air to react with the surface.

However, the surface chemistry of the Keck Center and Microarray chips was distinctly different. The active surface of the Keck Center chips contained an epoxide exposed to the surface. The epoxide was intended to react with the amino terminus of the modified probed DNA via a nucleophilic addition where the epoxide functions as an electrophile and the probe molecule as a nucleophile. Since the epoxide is un-reacted, the surface is coated with a strong electrophile, which generally can have a positive chemical charge. The deactivation of epoxide with ethanolamine via a nucleophilic addition changes the surface composition of the slide from epoxide to that of a hydrocarbon with attached hydroxyl group.

Figure 18:
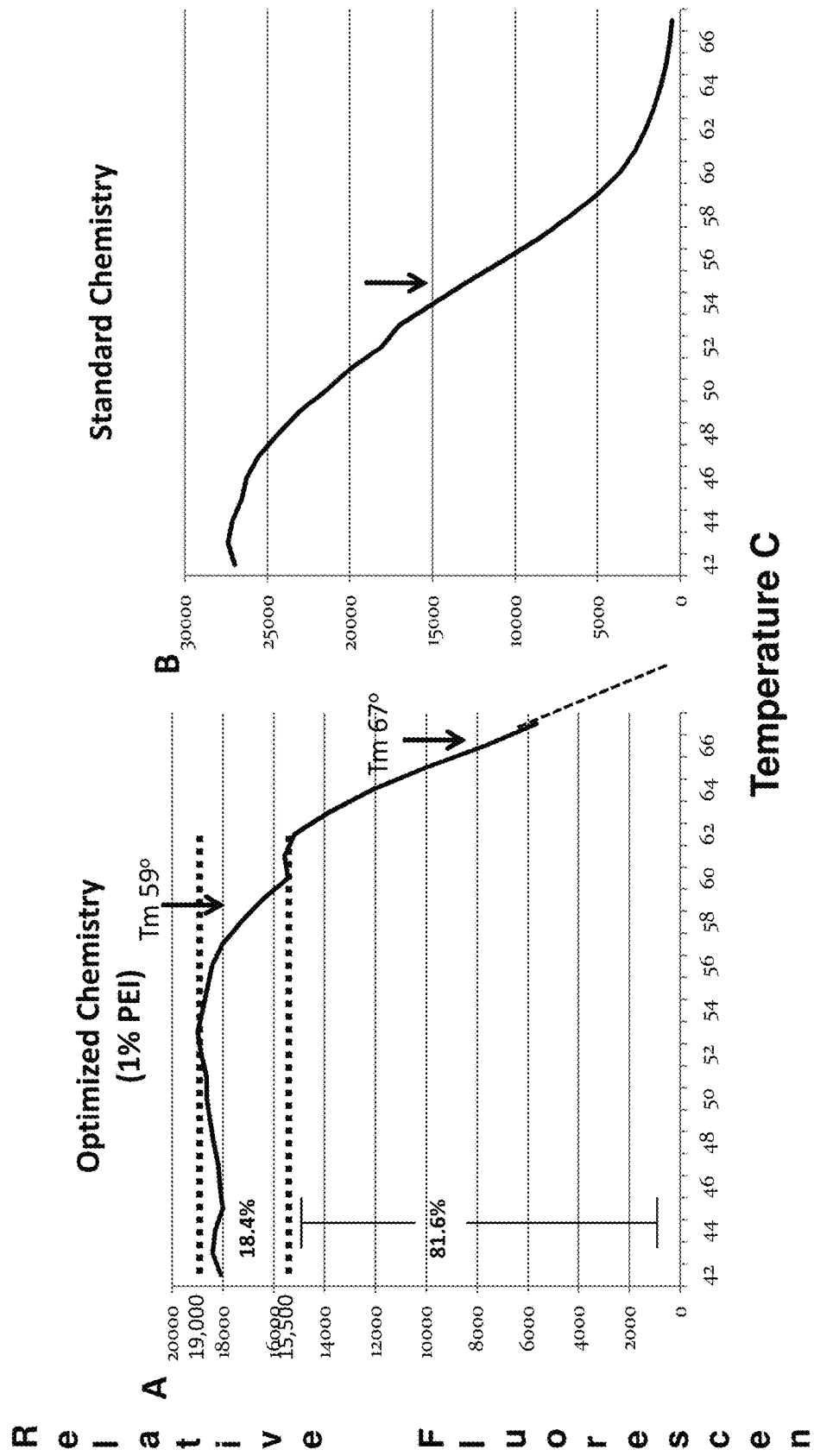
FIG. 18 illustrates an exemplary comparison of the type of melting curves obtained using standard and optimized surface chemistry of Microarray Inc. arrays according to the present invention. Graph A is a melting curve on an array with optimized surface chemistry which is able to detect that approximately 18% of the target bound on this spot is one base pair mismatch (Tm 59° C.) and about 82% perfect match (Tm 67° C.). Graph B is a melting curve on an array with standard surface chemistry and is unable to detect two distinct types of target and instead shows one large melting curve with a Tm of about 55° C. Note that the slope of graph A is steeper and that melting is occurring at a higher temperature.

As shown in FIG. 18, a comparison of the different melting curves obtained between the type B curves (FIGS. 3 and 4) from the Keck Center chips and the Microarray Inc chips (FIG. 18, graph B) suggest that the different chemical characteristics of the active and deactivated chip surface were causing different shaped melting curves. It is possible that the positively charged surface of the active epoxide was in some way reacting with the bound target DNA and that under specific conditions of increasing temperature and flow, could cause the dsDNA to melt apart with a much sharper curve. This then increased the difference in Tm between perfect match and one base pair mismatch and would help to identify a mixture of target bound to single probe during melting analysis.

Testing was conducted using a proprietary chemical treatment for changing the surface charge of a biosensor. This proprietary mixture comprises of off the shelf chemicals with the primary ingredient being the positively charged polymer polyethyleneimine. Solutions of polyethyleneimine ranging in concentration from 1% to 10% in 2.5×SSC buffer were used to coat the deactivated surface of Microarray Inc. slides before the hybridization mixture was added.

Treatment of Microarray Inc slides with a 1% solution of positively charged polyethyleneimine changed the shape of the melting curve and made detection of the binding of a 50:50 mixture of perfect match and one base pair mismatched target possible (FIG. 18, graph A). During this experiment all other conditions were identical with previous microarrays except for the coating of slides with polyethyleneimine. As depicted in FIG. 18, graph A, this melting curve has two steep drop offs which are presumed to correlate with the melting of one base pair mismatch, Tm of about 59° C., and perfectly matched target with a Tm of 67° C. The difference in Tm between perfectly match and one base pair mismatch was about 8° C. Furthermore, the approximate quantities of dsDNA of each type could be inferred from the amount of relative fluorescence correlated with the melting of each product. This is shown in FIG. 18, graph A and the estimated amounts are 18.4% for one base pair mismatch and 81.6% for perfect match.

Figure 5:
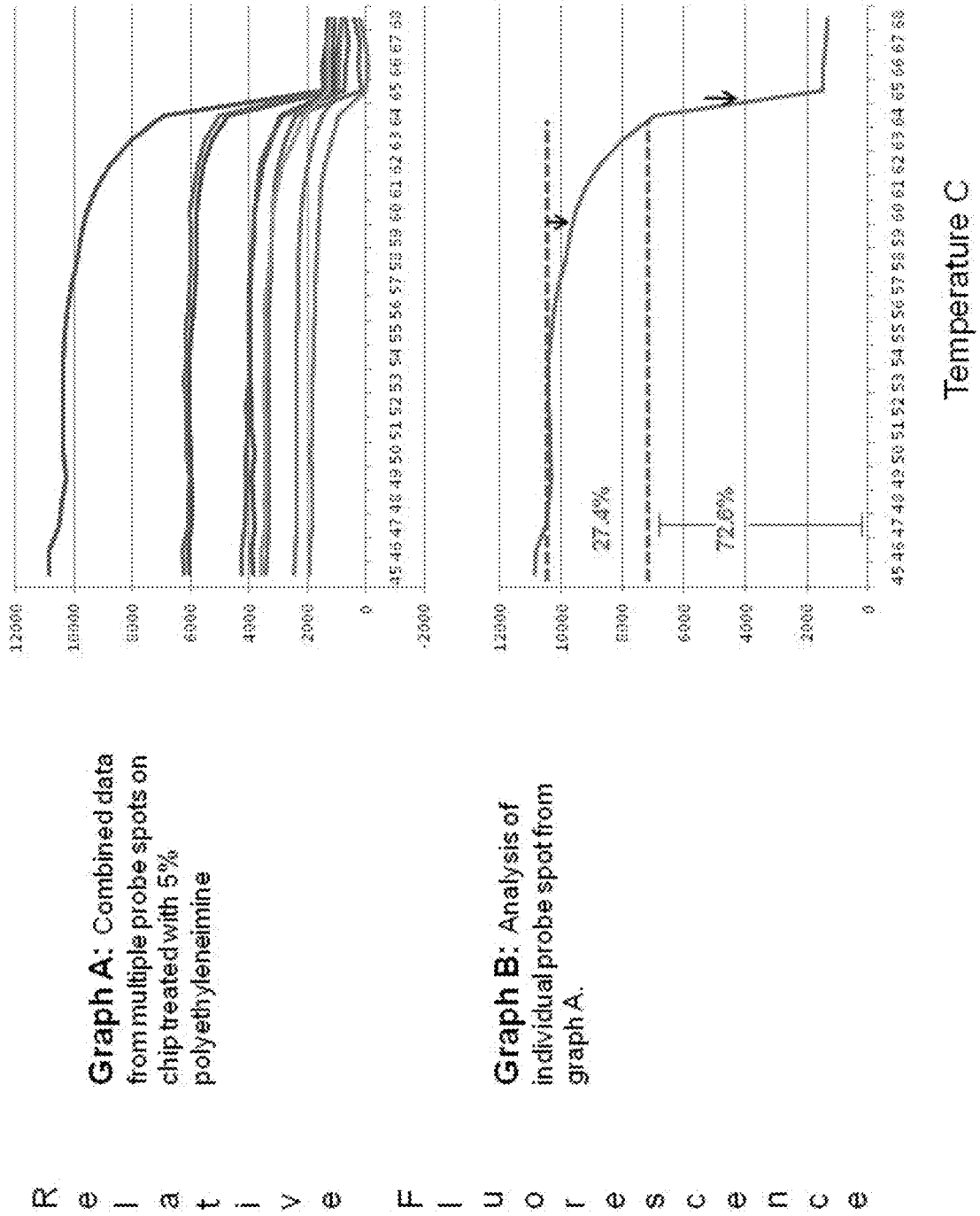
FIG. 5 illustrates exemplary results after treatment of slides with 5% polyethyleneimine according to an embodiment of the present invention.

Since a one percent solution of polyethyleneimine changed the melting curve shape to allow detection of the binding of multiple types of target, pre treatment of slides with a 5% solution was next examined. All conditions were otherwise identical to other experiments and results are shown in FIG. 5. Graph A of FIG. 5 shows the graph of 10 different probe spots and displays a very steep drop off curve with a Tm approximated by an arrow at 64.5° C. All results are raw unadjusted data. Note the consistency of the slope with graphs starting at different intensities, indicating different concentrations of target had bound to these probe spots, but melting away at exactly the same Tm. This graph resembles the shape of type B data from the Keck Center chips shown in FIG. 3B and is distinctly different from Microarray Inc, slides not treated with polyethyleneimine. Therefore, polyethyleneimine treatment appears to have some type of an effect on the binding/melting characteristics of the DNA.

As seen in FIGS. 18A-B, the presence of a positively charged surface in close proximity to the nucleic acids melting or dissociating can cause the characteristics of the melting to change. Typically, in classical liquid phase melting or solid phase melting without a positively charged surface, the two complimentary nucleic acids melt apart over a broad temperature range and not a specific temperature point (FIG. 18B). If melting nucleic acids should contain a heterozygous mixture of binding partners of both perfectly matched and one base pair mismatched both present, the melting curves of each species can overlap making the detection of the two species not possible as seen in FIG. 18B. At the beginning of the melting the binding partners containing the one base pair mismatch begin to melt apart. However, before the mismatched partners complete the melting process, the perfect match is already melting apart, generating a melting curve with a smooth ski slope masking the presence of two species of nucleic acid binding partners.

However, in the presence of a positively charged surface, the kinetics of melting can change with a sharpening of the curve. This appears to change the behavior of melting from a process that happens over a temperature range to one that happens over a short temperature transition. The end result is the ability to now distinguish the presence of both mismatch and perfectly match species in melting mixture (FIG. 18A). The melting of the mismatched species is now of shorter and sharper nature and can appear to be completed before the perfect match starts to melt. Typically, this allows the detection and quantification of both species.

According to those of ordinary skill in the art, the reason for the change of melting behavior in the presence of a positively charged surface may not be well known. However, according to one preferred embodiment of the present invention, the presence of a positively charged surface can add an additional force to the melting nucleic acids. Under most conditions, hydrogen bounding is holding the double stranded nucleic acids tighter. Typically, the hydrogen bonding is the force that must be overcome during dissociation. In the case of solid phase melting, the presence of a positively charged surface now becomes an additional force together with the hydrogen bonding that may play a role in affecting how the nucleic acids melt apart and sharpening the melting curve. One possible explanation might be that the positive charge helps to hold the labeled strand of nucleic acid more strongly than with the hydrogen bonding alone in a specific spot of the microarray. This holding effect now alters the perceived melting behavior keeping the labeled strand in place longer, then letting it melt apart in a very short temperature transition, which is still specific for the sequence of the strand.

FIG. 18, graph A produced a stair step type curve with easy identification of the Tm's for both mismatched and perfectly matched data. However, the identification of two Tm's in FIG. 5 is not easy. Type B data shown in FIG. 3 has only one very steep melting curve which confirms that only one type of perfectly matched target was present. However, FIG. 5 displays two slopes, following from left to right, the slope begins with a shallow convex shape which then turns into an almost vertical line straight down. FIG. 5, graph B breaks the melting curve into sections based on the slope of the curve. If the shallow slope represented the one base pair mismatched target melting away and the steep slope the perfect match melting, then relative amounts of each product could be calculated based on the percentage of fluorescence associated with each slope of the graph. An estimate of each product would be 27.4% one base pair mismatch with a Tm of 59.5° C. and 72.6% perfect match with a Tm of 64.5° C. Further experimentation may be conducted to confirm these estimates. It should also be noted that most but not all of target DNA melted away from the probe spots during the experiment.

Figure 6:
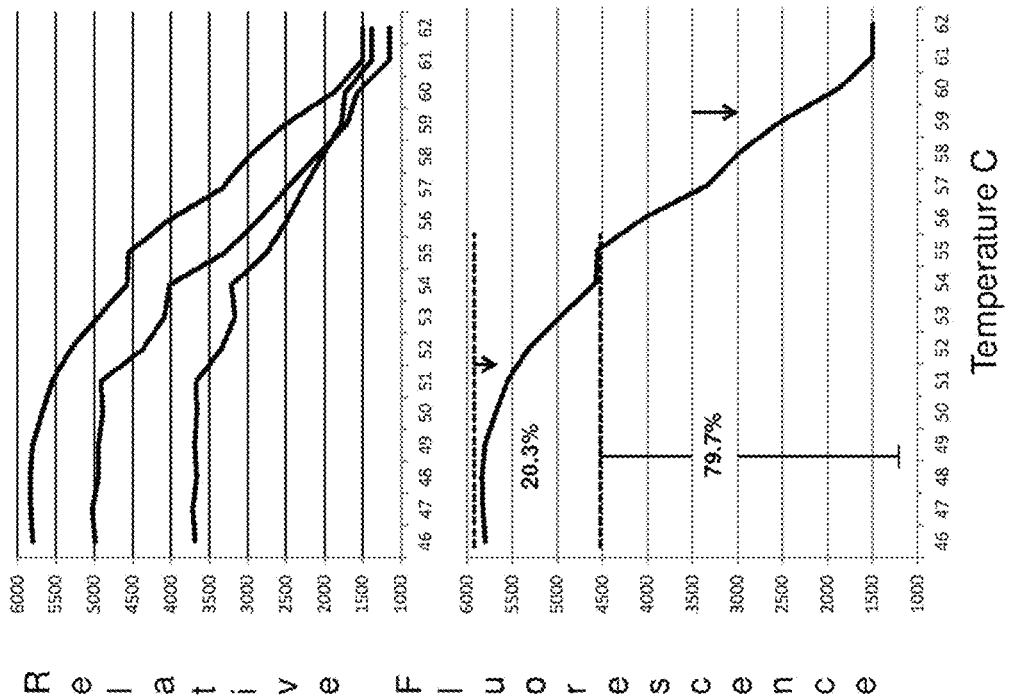
FIG. 6 illustrates exemplary results after treatment of slides with 10% polyethyleneimine according to an embodiment of the present invention.

In the next experiment a 10% solution of polyethyleneimine was used to pre-treat Microarray Inc. slides before hybridization. FIG. 6, graph A depicts a graph of a combination of several probe spots and shows a stair step type curve but with a much shallower slope than shown in FIG. 3 type B data or FIG. 5. The shape of this graph was consistent as multiple probe spots had similar but not exactly the same shape (FIG. 6, graph A). Two distinct Tm's can be observed in the slope of the graph at 51° C. and 59° C. which resembles the shape of curves found in FIG. 18, graph A. The approximate amounts of each target (FIG. 6, graph B) are 20.3% of one base pair mismatch and 79.2% perfect match. These melting temperatures are significantly lower than calculated in FIG. 18A of 59° C. and 67° C. but the difference between Tm's is identical at 8° C. These results further confirm that polyethyleneimine has an effect on the melting of target DNA that helps to distinguish the melting of multiple types of target DNA from the same probe spot. Again it should be noted that most but not all target DNA melted from the probes as the temperature increased.

Analysis of Phalanx One Array Whole Human Genome Chips

Typically, whole human genome chips contained over 30,000 probe spots and probes sequences of 60 base pairs in length. Since the number of probe spots was much higher, the individual spots were much smaller in diameter at 80 μM. One chip was processed with a mixture of CY3 dye labeled human liver and CY5 dye labeled heart cDNA. This was the first experiment with a large number probe spots and the first two color gene expression profiling microarray experiment. An objective for the scanning machine was to be able to read this chip and that the melting curve data would reduce the noise in the measurement. For example, if a given gene was expressed at a 2:1 ratio between two different samples, noise might alter the measured ratio to 1:1. It was hoped that the melting procedure would remove non-specifically bound cDNA at lower melting temperatures. This would result in an improvement in the accuracy of the expression ratio at medium and high temperatures. As the experiment continues, the temperature would become high enough to melt all cDNA from the chip marking the end of the experiment. The final gene expression ratios obtained just before the melting of all cDNA were predicted to be the most accurate. Unfortunately, the first attempt failed as the signal from each scan was so weak that the analysis software could not analyze the image file (data not shown). Visual inspection of the picture file confirmed a very weak fluorescent signal across the chip. The cause of this failure was most likely poor dye incorporation during the synthesis of cDNA and more experiments are needed to make this confirmation.

According to an embodiment of the present invention, a working instrument has been provided and method demonstrated for using thermal melting analysis in a microarray format as a novel low cost genomics analysis tool. This technique both improves the accuracy of microarrays and fills gaps not covered well by NGS. Microarray chips manufactured by the W. M. Keck Center for Comparative and Functional Genomics produced some of the most amazing melting curves but not in a consistent manner (FIGS. 3 and 4). To understand the results, an improved microarray reader has been developed. The improved microarray reader according to an embodiment of the present invention comprises improvements to the machine and its operating system, including the addition of an automatic focusing system which greatly enhanced the consistency and quality of data acquired.

In yet a most preferred embodiment of the present invention, is the effect that the microarray surface chemistry of the microarray has on the actual melting analysis. As discussed, experiments conducted using the Keck Center chips revealed unexpected results, which were determined to be affected by a non standard active epoxide surface coating on these chips. Preferably in the present invention, conventional off the shelf microarrays and supplies are not suitable for melting curve microarray analysis. This is confirmed by the very consistent melting curve data produced by the Microarray Inc. chips which were ethanolamine deactivated but unable to distinguish between different types of bound target (FIG. 18, graph B).

Typically, DNA melting analysis experiments were performed in tubes or liquid phase with the DNA free in solution. A common limitation to liquid phase melting curves is the inability to achieve one base pair resolution of detection. This methodology normally produces elongated shallow sloped melting curves which are similar to the graphs shown in FIG. 18, graph B. According to the present invention, improving the accuracy of microarrays is affected by a novel and overlooked property of the denaturation of DNA by the combined effects of heat and chemicals. The use of solid phase melting reactions can change the dynamics of the melting curve by creating a nano environment by which both heat and chemistry influence denaturation. In this format, the relevant variables that control the melting reaction can be broken down to heat, solvent flow, and surface chemistry charge. Since the target DNA is bound to the probe DNA, which is in turn bound to the solid surface of the glass array, the chemical composition of the surface of the array influences the denaturation of the DNA.

Preferably, ethanolamine, (as seen in FIGS. 18 and 19), how the surface of the microarray affects the melting of DNA might involve effects on the melted target DNA. The positively charged electrophile (epoxide) present on the Keck Center chips, resulted in a search for a convenient method to apply positive charged surface coatings to the Microarray Inc. slides already in use. Preferably, according to an embodiment of the present invention, polyethyleneimine was chosen to coat the slides. To those skilled in the art, polyethyleneimine is frequently used as a cationic lipid for the formation of liposomes used in transfection of mammalian cells. It has been determined that the cationic properties of polyethyleneimine can cause dsDNA with a net negative charge to condense within the liposome as well as causing some limited denaturation of the double stranded helix.

In a preferred embodiment, the present invention provides for the novel use of polyethyleneimine for enhancement of DNA microarray melting curve analysis. Since polyethyleneimine is a solid with a melting temperature of approximately 75° C., it is known to those skilled in the art, that the polymer stays on the surface of the glass slide at temperatures below 75° C. allowing interaction with the dsDNA located immediately above the microarray surface. The precise mechanics of this interaction are unknown but the polymers association with denaturation when used in liposomes, suggest conditions on the microarray are promoting denaturation in a manner that allows one base pair resolution of detection. This in turn may imply an effect on the strength of hydrogen bonds between base pairs. It should be noted that the Tm of the perfectly matched targeted DNA decreased as the concentration of polyethyleneimine increased from 1% to 10% suggesting a weakening of hydrogen bonds between base pairs (FIGS. 18, 5, and 6). Another possibility is that the positively charged surface is having an effect on the localization of the melted targeted DNA either causing it to be repelled or attracted to the surface as seen in FIG. 19. A repelling effect might push the target DNA away from the surface and would give the appearance of faster melting or a lower melting temperature. However, DNA generally carries a net negative charge and would likely be attracted to the positive charge of polyethyleneimine (FIGS. 18 and 19). Experiments with microarrays coated with 5% and 10% solution of polyethyleneimine showed incomplete melting of target DNA (FIGS. 6 and 6) suggesting that the target might be binding the surface of the microarray via other non hydrogen bonding mechanisms. Overall, the observed changes in DNA melting characteristics may be complex and involve more than one type of chemical interaction.

Positively Charged Surface/Effect of Ionic Strength of Buffer

As show in FIG. 19, positive charge on the solid surface typically can attract the negatively charged nucleic acids directly above the charged surface. The exact confirmation of the nucleic acids has not been determined but it is reasonable to assume that the attractive force would cause the negatively charged nucleic acids to bend over into a position which allows it to be in close proximity to the positively charged surface providing the nucleic acids and the method of attachment to the surface is flexible (FIG. 19).

In yet another embodiment of the present invention, the enhancement is provided by positively charged surface and the composition of the buffer solution. The attractive force between the nucleic acids and the positively charged surface is likely modulated by the composition of the buffer solution. Typically, a buffer containing a high ionic strength typically would contain many positively and negatively charged ions that would be attracted towards the positively charged surface and the nucleic acids, therefore reducing the perceived attractive forces between the surface and nucleic acids. Likewise, a buffer with a low ionic strength typically would have fewer ions to be attracted to the surface and nucleic acids and therefore less effect on the attractive forces between the surface and nucleic acids. This effect could be utilized to modulate the attractive force between the surface and nucleic acids by either reducing or strengthen the attractive force by changing the ionic strength of the buffer (see FIG. 19).

Microarray Analyzer

The microarray is normally read at room temperature completely dry. In order to perform melting curve analysis, a special microarray reader was built (see FIG. 8). In addition to the standard microarray reader components of the array transition stage and fluorescent microscope, a heating element and fluidics system was added. This is shown in a schematic diagram of FIG. 8A. The fluidics system included a buffer heating system capable of heating the buffer to a desired temperature and then distributing this buffer across the array to wash the array. Buffer runoff is then taken to a waste bottle. In a typical experiment, the temperature of the microarray was raised one degree Celsius. Preferably, buffer of the same temperature was flowed across the surface of the microarray and then the microscope was focused before a picture was taken. This cycle was repeated multiple times per experiment.

Figure 8A:
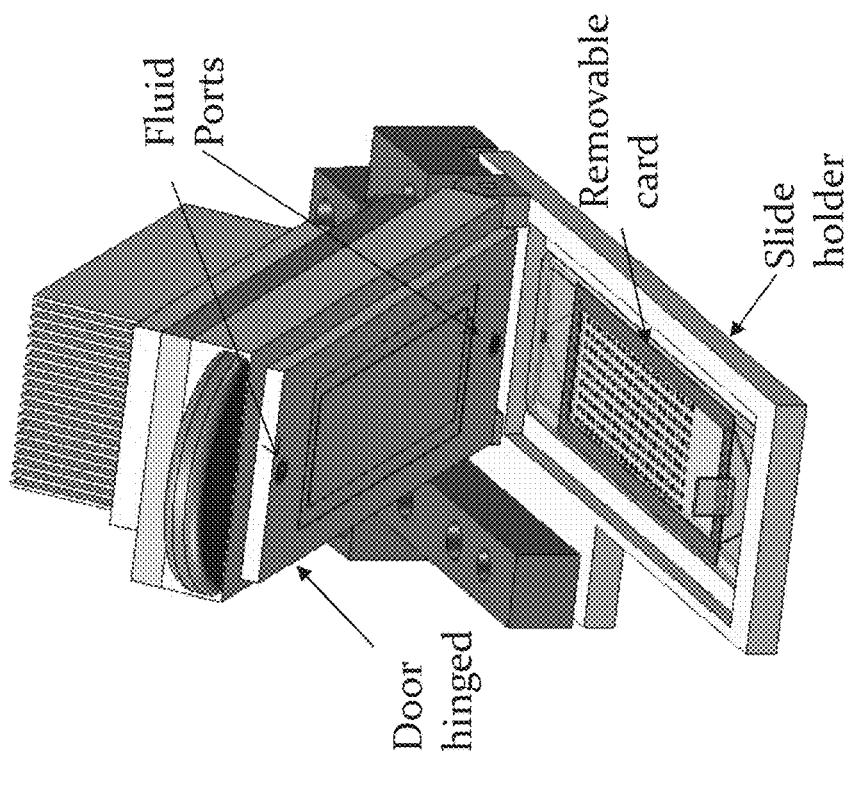
FIG. 8A illustrate an exemplary prototype microarray to perform DNA melting curve analysis according to an embodiment of the present invention.

Preferred and particular embodiments of the invention and described with more particularity in the figures described below:

FIGS. 8A-B depict a microarray to perform DNA melting curve analysis. The actual completed machine was a modified Axon 4000a microarray scanner and operated using custom software that interfaced the existing GENEPIX software included with the Axon reader. This machine was a compact unit with the main component, termed the slide card, containing both the heating element and fluidics system in the upper module (see FIG. 8B).

As shown in FIGS. 9AB and 9B an array cassette and array reader are shown. The microarray was placed DNA facing down into a plastic cassette with both in and out ports (see FIG. 9A. When the slide card was closed the ports of the slide card aligned with the ports of cassette and allowed for buffer flow (FIG. 9B). The entire microarray reader machine with the slide card in both a closed and open position is shown in FIG. 9B. The microscope was in an inverted orientation below the microarray and not clearly visible in the photo. The raster scanning process took place by moving the slide card in the Y axis and the microscope objective lens back and forth in the X axis.

Before starting each experiment, the scanning machine plumbing system was flushed with SSC buffer that was the same concentration used during the melting phase of the experiment and ranged from 2.0×-4.0×SSC. Then the thermal control chamber was pre-warmed to 44° C., and the scanner focused. The general programmed parameters for the experiment called for successive temperature incubations and washes over a range from about 40° C. to 70° C. with temperature increase increments of 1° C., a temperature hold time of 1 minute, and a SSC buffer flush of 600 µl. A scan was then made with an excitation wavelength of 532 nm with starting PMT settings ranging between 600-700 volts and scan files saved to the hard drive of the computer.

As the experiment progressed, after each temperature increase there was an automatic PMT increase of 3 units followed by an automatic focus adjustment increment. These cycles were continued until the last temperature was reached for the range of the experiment.

For each 1° C. increment of temperature change during the experiment a scan file was produced. Typical experiments generated over 20 scan files. Each scan was analyzed using the GENEPIX software according to the manufacturer's instructions. Briefly, for the first scan at a temperature of 40° C., the file was analyzed with the microarray manufacturers GAL file and GENEPIX software with a fixed surface area of the spot circle. Once the first scan was analyzed, a GPS file was generated by the GENEPIX software. The GPS file contained the software parameters used for analysis of the first scan. In order to ensure consistency of data analysis, the same GPS file was used to analyze all remaining scans from the experiment.

The resulting scan file produced for each 1° C. increment contained all the statistical data in a GENEPIX software spreadsheet format termed a GPR file. For each GPR file the column containing the Mean F532-B532 (Mean Fluorescence 532-Background 532) was copied and transferred to a MICROSOFT EXCEL software spread sheet. This procedure may be computed by hand but data compiling software was written to automate the task. All graphs were generated with the EXCEL software program. All data graphed were raw non-normalized data unless otherwise indicated.

Storage Conditions for Microarray Slides

Two different storage conditions for fabricated microarray sides were used. Boxes of microarrays slides consisting of a 25 slide pack were placed in vacuum sealed/resealable bags which were purged with nitrogen gas by the manufacture before shipping. These were stored at room temperature on arrival. Once the resealable bags were opened, the slide pack was placed in a desiccator at room temperature with fresh desiccant. Slides were removed for experiments as needed and the slide pack was placed back in the desiccator. Alternatively, individual slides were placed in individually sealed vacuum bags while working inside an argon or nitrogen glove box. Under these conditions, all unwanted reactive chemicals in the air could be removed to prevent reactions with the microarray surface. These sealed microarrays were stored at room temperature. Once the individually sealed bags were opened, experiments were started the same day and usually within 30 minutes of opening a bag. Since the slides were individually sealed they were never exposed to room air before the day of an experiment. These precautions helped to prevent any unwanted chemical reactions between the microarray and chemical contaminants in room air.

Dilution of SSC Buffer

Commercially available stock solutions of SSC buffer were used from Sigma Life Sciences (Sigma-Aldrich, St. Louis, Mo.) in a 20× concentration. Dilutions were made with distilled water in the ranges of 2.0× to 4.0×SSC buffer and placed into 250 ml GL medium storage bottles (Kimble-Chase, Vineland, N.J.). Buffers were used within 24 hours of dilutions to avoid evaporation of the solution which would alter the ion concentrations.

FIGS. 11A-B depict results obtained from amine coated microarrays. The first set of experiments was done on commercially fabricated amine coated microarray slides from ARRAYIT named the "Check It Chips". These microarray chips were designed as a calibration chip for calibrating microarray readers. The Check It Chips kit comes with a universal target DNA which can bind all probe spots. The universal target was not used and human cDNA stained with CY3 dye (ARRAYIT Corp) was instead used as the target DNA for hybridization. The melting buffer selected was SSC buffer at a 2.5× concentration which contained 0.375M NaCl. Representative results of these experiments are shown in FIGS. 11A-B. On FIG. 11A are 2 actual scans of the microarray at the beginning of the experiment at 45° C. and the end of the experiment at 65° C. The scan at 45° C. shows the square shaped probes spots of both blocks of the microarray which are replicates of each other with many of the probes fluorescing due to the binding of the target human cDNA. The positive control probe spots are CY3 dye bound directly to the glass and have a rounded shape. These are located in the upper left and lower right corners of each block. In the 65° C. scan most of the target DNA bound to test probes was melted away leaving the round shaped positive control spots fluorescing.

Summary of Results:
Experiments with Amine Coated Microarrays

On FIG. 11B are shown melting curves obtained on unblocked amine coated surface plates with 2.5×SSC buffer for Cadherin 1 (FIG. 11B1) and Beta Actin (FIG. 11B2). The first set of experiments was done on commercially fabricated amine coated microarray slides from ARRAYIT named the "Check It Chips". These microarray chips were designed as a calibration chip for calibrating microarray readers. The Check It Chips kit comes with a universal target DNA which can bind all probe spots. The universal target was not used and human cDNA stained with CY3 dye (ARRAYIT Corp) was instead used as the target DNA for hybridization. The melting buffer selected was SSC buffer at a 2.5× concentration which contained 0.375M NaCl. Representative results of these experiments are shown in FIG. 11. On the left side of FIG. 11 are two actual scans of the microarray at the beginning of the experiment at 45° C. and the end of the experiment at 65° C. The scan at 45° C. shows the square shaped probes spots of both blocks of the microarray which are replicates of each other with many of the probes fluorescing due to the binding of the target human cDNA. The positive control probe spots are CY3 dye bound directly to the glass and have a rounded shape. These are located in the upper left and lower right corners of each block. In the 65° C. scan most of the target DNA bound to test probes was melted away leaving the round shaped positive control spots fluorescing.

Referring again to FIG. 11B graphs of the melting curves generated depict the most striking feature of the graphs show the generation of sharp melting curves. The section of the melting curves where the DNA melting took place is marked with an arrow which approximates the Tm. As shown in the graph of FIG. 11B, the results of the melting curve for the probe spot Cadherin 1 is shown. Between the start of the curve at about 40° C. and the beginning of the melting curve at about 59° C. the graph is almost horizontal with a slight upward slope. At about 60° C., there is a sharp downward slope that is the melting curve. The presence of one melting curve in the graph suggests that there is one type of target DNA which has bound the probe spot and is melting away. Based on the Tm of the melting curve which is estimated to be about 61° C., the target is likely to be the true perfect match target of the probe and not mismatched target. As seen in FIG. 11B, the graft depicts two melting curve Tms obtained from the Beta Actin probe spot, one at about 62° C. and another at about 46° C. The true power of the melting curves becomes apparent in this graph as it was able to detect the presence of perfectly matched target melting at 62° C. and mismatch target melting at about 46° C. both on the same probe spot. The Check It Chips kit did not include a blocking agent that would normally neutralize the positive charged amine coated array surface. So it can be assumed that the surface was positively charged. Microarray surfaces are normally chemically blocked and would be expected to have a near neutral surface charge. The blocking is performed in order to prevent nonspecific binding of target DNA to the array surface which would produce background noise. The detection of both perfect match and mismatch target on the sample probe spot is not normally possible. The temperature ranges of melting of the perfectly match and mismatch overlap during liquid phase melting analysis and sold phase melting on blocked microarray surface chemistries.

Figure 12:
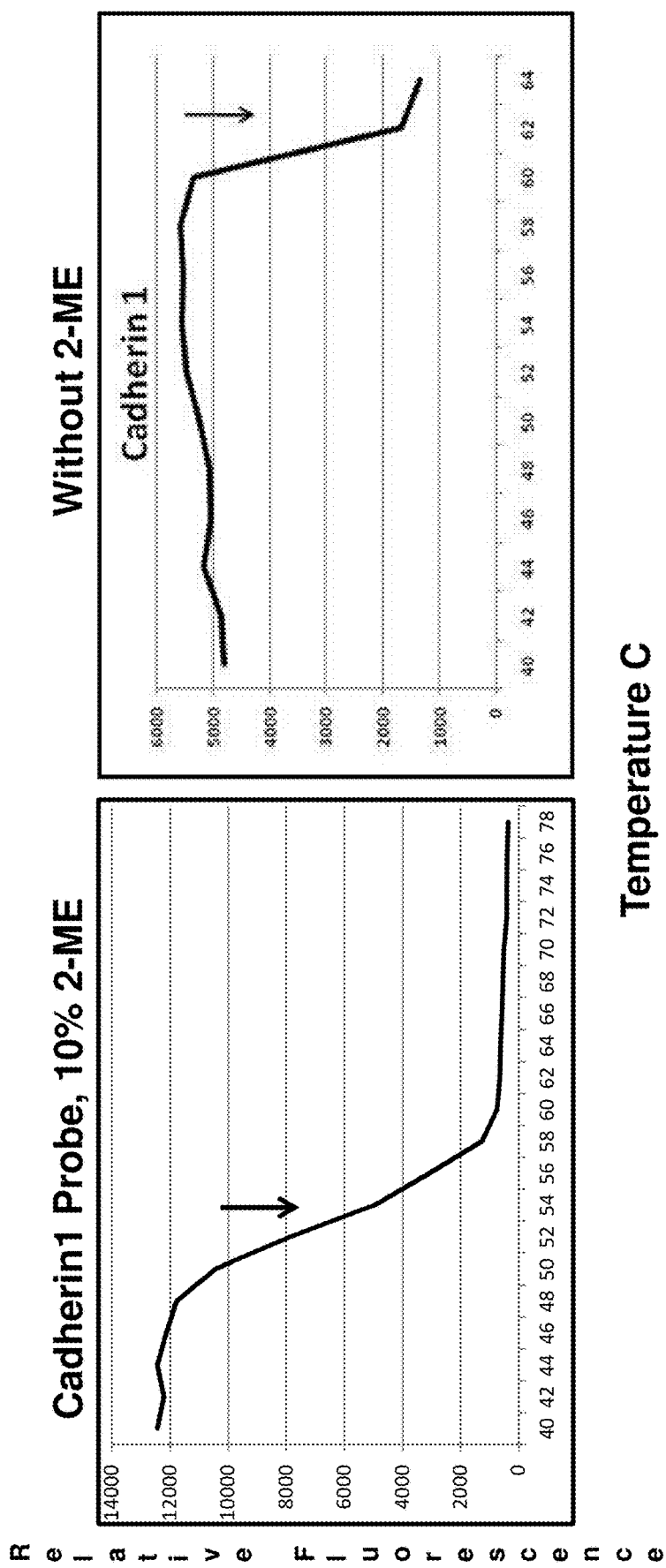
FIG. 12 illustrates the effects of 10% 2-Mercaptoethanol on DNA melting curves according to an embodiment of the present invention.

In an effort to reduce photobleaching of the fluorophore, a 10% solution of 2-Mercaptoethanol (ME) with 2.5×SSC buffer was used. The effect this had on the melting curves is shown in FIG. 12. Graphs of the probe spot Cadherin 1 are shown in the presence and absence of 10% 2-Mercaptoethanol. When 2-Mercaptoethanol was used the intensity of the fluorescence was greater and the graph started at about 12,000 relative units of fluorescence. Without the use of 2-Mercaptoethanol, the graph started at a little under 5000 relative units of fluorescence. This confirms that the 2-Mercaptoethanol can reduce photobleaching of the fluorophore. Furthermore, 2-Mercaptoethanol changed the shape of the slope of the curve and the Tm. Without 2-Mercaptoethanol the slope is very sharp with a Tm of about 62° C. With 2-Mercaptoethanol the slope is shallower with a Tm of 54° C. Experiments were repeated with 2-Mercaptoethanol but none were able to replicate the sharp melting curves that could distinguish the presence of both perfect match and mismatch on the same probe spot as shown in the graph seen in FIG. 11B. Since the ability to discriminate between the different species of targets binding the same probe was the most valuable data obtained, the use of 2-Mercaptoethanol was discontinued as it interfered with this detection.

FIG. 12 depicts the effects of 10% 2-Mercaptoethanol on DNA melting curves. As shown, the use of unblocked amine coated slides in the presence of 2.5×SSC buffer was capable of producing unusually sharp DNA melting curves with the ability to detect the presence of both perfect match and mismatch melting away from the same probe spot. The use of 10% 2-Mercaptoethanol helped to reduce photo bleaching of the CY3 dye but also altered the characteristics of the melting curve by lowering the Tm and changing the slope of the melting curve making it a shallower curve. The change in the slope indicates that the temperature range of melting was wider in comparison to the melting curves performed using only 2.5×SSC buffer. These novel methods show the importance of having a positively charged microarray surface, and the effects that buffer chemistry have on narrowing the temperature range of melting of a particular DNA sequence to produce enhanced melting curves.

Experiments with Epoxy Coated Microarray Slides

Experiments started with a commercially produced amine coated microarray with preselected probe sequences. The next set of experiments was designed with custom probe sequences on epoxy coated microarray slides and the hybridization target was a perfect match sequence and/or mismatch of one base pair. The objective of the experiment was to create conditions that reproduced the ability of the melting curves to produce two stepped curves which could distinguish the presence of both perfect match and one base pair mismatch binding the same probe spot.

The first experiments were conducted with only perfectly matched target on epoxy slides produced by the Functional Genomics Lab. The data fell into two types. The first experiment produced graphs of every probe spot on the microarray with a very sharp slope which was nearly vertical. This was called a "stair step melting curve" and given a classification of type B data (FIG. 3). The second type of data was a graph with a much shallower slope, which was called a ski slope curve and given the classification of type A data (FIG. 3). As more experiments were performed the number of microarray chips that produced melting curves with the ski slope shape outnumbered the stair step shape by approximately 4:1. The sharp stair step data was more desirable because of the much narrow temperature range of melting. However, there were issues with repeatability. It was clear that the stair step data was repeatable but not consistently. This indicated that there was some unknown variable or perhaps multiple variables that were changing between experiments.

The first batch of microarray chips was depleted, and in order to expedite the reordering process, a new vendor was contacted, Microarray Inc. Epoxy microarray chips were ordered which were identical to the previous batch in both surface chemistry and probe sequences. Experiments with these new chips and perfectly matched target DNA produced ski slope type melting curves for all probe spots on the array. This was repeated several times consistently.

These results suggested that were differences between the microarrays ordered from the Functional Genomics Lab and Microarray Inc. Technical support at each vendor was contacted and it was discovered that the microarrays produced by the Functional Genomics Lab had a live epoxy surface and separate instructions were emailed that specified deactivation with ethanolamine before use to neutralize the epoxy surface. It was determined that deactivation of the epoxy surface worked best just before an experiment is performed. The microarrays were processed as though the surface was already deactivated. This caused the lab to unknowing use epoxy microarrays with a reactive epoxy surface. The microarrays printed by Microarray Inc. were deactivated with ethanolamine before shipping. So the slides from the Functional Genomics Lab with live un-neutralized or un-blocked surface produced the sharp stair step melting curves but inconsistently.

FIG. 3 shows types of melting curves obtained on epoxide-coated microarray slides. The top graph of FIG. 3 shows a ski slope melting curve and the bottom graph depicts a stair step melting curve.

Figure 14:
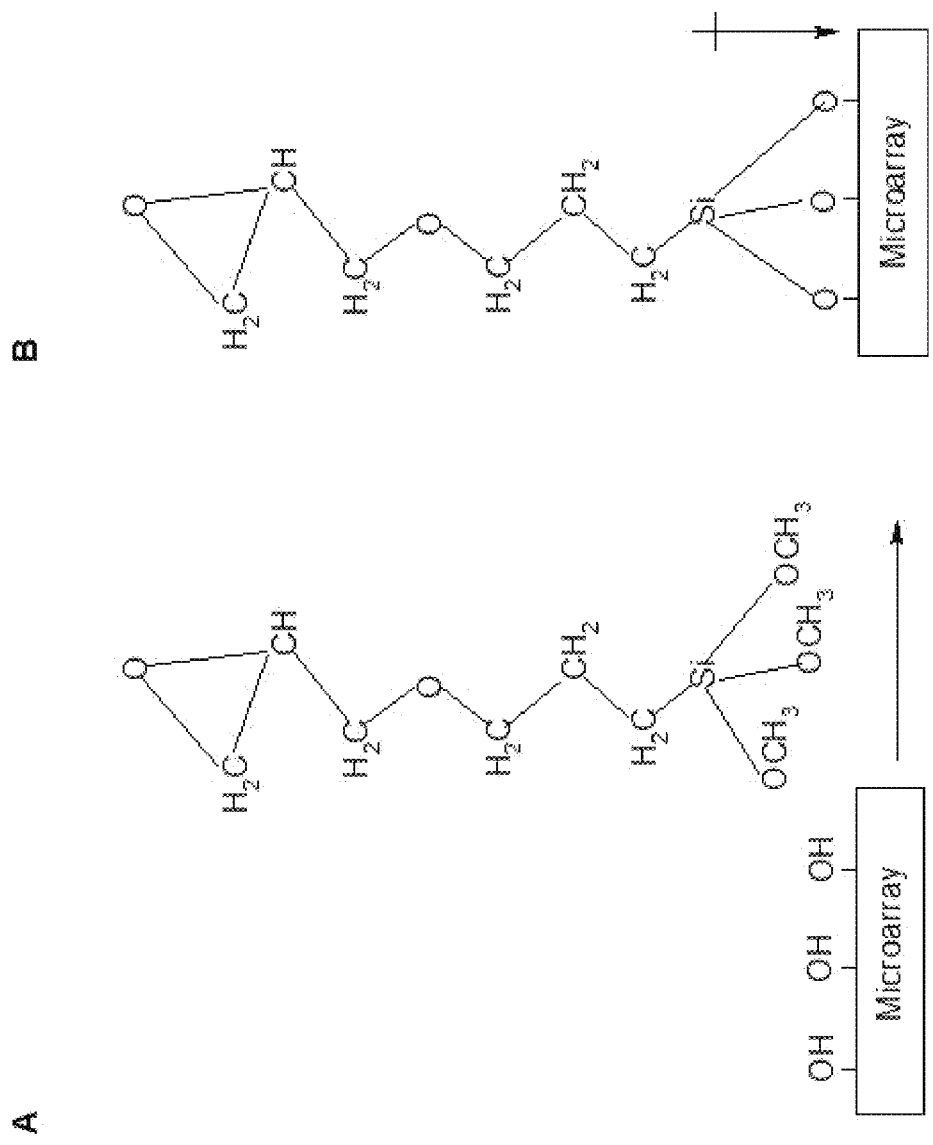
FIG. 14 illustrates epoxy silane attachment to a glass microarray according to an embodiment of the present invention.
Figure 15:
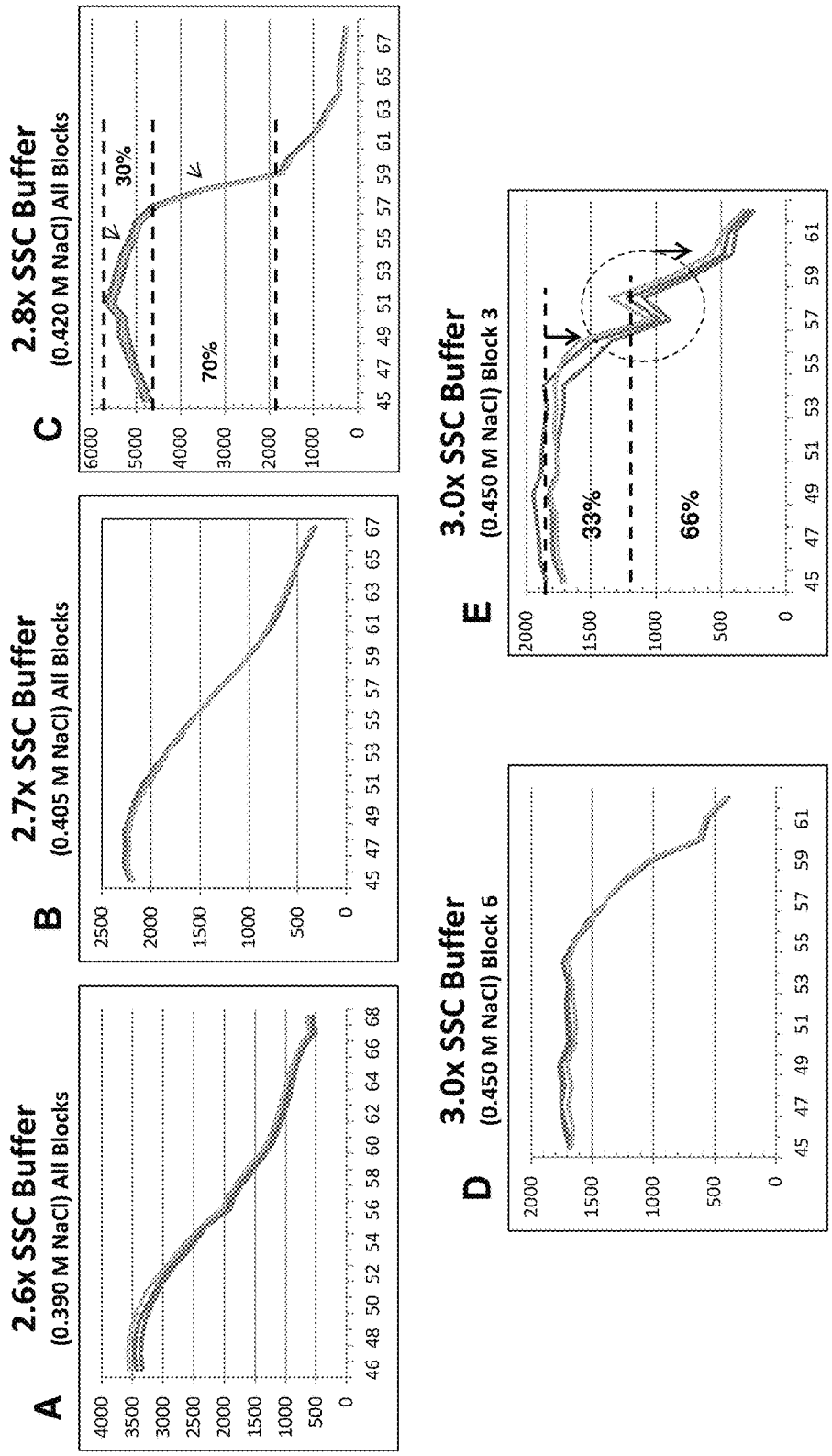
FIG. 15 illustrates DNA melting curves on unblocked epoxy coated microarrays with glass cover slips according to the present invention.

FIGS. 14A-B depict epoxy silane attachment to a glass microarray. The epoxide that is commonly attached to the glass microarray is in the form of epoxy silane. The structure of epoxy-silane is shown in FIG. 14A. The silicon (Si) in the epoxide silane molecule is bonded to three oxygens (O). In this arrangement, the 3 oxygens each with an electronegativity value of 3.44 (on the Pauling Scale) act to withdraw or hog electrons shared by the bonds with 1 silicon atom with an electronegativity value of 1.90. This creates a strong dipole moment in which the silicon is the positively charged side of the dipole and the oxygens are on the negatively charged side of the dipole. When the epoxy silane molecule is attached to the glass microarray surface (FIG. 14B), the dipole is oriented such that the negatively charged side of the dipole is nearest to the glass surface. Therefore, the positively charged silicon is oriented above the negatively charged oxygens. When the microarrays are printed, single stranded DNA modified with amino acids at one terminus can become attached to the epoxide group via a nucleophilic substitution reaction. Once the DNA is attached, the silicon oxygen dipole is oriented with the positively charged silicon nearest the DNA. Therefore, although the epoxide coating is neutral in charge, there is a layer of positive charge below the DNA and above the microarray slide.

As with the unblocked amine coated microarray slides, positive charge on the surface of the array is present when sharp stair step melting curves are produced. Once the epoxy coated microarray slides are blocked with ethanolamine, it is not possible to generate sharp enhanced melting curves. The purpose of blocking the epoxy coated microarray is to prevent the epoxy from nonspecifically binding target DNA during hybridization which would cause an increase in background noise. Blocking with ethanolamine allows a nucleophilic substitution reaction to occur between the epoxy and ethanolamine. Other methods of blocking the epoxy microarray surface also utilize nucleophilic substitution reactions with epoxy. If positive charge on the surface of the microarray is truly a requirement to produce enhanced stair step melting curves then modifying the blocked epoxy coated microarrays to create positive charge on the surface should in theory allow the arrays to produce these types of melting curves.

FIGS. 18A-B depict coating microarray slides with polyethyleneimine. One method to add positive charge to the surface of epoxy microarrays blocked with ethanolamine, is to coat the surface with a cationic polymer polyethyleneimine (PEI). After the pre-hybridization procedure but before the hybridization was performed, a solution of branched PEI which range from 1% to 10% in 2.5×SSC buffer was incubated on the surface of the microarray for 20 minutes, and then lightly washed with 2.5×SSC buffer. Hybridization was completed and melting curves generated. On the first experiment, the concentration of PEI was 1% and the target DNA was a 50:50 mixture of perfectly match target DNA and 1 bp mismatch. The results of this experiment are shown in FIG. 18A. This melting curve produced a 2 stepped curve confirming the binding and then melting of both the perfectly matched target with a Tm of about 67° C. and the 1 bp mismatched target with a Tm of 59° C. It was noticed that the temperature range of melting of the mismatched target does not overlap with the temperature range of melting of the perfectly matched target. This is evidenced by the change in slope of the graph to a flat spot with no slope at about 600-62° C. In this short section of the graph no melting is taking place. An estimate of the percentage of each target that bound the probe can be made by measuring the amount of relative fluorescence lost during the melting curves. Estimates are 81.6% perfect match and 18.4% mismatch (FIG. 18A). This shows that perfectly matched target has a preference for binding but mismatch can also bind under these conditions.

The exact same experiment was performed on epoxy coated slides blocked with ethanolamine and not coated with PEI. This chemistry was termed standard chemistry and the results are shown in FIG. 18B. The graph of this melting curve is notably different. The most obvious difference is the lack of a step or flat area of the graph anywhere in the slope (FIG. 18B). This indicates that the temperature ranges of melting of perfect match and 1 bp mismatch overlap. Since the temperature ranges overlap there is never a section of the graph where melting stops after the 1 bp mismatch target has completed melting and before the perfectly matched target begins to melt. Therefore, it is impossible to use the slope of the melting curve graph as a method to detect the presence and melting of the perfectly matched and 1 bp mismatched target binding the same probe spot. An arrow has been placed in the middle of the slope of the graph in FIG. 18B to represent the Tm of the melting curve. However, this assumption is wrong as there is not one type of target DNA melting away but rather two types of DNA targets melting away each with their own Tms and the temperature ranges of melting are overlapping. In this example the arrow does not approximate the Tm of either target DNA and simply marks the middle of the melting curve slope.

The experiment comparing the results from a blocked epoxy slide coated with 1% PEI and a blocked epoxy coated slide without PEI further supports the hypotheses that a positively charge microarray surface is needed to produce the enhanced stair step type melting curves. Subsequent experiments were performed on blocked epoxy slides with PEI treatments of 5% and 10%. When a 5% PEI coating was used very sharp melting curves were obtained (FIG. 5A) which resembled the sharp stair step melting curves obtain on an unblocked epoxy slide with only perfectly matched target (FIG. 5B). A key difference between these experiments was that 5% PEI coated slides had a 50:50 mixture of both perfect match and 1 bp mismatch target. There was no obvious step or flat spot in the melting curve but rather a marked change in slope shown in FIG. 5B. Using the change of slope of the melting curve as a marker to distinguish the temperature range of melting of two different target species, arrows were placed over the graph estimating the Tms of each target type. The concentration of 1 bp mismatch is estimated to be 27.4% with a shallow slope and the amount of perfect match is estimated to be 72.9% with very sharp slope that is nearly vertical.

The experiment was repeated with a 10% PEI coating on the slides with the results shown in FIGS. 6A-B. As can be seen in both graphs of FIGS. 6A and 6B, DNA melting generated a curve with sharp slopes and flat step in the middle. This is similar to the melting curves produced with a 1% PEI treatment shown in FIG. 18A. This result can clearly distinguish the presence of both mismatched and perfectly matched targets melting away from the same probe spot. The estimate for the percentage of mismatch is 20.3% and perfect match 70.7%. Differences in the graphs produced with different concentration of PEI are the shape of the slopes and Tms. Graphs produced with 1% PEI and 10% are similar in shape but the slope is steeper with 10% PEI. Furthermore, the Tms are different with a 1% PEI treatment producing a 1 bp mismatch Tm of 59° C. and perfect match of 67° C. The Tms for the 10% PEI are approximately 51° C. for the 1 bp mismatch and 59° C. for perfectly matched target. There is approximately an eight degree reduction in temperature for the Tms with 10% PEI compared to 1% PEI. Furthermore, there is about an eight degree difference between the Tm of 1 bp mismatch and perfectly matched target at both concentrations of PEI.

PEI is a positively charged polymer and it can be assumed that the concentration of PEI that is used to coat the microarray surface can also be used to change the level of positive charge on the surface. It is reasonable to assume that the level of positive charge on PEI coated arrays of 1%, 5%, and 10% were different, with the higher concentrations having higher levels of positive charge. While positive charge is needed to produce the enhanced 2 stepped melting curves, the amount of positive charge needed appears to not be limited to just one specific level of positive charge but can vary to some degree. This is evidenced by the ability of both 1% and 10% PEI coatings being able to produce 2 stepped melting curves but with different characteristics. However, using PEI coatings as method to create a positively charged microarray surface has significant limitations. For all the microarrays processed with PEI only certain areas of each slide were able to produce the enhanced step melting curves or the 2 stepped curves. The other sections of the slide did not produce this effect. This was observed for all slides processed with PEI. The reason for this is not confirmed but branched PEI is liquid at room temperature. It is possible that the PEI coatings may have not been distributed evenly on the surface after a 20 minute incubation period or may have washed away in certain regions of the microarray during the experiment.

FIGS. 6A-B depicts a blocked epoxy slide coated with 10% polyethyleneimine. During experimentation that the recycling of the microarray cassettes by cleaning them with laboratory glassware detergent was not feasible as the reused cassette would not produce any sharp melting curves. This effect only happened with the use of PEI at any concentration. It was hypothesized that there may have been a buildup of PEI on the inner surface of the cassette that could not be washed away using standard laboratory detergents. This buildup of PEI may have changed the surface charge of the cassette plastic surface and glass cover slip making them positively charged. The buildup of this charged surface then altered the nucleic acid melting dynamics in a way that did not produce the enhanced melting curves. This problem was solved by not reusing the cassettes.

Experiments with Unblocked Epoxy Coated Microarrays Slides and Different SSC Buffer Concentrations Experiments have shown that a positively charged microarray surface is needed to produce enhanced melting curves with the ability to discriminate the presence of both perfectly matched and 1 bp mismatch targets melting away from the same probe spot. Three distinct types of surface chemistries have produced this effect. These chemistries include unblocked amine chemistry, unblocked epoxy chemistry, and surface coatings of PEI on blocked epoxy slides. Further experiments with PEI were not continued because of its inability to produce consistent results across the whole microarray surface.

Unblocked epoxy slides gave some of the best data but there were problems with repeatability between experiments. The cause of the repeatability issues was not initially understood. One hypothesis was that the buffer concentration of 2.5×SSC buffer may have been different from experiment to experiment as fresh SSC buffer was left in the same bottle for days at a time and evaporation may have occurred which increased ion concentrations. Experiments with amine coated microarray demonstrated that the buffer composition can have a profound effect of the melting curves. The objective of the next set of experiments was to use unblocked epoxy microarrays and to vary the concentration of SSC buffer in order to determine the optimal SSC buffer concentrations.

Experiments were restarted with unblocked epoxy coated slides ordered from Microarray Inc. These arrived in a pack of 25 microarrays boxed in a vacuum sealed bag purged with nitrogen. Once the bag was opened, a microarray was removed for use, and the microarray slide box was placed in a desiccator with fresh desiccant at room temperature. No vacuum was applied to the desiccator. Fresh SSC buffer was made no more than 24 hours before the start of an experiment. Since buffer concentrations of 2.5×SSC gave inconsistent results and it was believed that the buffer ion concentrations may have increased due to evaporation in earlier experiments. Experiments were started with a 2.6×SSC buffer concentration and gradually increased the concentration in later experiments. The hybridization consisted of a 50:50 mixture of perfect match and 1 bp mismatched target.

FIGS. 15A-E depict DNA melting curves on unblocked epoxy coated microarrays with glass cover slips. The results of the first set of experiments are show in FIGS. 15A-E. Each graph FIGS. 15A-E shows the melting curves of three separate probe spots near to each other on the same microarray.

For all the melting curves graphs shown in FIGS. 15A-E, the consistency of the shape of the curve for all three probes spots shown is remarkable, with the graphs often laying on top each other. It was hypothesized that the 2.5×SSC buffer concentrations used in earlier experiments may have concentrated via evaporation after a storage period of several days or longer and that the results showing enhanced melting curves actually had buffer concentrations higher than 2.5×SSC. The results for SSC buffer concentrations of 2.6× and 2.7× each show melting curves with the ski slope form with no change in slope to indicate a mixture of perfect match and 1 bp mismatched target (FIGS. 15A-E). These results were consistent over the entire surface of the microarray. When the concentration of SSC buffer was raised to 2.8×SSC (0.420M NaCl), the slope of the graph became much steeper (FIG. 15). The 2.8×SSC buffer graph shows a gradual slope upward at the beginning due to the focus of the microarray being slightly out focus at the start and then going into focus as the temperature of the experiment increased. This occurred because changes in temperature change the refractive index of the SSC buffer, which in turn changes the focal point. The machine was designed to compensate for changes in refractive index by increasing the PMT gain with each temperature increase. However, if the first scan was not in good focus then compensational changes in gain will not work as well. Next there is a slight downward slope before the slope of the graph become almost vertical. This graph is similar to the melting curve graph generated on blocked epoxy slides with 5% PEI (FIG. 3). There were obvious changes in the slope of the curve but no flat step in the graph. If the change in downward slope is used as an indicator of the melting of 1 bp mismatch and perfectly matched target then the relative percentages of each can be estimated to be 30% 1 bp mismatch and 70% perfectly matched (FIGS. 15A-E). This result was consistent over the entire microarray surface.

The next concentration of SSC buffer used was 3.0× (0.450 M NaCl). At this concentration, there were variations in the type of graphs produced in different sections of the microarray. In blocks 3 and 6, sharp enhanced melting curves were produced (FIGS. 15E and 18D) and the remainder of the slide produced ski slope type curves (not shown). The graph of block 3 shows three separate graphs from three different probe spots with an obvious change in slope that resemble the stair steep type curve or 2 stepped curve. The step in the curve is not flat but rather has a sharp upward slope (FIG. 15E with dashed circle). This anomaly was due to the incomplete flushing of buffer out of the cassette between flushing cycles. So, melted target that had just melted away from probe spots was not completely flushed away but rather moved somewhat within the cassette so that when the next scan was taken, the fluorescence of the group of probe spots in a particular area of the slide was slightly higher. This problem was caused by a poor seal in the buffer tubing connection point which caused a reduction in the volume of buffer pumped. The graph of block 6 (FIG. 15E) of the 3.0×SSC buffer concentration was different (FIG. 15D). The slope was much steeper than the ski slope graphs of SSC buffer concentrations of 2.6× and 2.7× but without an obvious change of slope until later in the graph at a higher temperature.

Of the graphs produced with 3.0×SSC buffer concentration, block 3 (FIG. 18E) yielded the best data while block 6 was not the same as the ski slope graphs of 2.6× and 2.7×SSC buffer but not an ideal graph either. From these results it became clear that there was variation in the ability of the unblocked microarrays to consistently produce enhanced melting curves across the entire array. It should also be noted that SSC buffer concentrations which did not produce any enhanced melting curves (e.g. 2.6× and 2.7× SSC) had great consistency in the melting curve slopes over the whole microarray surface.

FIGS. 16A-D depict stability comparisons of unblocked epoxy slides before and after one month. About one month had elapsed since starting experiments with the new microarrays ordered from Microarray Inc. In an effort to clarify these results more melting curves experiments were done at the 2.8×, 2.9× and 3.0×SSC buffer concentrations. None of these experiments could repeat the enhanced stair step type melting curves generated with 2 stepped curves or even steep melting curves. Two example results are shown in FIGS. 16A-D. SSC buffer concentration 2.8× and 3.0× were both able to produce sharp enhanced melting curves before one month had passed after first opening the microarray slides from the vacuum sealed bag and being placed in the dissector. However, after one month had passed, neither 2.8× (FIG. 16B) nor 3.0×SSC buffer (FIG. 16D) concentrations could not repeat this result. Both buffer concentrations produced long gentle melting curves slopes (FIGS. 16B and 16D). Furthermore, the buffer concentration of 2.9×SSC buffer which had not been attempted before, produced the same very gentle ski slope curve (data not shown). This seemed to indicate that something had changed over the one month period and the vendor, Microarrays Inc. was contacted for technical support. They suggested that perhaps chemicals in the air in the desiccator and the lab room air were capable of chemically reacting with the unblocked epoxy microarray surface. If this was occurring, it was a slow process that took place over days and weeks.

To prevent unwanted chemical reactions from occurring to microarrays in future experiments, unblocked epoxy microarrays were stored as individual microarrays and transferred to vacuum sealed bags inside an argon glove box. This was accomplished by taking a second box of microarrays in a 25 pack fabricated by Microarray Inc. that was still sealed in a nitrogen purged bag. This bag was opened inside an argon gas glove box and each microarray transferred to an individual slide box and vacuum resealed in an individual vacuum bag while still inside the argon glove box. This procedure ensured that the slides were not exposed to room air at any time. Once the transfer had been completed, experiments were resumed by varying the concentration of SSC buffer in each experiment as before. Another small change to note was the switch from glass cover slips on the microarray cassette to plastic cover slips.

Figure 17:
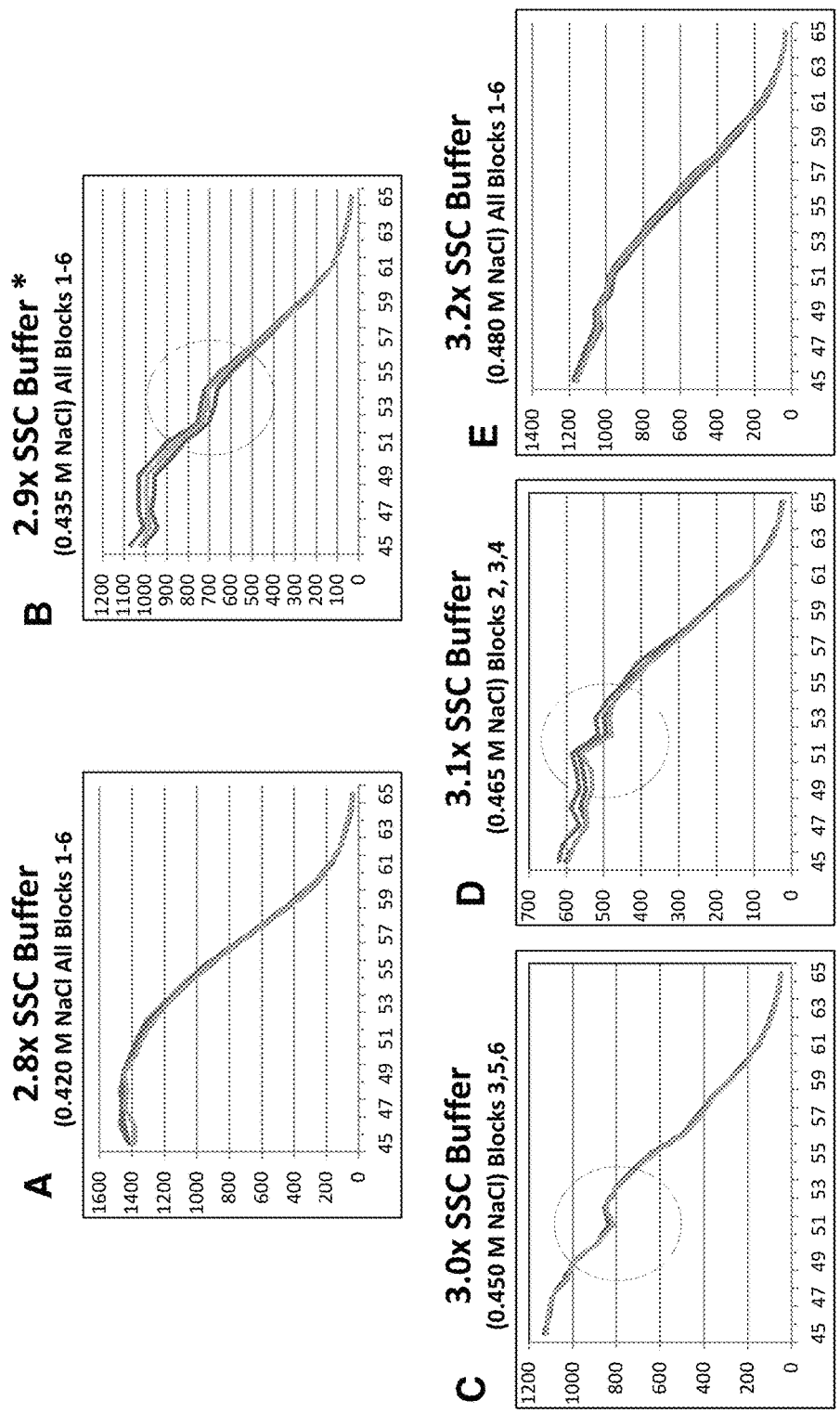
FIG. 17 illustrates melting curves on unblocked epoxy coated slides with plastic cover slips according to the present invention.

FIGS. 17A-E depicts melting curves on unblocked epoxy coated slides with plastic cover slips. The experiments resumed starting with a 2.6×SSC buffer concentration and ending at a 3.3×SSC buffer concentrations. The results of these experiments are shown FIG. 17 and all graphs depict three different probe spots near each other in the same block. The SSC buffer concentrations of 2.6×, 2.7×, and 2.8× all showed a ski slope type melting curves. The result of the 2.8×SSC (0.420 M NaCl) buffer concentrations is representative of the 2.6× and 2.7× concentrations and is shown in FIG. 17. It is not possible to detect the presence of two different DNA targets melting away from the probe in this graph as the slope is rather smooth and without abrupt slope changes. Now when the SSC buffer concentration is increased to 2.9×SSC (0.435M NaCl) there is a striking change in the graph as a noticeable flat spot occurs (FIGS. 17A-E) with a dashed circle marking it (FIGS. 17B, 17C, and 17D). This type of melting curve slope occurred on every probe spot on the array which includes all 6 blocks. Notice that it only took a 0.015M increase in NaCl concentration to produce this melting curve. Also the melting curves of the three separate probe spots are very similar on lie on top of each other in the later section of the curve. This is an ideal curve as it is easy to distinguish the presence of both perfect match and 1 bp mismatch target melting away.

As the concentration of the SSC buffer is increased to 3.0× and 3.1×SSC, the graphs also have a flat step marked by a dashed circle around the change in slope (FIGS. 17A-E). These types of melting curves occurred in 3 blocks out of 6 blocks or about half the probe spots on the microarray. Notice that the flat step occurs between 51° to 53° C. at the SSC buffer concentrations of 2.9×, 3.0×, and 3.1×SSC. As the buffer concentration is increased to 3.2×SSC (0.480M NaCl) the flat step or abrupt change in the slope of the graph is lost. There are some small irregularities in the graph of the 3.2×SSC buffer concentration in the temperature range of 47° to 51° C. However, these are not the same type of slope change seen in the SSC buffer concentrations of 2.9× to 3.1×. Like the 2.8×SSC buffer concentrations, it is not possible to detect the melting of the perfect match and 1 bp mismatched target. However, there are subtle differences between the graphs of the 2.8× and 3.2×SSC buffer concentrations. The 3.2×SSC buffer graph has a shallower slope and lacks the flat section of the graph at the very beginning of the melting curve.

The results depicted in FIGS. 17A-E confirm that the SSC buffer concentration is an important factor for obtaining the enhanced melting curves with two stepped curves. It appears that the enhanced melting curves only occur within a range of buffer concentrations. The observed range starts above 2.8×SSC buffer (0.420M NaCl) and below 3.2×SSC buffer (0.480M NaCl). Within this range the 2.9×SSC buffer concentration appears to work best since all probe spots show the enhanced melting curves and the shape of the curve is near ideal. In comparison, the SSC buffer concentration of 3.0× and 3.1× showed the enhanced melting on half the probe spots of the microarray and the shape of melting curves were not as ideal. Although the enhanced melting curves occurs over a range of SSC buffer concentrations, the lower side of the buffer range of 2.9×SSC appears to work best. Earlier experiments with epoxy slides showed that enhanced melting curves could be obtained with 2.8×SSC buffer concentration when using glass cassette cover slips (FIGS. 15A-E). This result was not possible using plastic cover slips (FIGS. 17A-E). This suggests that there is a difference in the chemical properties between the glass and plastic cover slips that affects the nucleic acid melting in this particular system. If more experiments had been completed with glass covers slips, it may have been possible to confirm the range of SSC buffer concentrations that are able to produce the enhanced two stepped melting curves. With the data shown on FIGS. 15C and 15E, a possible range of buffer concentration could be 2.8× to 3.0×SSC but the ability of 2.9×SSC buffer to produce enhanced melting curves falls within the effective concentration ranges.

In accordance with the present invention, it is possible to consistently produce enhanced two stepped melting curves on unblocked epoxy microarray slides. There are at least two considerations to ensure repeatability. The first are special storage conditions for the unblocked epoxy microarrays to prevent unwanted chemical reactions with contaminates in the air that might change the chemistry of the surface. This problem was solved by special packaging in individual vacuum sealed bags in an argon gas glove box. The second consideration is SSC buffer concentration or more specifically, the concentration of ions in the buffer solution. The enhanced melting curves only occur within a range of SSC buffer concentrations. To most accurately determine the SSC buffer range, buffers were made within 24 hours before starting experiments to avoid evaporation and a change of ion concentration.

FIGS. 19A-B depict a model of how a positively charged surface enhances DNA melting. The ability of the positively charged microarray surface to enhance nucleic acid melting curves was discovered by trial and error. This effect was first observed on un-blocked amine coated microarrays without knowing that the positive surface charge was important. The use of blocked epoxy microarrays with a coating of positively charged PEI confirmed the observations with unblocked amine coated slides. PEI coated microarray arrays also showed that multiple concentration of PEI ranging from 1% to 10% could produce enhanced melting curves. This indicates that multiple levels of positive charge can produce the effect and that this phenomenon and it is not limited to a single level of positive charge. Unwanted changes to the chemical surface of unblocked epoxy microarrays prevented the enhanced melting curves from occurring. This suggests that the surface chemistry is very sensitive to changes and must be carefully preserved to ensure repeatability.

The chemistry of the buffer also plays a large role in creating enhanced nucleic acid melting curves. The use of 10% 2-Mercaptoethanol in 2.5×SSC buffer completely prevents any enhanced melting curves from being detected. The buffer concentration of 2.5×SSC was selected as a starting point for all experiments. Experiments to determine the optimal SSC buffer concentration revealed that the enhanced melting curves are produced within a range of concentration that is higher than 2.5×. Early experiments with unblocked epoxy microarrays using 2.5×SSC buffer that produced enhanced melting curves, likely had a higher concentration of ions in solution. This occurred because of the evaporation of water in the buffer, due to the use of containers with poor sealing caps and a hold time of days to a week or more. Within the SSC buffer concentration range that produced enhanced melting curves, the concentration with the lower levels of ions produced the best results. This is evidenced by the graphs in FIG. 18. SSC buffer concentration of 2.9× to 3.1× all produced enhanced melting curves. However, the most effective buffer concentration is 2.9×SSC (0.435 M NaCl). This concentration not only produced graphs with easy to interpret slopes but the graphs were consistent in shape throughout the entire array. Furthermore, there appears to be a threshold between 2.8× and 2.9×SSC buffer that must be passed before any of the graphs on the microarray become enhanced. The 2.8×SSC buffer concentration produced no graphs with enhanced melting curves but the 2.9× concentration produced only graphs with enhanced slopes. When the concentration of SSC buffer is increased to 3.0× half of the probe spots on the array produced enhanced melting curves. Another increase in the buffer concentration to 3.1×SSC buffer produced a similar result and half of the probe spots on the microarray produced enhanced melting curves. A further increase of the SSC buffer concentration to 3.2× and none of the probe spots on the array produced enhanced melting curves (FIG. 18). A second threshold was passed between the SSC buffer concentrations of 3.1× to 3.2× that now prevents the enhanced melting curves.

In accordance with a preferred embodiment of the present invention, a model to describe the conditions needed to produce sharp enhanced two stepped melting curves would have two main components. These components are the surface charge of the microarray and the buffer composition. When DNA melting is done in liquid phase, which is an all liquid environment with no solid surface attachment, it is not possible to produce enhanced melting curves. Moreover, when DNA melting is done in solid phase on a microarray surface without positive charge on the surface, there are no enhanced melting curves. In both the liquid phase and solid phase without positive surface charge environments, the most prominent chemical bonds that are broken during DNA melting are the hydrogen bonds between base pairs. A depiction of the DNA melting environment for the solid phase without positive surface charge is shown in FIG. 19A. The DNA is shown as having a net negative charge due to the phosphate backbone. The target strand of DNA has a chemical dye attached which is shown as a star. Since the microarray surface is not positively charged, the negatively charged DNA is not attracted to the surface and is just tethered to the solid surface without folding over on the surface (FIG. 19A). No additional chemical interactions are taking place that would alter the kinetics of the DNA melting in this situation.

Typically, in accordance with the present invention, if DNA melting curves are performed in solid phase with a positively charged microarrays surface and the same conditions such as temperature increase rate, flow rate, and buffer composition, there would be additional chemical interactions with the negatively charged DNA. This is shown in FIG. 19B. Probes for the microarray can be attached by several chemical methods. Two of the most common methods known to those skilled in the art, are binding the DNA directly to the surface or to use linkers to tether the DNA to the microarray. The surface binding method is often used with amine microarray surface chemistry as the positively charged amine surface can attract the negatively charged DNA. The linker bound method is commonly used on epoxy coated microarray surfaces. As discussed in previous sections, both unblocked amine and unblocked epoxy surfaces have a layer of positive charge facing the DNA that can attract the DNA. This is shown in FIG. 19B as an attractive electrostatic force occurs between the DNA and positively charged surface. If the DNA is linker bound, it is expected to bend over and towards the positively charged surface due to the attraction. This is shown with a double arrow (FIG. 19B). The surface bound DNA experiences the same attractive force but is already attached to surface and does not bend over.

In solid phase DNA melting environments with positive charge on the surface, there are at least two significant chemical interactions acting on the target DNA holding it place. The target strand of DNA is shown with a chemical dye attached which is depicted as a star (FIG. 19B). This strand of DNA is bound to the complementary probe strand of DNA which is bound to the microarray surface. When the microarray surface is not positively charged (FIG. 19A) hydrogen bonding with its complementary probe hold the target strand in place. When the microarray surface is positively charged, hydrogen bonding with the complementary probe plus the attraction to the surface holds the target strand in place. When the temperature is increased during the melting process, both the hydrogen bonds with the probe and the attraction to positively charged surface must be overcome to allow the target to melt away. The additional attractive force with the surface is the fundamental difference in the chemical environments between the positively charged surface and non-positively charged surface that is responsible for changing the kinetics of the way the DNA dissociates or melts apart. In a non-positively charged surface environment, the breaking of hydrogen bonds is the principle factor that determines the kinetics of the DNA melting reaction. In this format DNA melts over a temperature range and this range is wide enough such that the melting temperature range of perfect match and one base pair mismatch targets overlap. This will not allow the detection of both species of targets when melting from the same probe spot. The temperature ranges of melting of perfect match and 1 bp mismatch do not overlap during solid phase melting on a positively charged surface. This may be due to the additional attractive force the positively charged surface places on the target DNA during dissociation. Exactly how the positive charge changes the melting kinetics may be related to the combination of hydrogen bonds with probe DNA and the attraction to the positively charge surface acts in a way that makes it slightly more difficult for dissociation to take place holding the target DNA in place longer till a slightly higher temperature is reached. Then when melting takes place, the unbinding event happens much more rapidly which in effect narrows the temperature range of melting.

Experiments have shown that the enhanced melting curves take place over a range of PEI concentrations. This indicates that they take place over a range of positive surface charge densities and are not limited to just one specific charge density. However, different PEI concentrations produced different enhanced graphs with different characteristics meaning that different levels of surface charge can produce graphs with different characteristics. In order to obtain melting curve graphs with ideal characteristics the exact level of surface charge would likely need to be determined. Moreover, although the enhanced DNA melting curves can occur with different levels of positive surface charge, there is likely a range of positive surface charge density that this effect occurs although it may be a wide range.

In accordance with the present invention, the second component needed to obtain enhanced DNA melting curves is the optimal buffer composition. It is known to those skilled in the art that SSC buffer stands for saline sodium citrate buffer and this term is used here on after. The most prominent chemical in the buffer is sodium chloride, NaCl. Increasing the concentration of NaCl in a buffer used for DNA melting can increase the Tm of the sequence being melted by acting to lessen the repulsive effects between the two negatively charged phosphate backbones. Likewise reducing the concentration of NaCl in the buffer can reduce the Tm of a particular DNA sequence by increasing the repulsive effect between the negatively charged phosphate backbones. In solution, NaCl will dissolve into the ions $Na^+$ and $Cl^-$. These ions can be attracted to chemicals of opposite charge. In a solid phase DNA melting environment with a positively charged surface (FIG. 19B), the DNA both probe and target strands are negatively charged and the microarray surface is positively charged. It is expected that the positively charged ions in solution will be attracted to the negatively charged DNA and the negatively charged ions in solution will be attracted to the positively charged surface. As the NaCl concentration in the buffer is increased, more ions in solution will be attracted to either the DNA or the charged microarray surface. As more ions are attracted, a shielding effect is expected to occur between the negatively charged DNA and positively charged surface, in which the dissolved ions of NaCl reduce the attractive force between the DNA and the positively charged surface. Therefore, the concentration of NaCl can be used as a means to modulate the attractive force between the DNA and positively charged surface. The positive charge on the microarray surface is the most important factor for producing enhanced melting curves and the level of positive charge that can produce this effect likely occurs over a range. Enhanced DNA melting curves will not be produced if the positive charge surface density is not within the appropriate range. One method for adjusting the level of surface charge on the microarray is by adjusting the level of positively charged chemical or chemicals coating the surface. This has been accomplished by using different levels of PEI on a blocked epoxy microarray. If it is not possible to alter the concentration of positive charge of the surface of the microarray, a second method of adjusting the level of positive charge on the surface of microarray is by changing the level of ions in the buffer. When SSC buffer is used, the ion combination is NaCl or $Na^+$ and $Cl^-$.

The level of positive surface charge density combined with the buffer concentration of ions work together to produce enhanced melting curves. They produce an overall level of charge attraction between the negatively charged DNA and the positively charged surface. If the level of positive surface charge density is too low to produce enhanced melting curves and cannot be increased, the buffer concentration can be decreased which can lower the level of ions in solution. Lowering the level of ions in solution can decrease the shielding effect the ions have on the attraction between the negatively charged DNA and the positively charged surface. This in turn can increase the attractive forces between the DNA and surface. If on the other hand the positive charge on the surface is too strong to produce enhanced melting curves and cannot be reduced, the buffer concentration can be increased which can increase the number of ions in solution. The increase in the number of ions in solution can increase the shielding effect and decrease the attractive forces between the DNA and the surface. In other words the concentration of the buffer can be adjusted to optimize the ability of the positively charged surface to produce enhanced melting curves. This optimization may require an increase or decrease in the level of positive surface charge on the microarray surface and can be accomplished by changing the buffer concentration.

This model for the interplay between the level of positive surface charge and the buffer concentration can be seen in FIGS. 19A-B. Melting curves performed with the 2.8×SSC buffer concentration did not producing enhanced melting curves. This is hypothesized to be due to the attractive fore between the DNA and surface being a little too strong. The use of 2.9×SSC buffer which is only 0.015 M higher in NaCl caused all probe spots to produce enhanced melting curves and it is hypothesized that the added buffer ions increased the shielding effect slightly and reduced the overall attractive forces between the DNA and positively charged surface. This new level of attraction between the DNA and microarray surface is now ideal for producing enhanced melting curves. The opposite situation can be seen at the 3.2×SSC buffer concentration. The amount of shielding from the buffer concentration is hypothesized to be too high to produce enhanced melting curves. In this situation the amount of attractive force between the DNA and positively charged surface is too weak. When the concentration of SSC buffer is reduced to 3.1×, this is hypothesized to reduce the amount of shielding taking place and increase the level of attractive force between the DNA and microarray surface. At this new buffer concentration, about 50% of the probe spots produce enhanced melting curves. The level of attractive force between DNA and the surface is not ideal but it does allow enhanced melting curves to occur. Further adjustment of the buffer concentration by lowering the ions level can produce even better results.

In yet another embodiment of the present invention, enhanced melting curves by controlling the interplay between the positively charged surface and the buffer ion concentration are disclosed. This can be a sensitive system. Earlier experiments with blocked epoxy microarray coated with PEI were able to produce enhanced meting curves but not over the whole microarray surface only part of it. It was believed that the PEI did not coat the surface evenly or washed off in certain areas. The unblocked epoxy microarrays produce more repeatable results. However, the epoxy coatings were made as an attachment surface for binding the probes molecules and not for consistency in charge density across the entire surface of the microarray. Higher quality control levels may be needed to completely optimize the unblocked epoxy microarray for melting curve analysis. Another component that may be important in optimizing the enhanced melting curve analysis is the surface charge of other parts of the microarray cassette. Experiments using PEI coated microarrays would not work after several reuses of the microarray cassette. This was thought to be due to the buildup of PEI on the internal surfaces of the cassette. Furthermore, the use of plastic cover slips on the cassette used for unblocked epoxy microarrays changed the optimal range of SSC buffer concentration needed to produce enhanced melting curves. Other factors that may be important in optimizing the melting curves are the length and sequence of the probes and target. Still another factor may be the length of the linker molecule used to attach the probe the surface of the microarray.

In summary, optimizing the ability of microarrays to produce enhanced melting curves can depend on uniformity of the surface charge density, high quality control during manufacturing, and special storage procedures to preserve the surface chemistry. The interplay between the positively charged surface and the concentration of ions in solution is very sensitive and requires that the buffer concentration be adjusted to each microarray surface chemistry used. In addition, buffer concentrations may also need to be optimized for surface charge density of the cassette material, the sequence and length of both probes and target DNA, and the length of the linker molecule used to attach the probe to the microarray surface. Previously, it is known to those skilled in the art that liquid phase DNA melting curves typically are not able to produce enhanced melting curves. Furthermore, the use of a positively charged microarray surface is counterintuitive. A positively charged microarray surface is known to cause nonspecific binding with target DNA and increases the levels of background noise which is why blocking of the microarray surface is performed before hybridization. However, when using an unblocked positively charged microarray surface for enhanced melting curve analysis, analyzing software can subtract the amount of background noise from the signal giving a relatively accurate result.

FIGS. 20A-C depict an overview of the KRAS Mutation Assay. The KRAS gene is an oncogene that codes for the K-Ras protein. K-Ras is a GTPase in a signal transduction pathway known as the RAS/MAPK pathway. This pathway controls cell growth, division, and differentiation. Mutations in the KRAS gene can cause an activating mutation in the GTPase protein, causing the enzyme to be always activated.

This in turn can cause disregulation in the RAS/MAPK pathway leading to abnormal cell behavior with the potential to cause cancer. Activating mutations in KRAS can occur in codons 12 and 13. A class of cancer treatment drugs known as epidermal growth factor receptor (EGFR) inhibitors, work by blocking the receptor and interfering with the growth and cell division of cancer cells. K-Ras is a downstream component of the signal transduction pathway activated by the EGFR. If mutations occur in KRAS that cause the protein to be always activated, the signal transduction pathway will be always on and EGFR inhibitor drugs will no longer work. In order to determine if a cancer patient may respond to EGFR inhibitors, a KRAS mutation test must be given. If KRAS activating mutations are present the patient is not likely to respond to EGFR inhibitors. And if KRAS is not mutated then the patient is likely to respond to EGFR inhibitors.

There are a total of 12 different activating mutations that can occur in KRAS, 6 mutations in codon 12, and 6 mutations in codon 13 (see FIG. 20A). KRAS mutations can be detected by DNA sequencing which includes both Sanger sequencing and targeted next generation sequencing methods. DNA sequencing costs have had an astounding drop over the last 10 years but the price per test of older technologies such as PCR and microarray analysis are still more cost effective. Methods of analysis for KRAS mutations that use hybridization and melting are not able to reliably detect each of the 12 mutations in the 6 base pairs of codons 12 and 13. Several KRAS mutation diagnostic kits are commercially available and FDA approved in the United States, however, they are only able to detect the presence of a mutation and not confirm the sequence of the mutation. Technology involving kits using PCR followed by liquid hybridization are known to exist, however, these kits are only able to detect a change from the wild type sequence but are not able to determine which mutation is present. Other technology utilizes assays using PCR followed by a liquid phase DNA melting assay. Although these assays are able to detect a change from the wild type sequence, they are not able to determine the sequence of the mutation. Confirming the changes in KRAS sequence is important during cancer treatment. Additionally, it would be beneficial to address the question, that if a cancer patient responds to treatment only to have a reoccurrence of cancer later in life, is this a new cancer or the reoccurrence of an old cancer coming back?DNA sequence data would be needed to address and solve the aforementioned question.

The microarray assay is a type of hybridization assay and in its current evolution is unable to detect and confirm the presence of all of the 12 different activating mutations that can occur in KRAS. The detection of activating mutations in KRAS is challenging due the close proximity of codons 12 and 13. Up to 12 different mutations can occur within 6 base pairs. A probe molecule designed to capture the KRAS sequence works best if it overlaps both upstream and downstream of the mutation. Hybridization can detect a mutation within the region of the probe binding the target but is not be able to distinguish which base is mutated, only that a mutation is present. This is the same capability of the commercially produced KRAS mutation tests. Using 12 or more probes to detect all the different mutations is possible but problematic since the probes have the tendency to bind both the perfect match and mismatched target at the same time. A patient heterozygous for a certain mutation would have 2 different target sequences in the sample, wild type and mutant. Both can bind the microarray but the difference in affinity each target has for the probe is small. Therefore, the level of fluorescence intensity is used to determine how much wild type and mutant target have bound. If a particular probe spot for 1 of the 12 mutants is higher in fluorescence intensity this would indicate that this particular mutation is present. The difficulty arises when multiple probe spots have similar levels of intensity. In this situation it becomes impossible to determine which mutation is the real mutation present.

Figure 21:
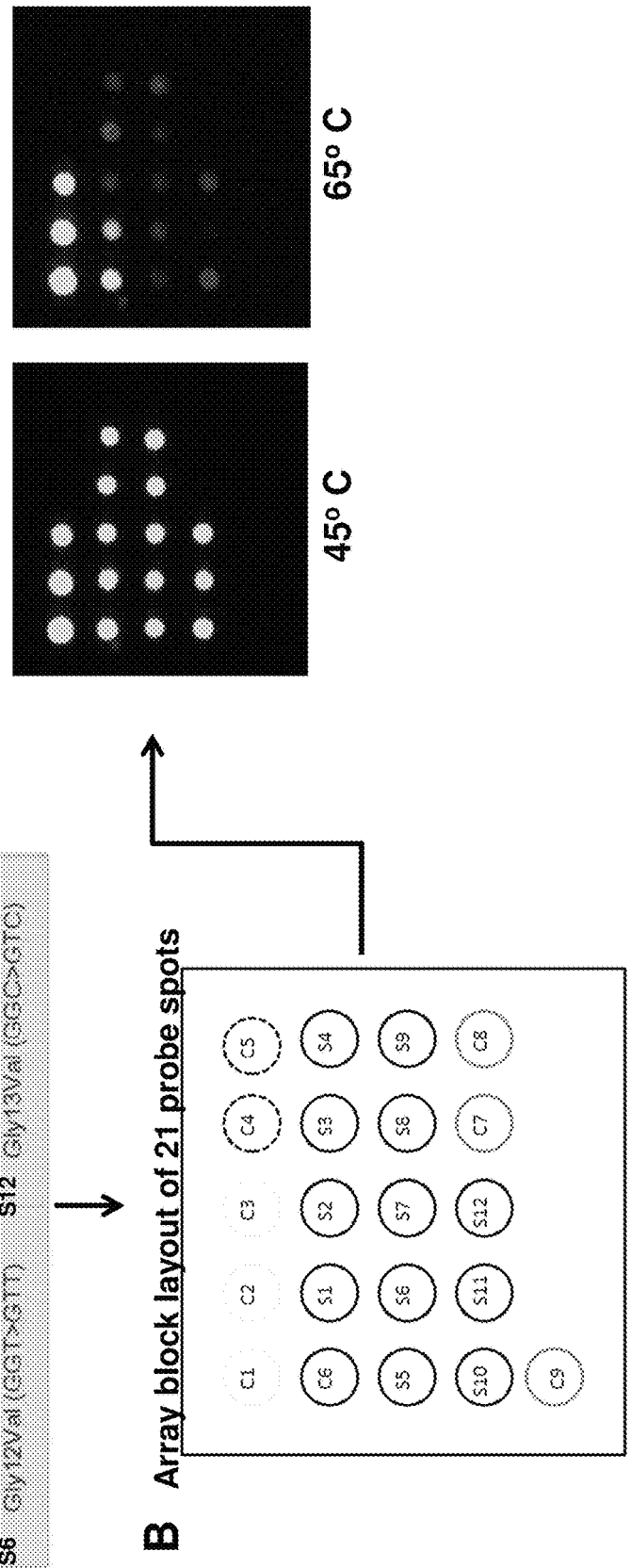
FIG. 21 illustrates the exemplary results of the KRAS Mutation Assay according to the present invention.

Melting curve analysis in a microarray format is one method to solve this problem. When a positively charged microarray surface is used with the optimal buffer ion concentration, the technique should be able to detect the presence of wild type target and mutant with high levels of both sensitivity and specificity. Custom fabricated microarrays were ordered from Microarray Inc. with the instructions to pack each microarray in an individually sealed vacuum bag with either argon or nitrogen gas in a glove box. Custom 25 bp target DNA oligos were ordered for wild-type and a codon 12 mutant (GGT>AGT) given the identification code S1 (FIG. 21A). Experiments were conducted following a similar protocol used for epoxy coated unblocked microarrays. The range of SSC buffer concentrations used was 2.4× to 3.3×. A flow diagram labeled in FIGS. 21A-C shows the layout of the microarray and results of an experiment performed with 2.6×SSC buffer. FIG. 21A is a table showing all the 12 activating mutation of codons 12 and 13 and an identification code given to each mutations ranging from S1 to S12. FIG. 21B shows the layout of the microarray. Probe spots C1 to C3 are positive CY3 dye controls ranging from 20M to 5M in concentration. Spots C4 and C5 are negative controls. Probe spot C6 is the wild type sequence and S1 to S12 are the mutant probe spots. Probe spots C7 to C9 are CY5 dye positive control spots but the excitation wavelength to excite this dye was not used.

Figure 22:
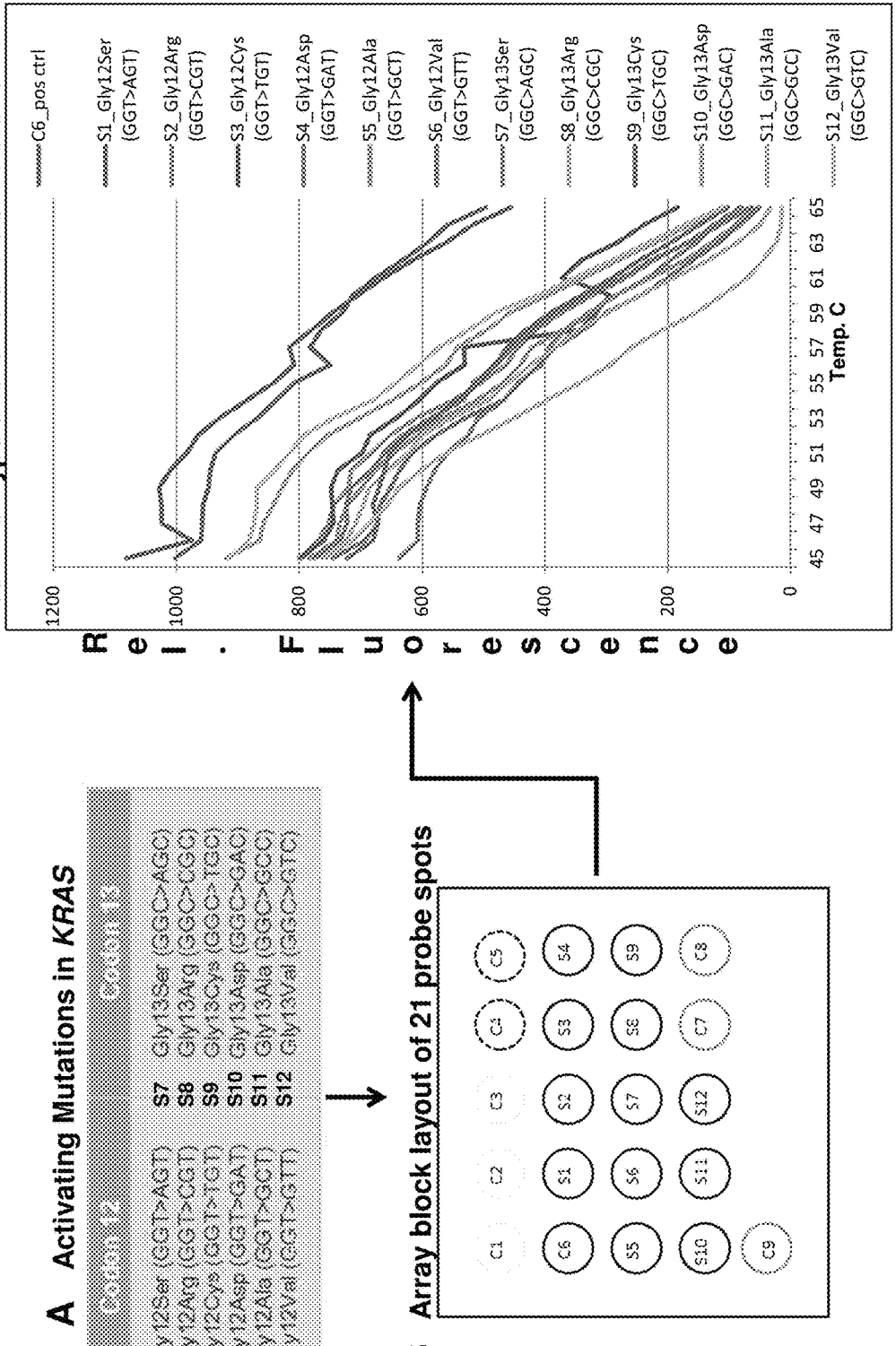
FIG. 22 illustrates the exemplary results of the KRAS Mutation Assay according to the present invention.

The first set of results for the KRAS mutation assay are shown in FIG. 22C. The pictures are scans at different temperatures. The scan at 45° C. was the very start of the experiment. Using FIG. 21B as a guide, positive control spots C1 to C3 all fluoresced brightly. Negative controls spots C4 and C5 do not fluoresce at all. Positive control C6 and mutants S1 to S12 all fluoresce brightly. Differences in the measured fluorescence intensity between spots were observed but these differences were relatively small. Using the naked eye it is not possible to determine which mutations is present since all mutant probes spots display a fluorescence signal of similar intensity. This is the type of result a standard microarray would produce. As the temperature was raised 1° C. a new scan was completed. The cycles of temperature increase and scans continued until the last scan of 65° C. The scan of 65° C. is shown in FIG. 21C right side. At this temperature all 3 positive control spots C1 to C3 are fluorescing and none of the negative control spots are fluorescing. The wild type probe spot C6 is fluorescing and mutant S1. All other mutant probe spots are not fluorescing and the slight signal emitted is a residual background signal. So, FIG. 21C at 65° C. produces a correct answer in that sample had two targets present, wild type and S1 which is mutation in codon 12 of the first base.

FIGS. 22A-C depicts results of the KRAS Mutation Assay. A more detailed analysis of the results is shown in the graph of FIG. 22C. This graph shows probe spots C6 to S12 and all data is raw non-normalized. Positive controls C1 to C3 showed relatively constant fluorescence over the 45° to 65° C. temperature range and was not included in the graph. To help interpret the graph the table of activating mutations is shown in FIG. 22A and microarray layout in FIG. 22B. There are so many graphs depicted in one figure that interpretation is difficult. However, the most obvious observation is that the curves of C6 and S1 have a slightly higher starting intensity, have a step in the graph where the slope become flat, and that the fluorescence has not gone to zero at 65° C. but is about half the starting intensity. A better analysis of the data can be made by dividing the melting curves up by both codon and the base within each codon.

Figure 23:
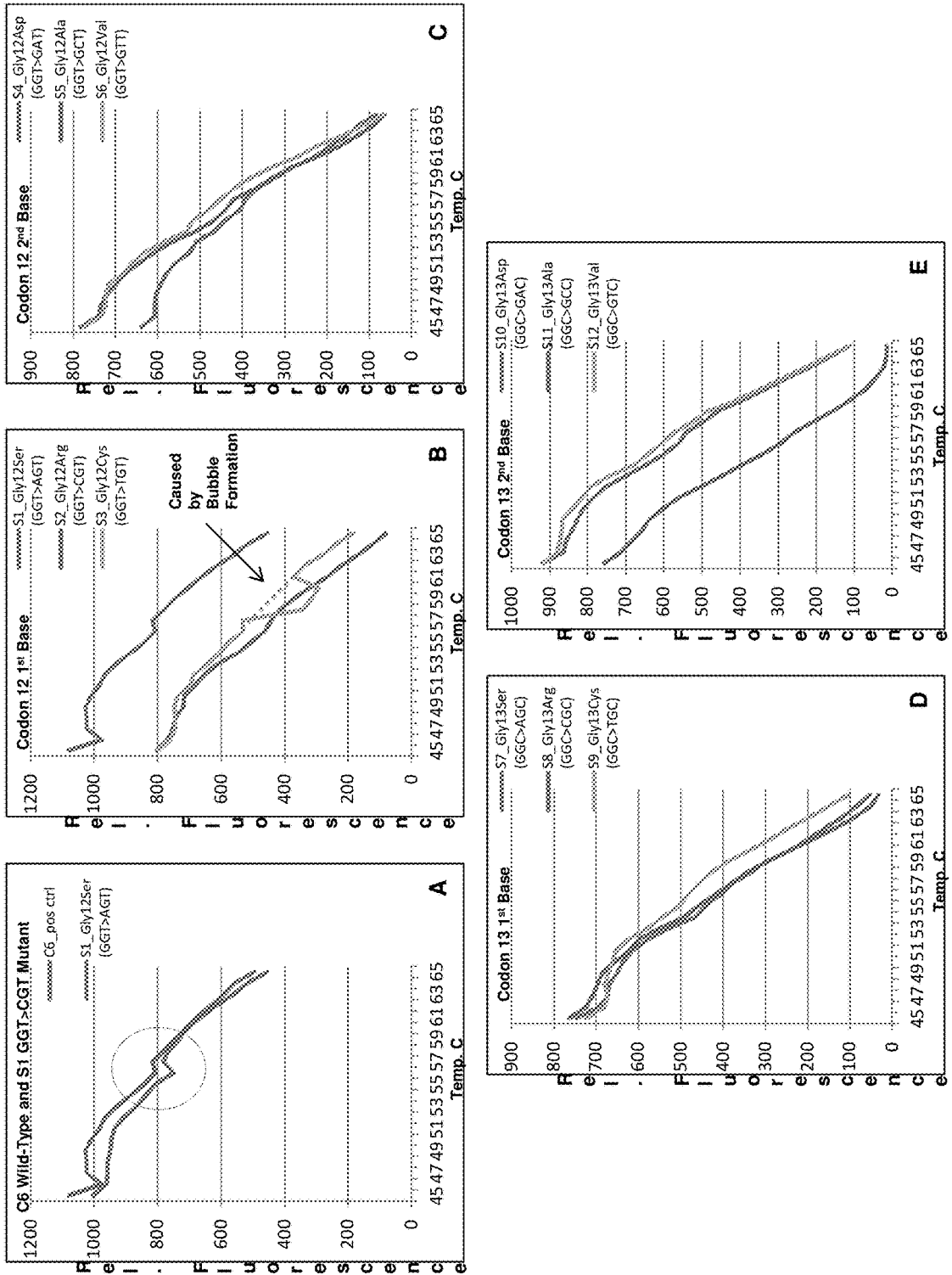
FIG. 23 illustrates the exemplary results of the KRAS Mutation Assay by Codon according to the present invention.

FIGS. 23A-E depict results of the KRAS Mutation Assay by Codon in 5 different graphs. As seen in FIG. 23A, Graph A shows the melting curves of both C6 wild type and the S1 mutant. These slopes are relatively similar with a flat step at about the half-way point marked with a dashed circle. Both graphs have a similar starting intensity and the ending intensity is almost the same at about half the stating intensity. The first half of both graphs is the melting of one base pair mismatch and the second part of the graph is the melting of perfect match. For the C6 probe, perfect match is the wild type target and mismatch is S1 target which can bind a one base pair mismatch. For the S1 mutant probe, perfect match is the S1 mutant target and mismatch is the wild type sequence which can bind as a 1 base pair mismatch. The graphs of melting curves of codon 12 with mutations in the second base position are shown in FIG. 23C. All three melting curves for probes S4, S5, and S6 show similar melting curves without a flat section in the graph to indicate the presence of 2 different target sequences binding the same probe and then melting away. The fluorescence intensity of the three melting curves is below 100 relative units at 65° C. indicting that almost all of the target melted away except for the residual background still bound to the glass. The wild type target would bind mutant probes S4, S5, and S6 as a 1 base pair mismatch. The S1 mutant target has a mutation in codon 12 first base. If S1 target had bound any of the S4, S5, or S6 probes it would bind as a 2 base pair mismatch since these probes have mutations in the second base of codon 12. However, there is no major change in the slope of the melting curves to form a flat section for any of the graphs in FIG. 23C. It can be inferred that the 1 base pair mismatch target wild type bound the probes and that the 2 base pair mismatch S1 did not bind any probes. The hybridization temperature was 45° C. and this was likely too high to allow 2 base pair mismatches to bind.

The graphs of melting curves of probes for codons 13 with mutations in the first base are shown in FIG. 32D and the graphs of melting curves of probes of codon 13 with mutations in the second base are shown in FIG. 23E. The melting curves of probes for codons 13 both first and second bases all show a sloped line with no flat section in the middle of the curve indicating that one type of target bound the probes and melted away. The wild type target binds all probes as a 1 base pair mismatch. If the S1 target bound any of the probes it would bind as a 2 base pair mismatch since S1 has a mutation codon 12 of the first base position. However, there are no changes of slope or a flat section in the melting curve to indicate that more than one type of target bound any of the probes in FIGS. 23D and 23E. It can be assumed that the S1 mutant target did not bind any of the probes since it is a 2 base pair mismatch and that only the wild type target bound as a one base pair mismatch. Again the hybridization temperature of 45° C. was likely too high to allow a 2 base pair mismatch to bind. Also, the ending relative fluorescence intensity for all graphs (FIGS. 23D and 23E) is about 100 relative units or lower. This indicates that most of the targeted melted away leaving residual background. This is in contrast to the probes with perfect match Interpretation of the melting curve graphs confirms that the correct result of the assay is that wild type and S1 mutation DNA were present. A range of SSC buffer concentrations were tried but only the 2.6×SSC buffer concentration produced good results. This is in contrast to other experiments with unblocked epoxy microarray slides that demonstrated that there was a small range of buffer concentrations that were able to produce enhanced melting curves. After a communication with the manufacturer of the microarrays, it was learned that the microarrays were packaged by purging the vacuum bag with nitrogen and not by sealing the bag in a glove box with nitrogen. This is a significant difference in the protocol. It is likely that a mixture of nitrogen and room air was sealed in the vacuum bags. This may have caused unwanted chemical reactions with the microarray surface that could negatively impact the melting curve results. More experiments using PCR amplified KRAS samples from real cancer patients were going to be attempted. However, because of the difficulty of doing the assay with the current batch of microarrays, it was not performed. Better results can likely be obtained by using a fresh batch of microarrays that are packaged in a glove box with an inert gas.

Figure 24:
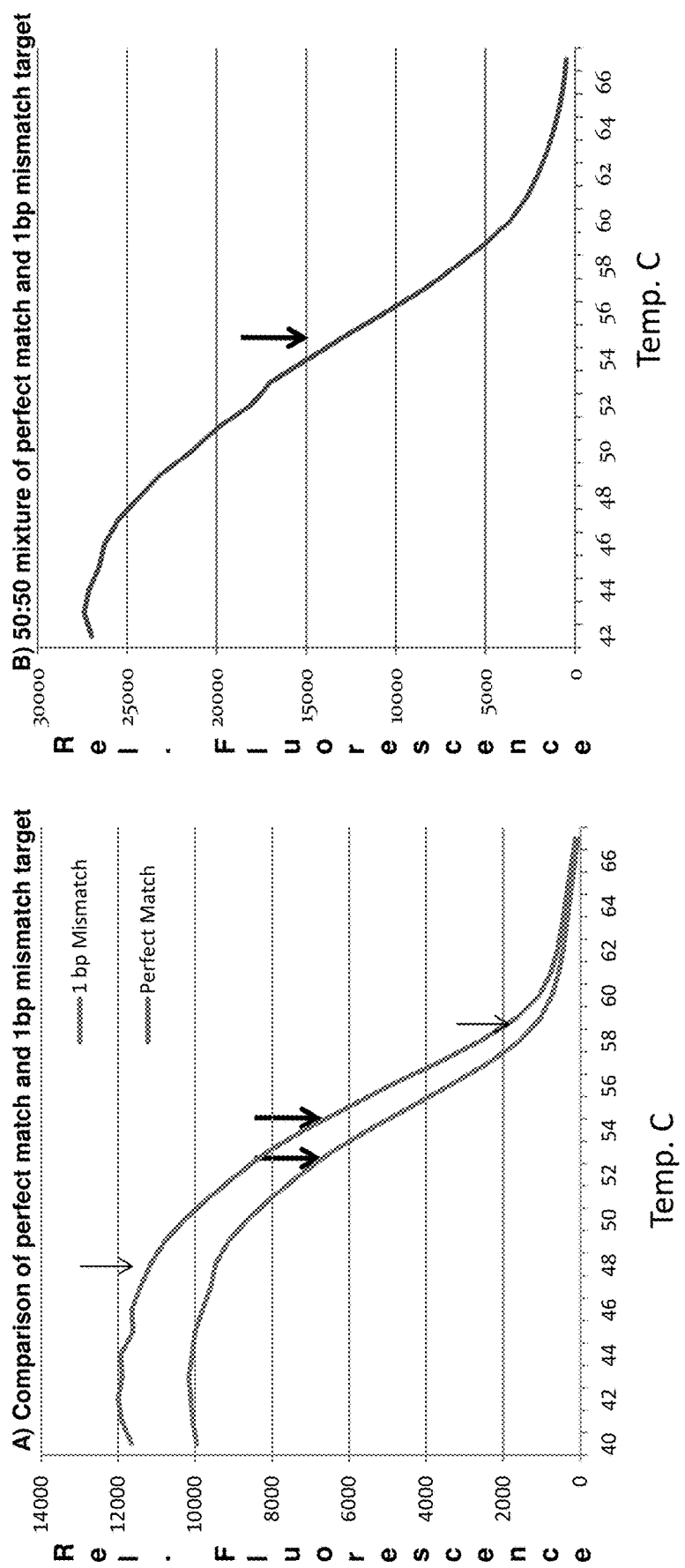
FIG. 24 illustrates the DNA Melting Kinetics on Standard Microarray surface chemistry.

FIGS. 24A-B depict the DNA Melting Kinetics on Standard Microarray surface chemistry. In order to demonstrate the increased specificity of binding that occurs in the presence of a positively charged surface, a review of the principles of specificity and sensitive of hybridization and melting on a standard non-positively charges surface must be described. The characteristics of sensitivity versus specificity during DNA hybridization is a tradeoff. This tradeoff is best demonstrated in FIGS. 24A and 24B. FIG. 24A is a DNA melting curve on a blocked epoxy microarray slide. The microarray was printed with 25 bp probes to capture a perfectly matched target and probes to capture a 1 base pair mismatched target. So, a 1 bp mutation was built into some of the probe molecules. The target was a perfectly matched sequence of 25 bp (Table 2). The melting curves for a perfectly matched probe and 1 bp mismatched probe are displayed together. Both curves display a classic ski slope shape with flat section at the lower temperature range and then a slope. The Tms of both slopes are distinctly different. The Tm for the perfectly matched probe is approximately 55° C. and the Tm for 1 bp mismatch is approximately 53° C. However, the melting temperature ranges of the perfect match probe and 1 bp mismatch overlap significantly. The temperature range of melting for the perfectly match probe is approximately 49° C. to 60° C. and the temperature range of melting of the 1 bp mismatch is approximately 48° C. to 59° C.

Since the temperature ranges of melting of perfectly matched probe and 1 bp mismatch overlap, there is no hybridization temperature which can produce maximum levels of both sensitivity and specificity. If high levels of sensitivity for the binding of target to the perfectly matched probe are desired, the optimal hybridization temperature is 49° C. or lower. This is marked with an arrow in FIG. 24A. However, hybridizing at this temperature can also allow significant amounts of target to bind the 1 bp mismatch probe reducing the level of specificity. If high levels of specificity are desired, the optimal hybridization temperature needs to be higher. At a hybridization temperature of 59° C. (marked with an arrow in FIG. 24A), the amount of target that binds the 1 bp mismatched probe is much less but also the total amount of target that binds the perfectly matched target is less reducing sensitivity. There is no single hybridization temperature that is optimal for obtaining maximum levels of both specificity and sensitivity. Furthermore, increases in specificity or sensitivity of binding that occur from the adjustment of NaCl concentrations in the buffer produce similar results. Decreasing the concentration of NaCl in the buffer increases the repulsive forces between the negatively charged phosphate backbones of the DNA double helix and destabilizes the structure. This lowers the Tm and increases the specificity of binding at a temperature below the Tm but also lowers the sensitivity of binding at the same time. And vice versa, increasing the NaCl concentration can stabilize the double stranded DNA and raise the Tm. This has the effect of increasing the sensitively of binding at temperatures below the Tm but also reducing the specificity of binding. There is no NaCl concentration that can produce both maximum levels of sensitivity and specificity at the same time. When a 50:50 mixture of perfectly matched target and 1 bp mismatched target are allowed to hybridize a perfectly match probe and then melt away from a blocked epoxy microarray, the result is shown in FIG. 24B. There is a ski slope melting curve with no change in the slope of the graph to indicate the presence of two different targets melting away. It might be mistakenly assumed that there is only one type of target melting away with the Tm marked by an arrow. This result is occurring because the temperature ranges of melting for perfect match and 1 bp mismatch overlap. There is never a point in the graph when 1 bp mismatch has completed its melting and there is a short period of no melting before the perfectly matched target begins to melt away. Rather the 1 bp mismatch and perfect match are melting at the same time. Furthermore, this result demonstrates that there is no temperature for the hybridization of perfectly match target that can result in maximum levels of both sensitivity and specificity when a mixture of perfectly matched and 1 bp mismatched target are present together and hybridized at the same time.

New Directions and Future Applications of the Technology

Solid phase melting curves on a positively charged surface can narrow the temperature ranges of melting of perfect match and mismatch so that these ranges no longer overlap. When the temperature ranges of melting no longer overlap, both perfect match and mismatch can be easily detected binding the same probe by melting curves. Being able to detect and confirm the presence of perfectly matched target and mismatched target DNA binding a probe spot increases the accuracy of any test being performed. With the help of DNA melting curve analysis, diagnostic tests such as the KRAS mutation assay can now be performed with a high level of accuracy not possible using a standard microarray hybridization without DNA melting. One of the most interesting findings of the KRAS test was the ability of the positively charged surface to separate the temperature ranges of melting enough that at higher temperatures only perfectly matched target still remain bound to the microarray. This result is shown in FIG. 21C. At the lower temperature of 45° C. all test probe spots C6 to S12 have similar levels of fluorescence that cannot be distinguished by visual examination with the naked eye. When the temperature is raised to 65° C. at the end of the experiment, only perfectly matched target remains bound to the wild type C6 and mutant S1 probes. This result implies that the positively charged surface can not only enhance melting curves reactions but can serve as a method to improve the specificity of any hybridization reaction.

Figure 25:
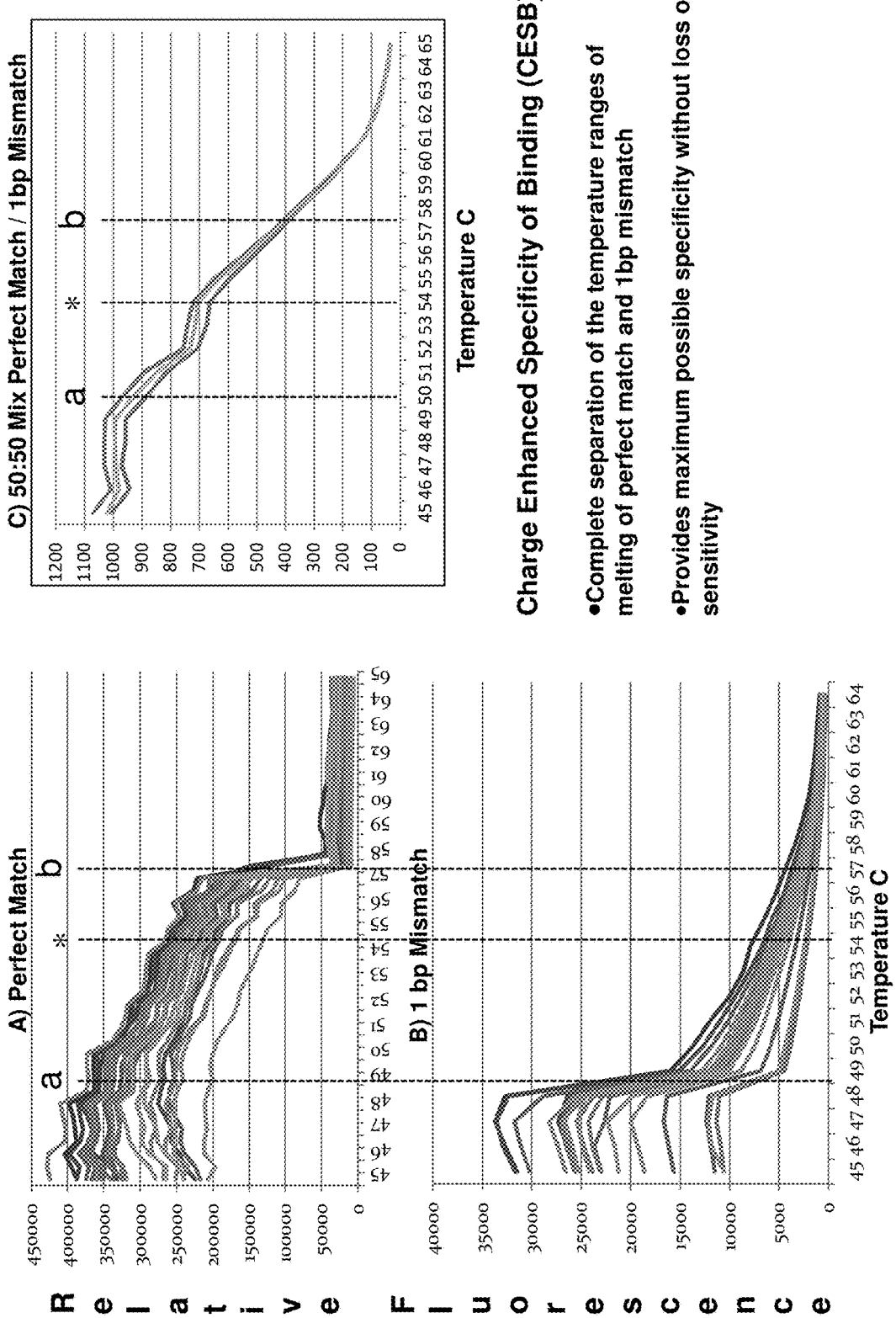
FIG. 25 illustrates exemplary results of DNA melting curves obtained from optimized charge enhanced specificity surface chemistry according to a preferred embodiment of the present invention.

FIGS. 25A-C depict DNA melting curves obtained from optimized charge enhanced specificity surface chemistry. When a positively charged microarray surface is used, the temperature ranges of melting for perfectly matched target and 1 bp mismatched target no longer overlap. This is shown in FIGS. 25A, 25B, and 25C graphs that shows graphs of melting curves generated on unblocked epoxy microarray slides. FIGS. 25A and 25B show the melting curves for perfectly matched and 1 bp mismatched target respectively. In both graphs multiple probe spots were graphed which had an identical sequence. The stacked line function of the graphing software was used to spread out the lines so that they did not lie directly on top of each other. The loss of fluorescence in the graph as shown in FIG. 25A in the early part of the graph is due to photo bleaching because no adjustment of gain was used to compensate. The Tm for perfectly matched target in FIG. 25A is 57° C. and is marked by line b. The Tm of 1 bp mismatch is about 49° C. and is marked by line "a" in FIG. 25B. The difference in temperature in Tms between the perfectly matched target and 1 bp mismatched targeted is approximately 8 degrees C. These two graphs show how the positive charge of the microarray surface has narrowed the temperature ranges of melting so that neither overlaps.

FIG. 25C shows the melting curve of a 50:50 mixture of perfectly matched target and 1 bp mismatch target. This melting curve of 3 probe spots is an enhanced melting curve with two Tms. The Tm for 1 bp mismatch is approximately 50° C. and is marked by line a and the Tm for the perfectly matched target is approximately 57° C. and is marked by line b. The temperature difference between Tms is 7° C. The narrowing of the temperature ranges of melting for both the perfectly matched and 1 bp mismatched target is significant but not as narrow as when either sample is tested alone. However, the narrowing is sufficient to create a change of slope in the graph also called a step which marks the high end of the temperature range of melting of the 1 bp mismatch and the low end of the temperature range of melting of the perfectly matched. This change of slope is not only important as a marker of the temperature ranges of melting of the two target types but also creates a temperature of hybridization that can allow maximum levels of specificity for the detection of perfectly matched target without any loss of sensitivity of detection. This temperature would be approximately 54° C. and is marked with a star. It is only possible to create these conditions with a positively charged surface and a blocked epoxy microarray surface will not narrow the temperature ranges of melting of the targets so they no longer overlap (FIG. 24B). The advantages of using the positively charged microarray surface not only create an enhanced melting curve that can detect the binding and melting of perfectly matched and 1 bp mismatched target, but also create conditions that separate the temperature ranges of melting leading to a temperature of hybridization with maximum levels of specificity for the detection of perfectly matched target DNA without loss of any sensitivity. This novel discovery is termed "Charged Enhanced Specificity of Binding" (CESB).

FIGS. 26A-C depict binding mechanisms of liquid phase and solid phase PCR. Charge enhanced specificity of binding can be used to improve the specificity of any hybridization reaction provided the reaction can be done in a solid phase format. A list of techniques that would benefit from CESB may include but is not limited to southern blots, northern blots, microarray, PCR and some forms of next generation DNA sequencing with a hybridization step. It is well known to those skilled in the art that PCR is one of the most commonly used methods in the life sciences, and the specificity enhancement is the preferred method according to an embodiment of the present invention. Typically, PCR is a liquid phase reaction and has 3 steps per cycle as shown in FIG. 26A. The second step of PCR is called the annealing step and has the most potential for mis-binding target DNA with a similar sequence but is not a perfectly matched sequence. It is known to those skilled in the art, that most of the errors that occur during PCR occur at the annealing step. If PCR could be changed into a solid phase assay, CESB could be applied which in turn would improve the accuracy of PCR by preventing any mis-binding during annealing. A form of solid phase PCR does exist and has been called "Bridge Amplification" or "Bridge PCR" as shown in FIG. 26B. In this format all 3 steps per cycle of PCR occur on a solid surface which can be flat or round in the shape of a micro bead. Since the target is bound to the surface (FIG. 26B, a) it can only bind a primer within reach (FIG. 26B, b). If the primer binds its target in the presence of a positively charged surface, with the optimal level of buffer ions, and at the predicted temperature where the temperature ranges of melting of perfect match and 1 bp mismatch do not overlap, then maximum specificity of hybridization without loss of sensitivity would take place. As amplification continues, there is a buildup of PCR product near the area where the first PCR cycle took place called a DNA colony. As more PCR cycles are completed, the larger the colony becomes. One limitation of this method is that logarithmic amplification of target may not be possible in the later cycles of PCR if the primer in a particular surface area is depleted. Another limitation is the need to remove the PCR product from the solid surface for further analysis which would require cleaving it from the surface. This adds an additional step to the procedure.

The development of a hybrid liquid phase solid phase hybridization procedure would permit the increased specificity of CESB with the flexibility of a liquid phase protocol. This could be achieved by taking the large surface area of the microarray and converting this to thousands, millions, or even billions of positively charged nano-particles each attached to their own PCR primer or probe molecule. This would allow the DNA portion of the structure to freely move in liquid phase while still retaining the ability to undergo CESB with its target since the positively charged nano-particle is present.

FIGS. 27A-C depicts a custom synthesized oligo bound to a nano particle. In FIG. 27A an example of a nano-particle attached to an oligo is as a probe or primer that is attached to a positively charged nano-particle by a flexible cleavable linker molecule. In an actual hybridization application, the probe primer section is predicted to be attracted to the positively charged nano-particle and form a hair pin like structure. In a liquid phase PCR application the double stranded section of primer and target DNA is predicted to bend and be attracted to the positively charged nano-particle as shown in FIG. 27B. In this configuration, the specificity of binding can be improved by CESB provided by the positively charged particle. The positively charged nano-particle primer is intended for liquid phase applications. However, this structure can also be adapted to solid phase applications. The same nano-particle probe can be attached to a solid surface with a linker as shown in FIG. 27C. The advantage of using this combination of nano-particle and probe is that the probe brings along its own positively charged surface. This eliminates the need for special chemical coatings on the microarray slides to produce the positive charge and simplifies the microarray fabrication procedure. Regardless if the charged nano-particle is used as a PCR primer or probe, the positively charged nano-particle can be removed by cleaving the flexible linker. The removal of the nano-particle may be needed in special applications such as a PCR reaction when the PCR product is further analyzed by DNA sequencing or cloned into a plasmid.

FIG. 28 depicts a schematic of hybrid liquid-solid phase PCR. An example of how the nano-particle PCR primer operates in a hybrid liquid-solid phase PCR reaction is shown involving three steps. During step 1 of denaturation, double stranded DNA is melted into single strands. During step 2 primer annealing, the nano-particle primers bind the 3' end of the target strand of DNA which puts the primer in a 5' to 3' orientation and ready for primer extension. This annealing step is able to use CESB conditions since the positively charged nano-particle is present with optimal ion buffer concentrations. Under these conditions the annealing temperature can be higher than classical PCR and prevent the binding of any 1 bp mismatch target without loss of PCR sensitivity. During step 3 elongation, polymerase can extend the PCR primers in the 5' to 3' direction creating a complimentary strand of DNA. In the next cycle of PCR the 3 steps are repeated. Some of the target DNA may have nano-particle attached to the 5' end of the target strand of DNA. This does not create a problem since the nano-particle primer attaches to the 3' and of the target DNA. So as more PCR cycles are completed more target DNA can have the nano-particle attached to the 5' terminus. When the PCR reaction is complete, removal of the nano-particle may or may not be needed. If it is necessary to remove the nano-particle from the target before further analysis (e.g. DNA sequencing or cloning), a chemical method to cleave the linker section of the nano-particle can be used. There are a variety of linker chemistries and chemical cleavage methods to accomplish this task. Then differential centrifugation can be used to separate the nano-particle from the DNA. The key advantages of the hybrid liquid-solid phase PCR method are the maximized specificity of amplification and the greater flexibility of primer design. Since CESB is increasing the specificity of binding and 1 base pair mismatched target cannot bind, the criteria for primer design can be relaxed to allow for primers that have as little as a 1 bp different in sequence.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

What is claimed is:

1. A method to enhance inter-nucleic acid binding at the surface of a solid, to detect the presence of wild type and mutations of the KRAS gene, the method comprising:
   exposing the surface with a first solution sufficient to attain a positively charged surface;
   exposing a first nucleic acid solution comprising a first nucleic acid to the positively charged surface to produce a first nucleic acid bound positively charged surface;
wherein the first nucleic acid comprises at least two probes, a first probe comprising wild type KRAS genes and a second probe comprising mutant KRAS genes;
whereby the mutant KRAS gene comprises at least one of 12 different activating mutations in KRAS codons 12 and 13;
   exposing a second nucleic acid solution comprising a second nucleic acid to the first nucleic acid bound positively charged surface to produce a hybridized nucleic acid pair;
whereby the second nucleic acid solution comprises a test sample from a patient;
   heating the hybridized nucleic acid pair sufficiently to reveal a bi-phasic melting curve shape;
   wherein the first solution further includes an ionic buffer, the ionic buffer comprises an ion concentration sufficient to provide a shielding effect and modulates hydrogen bond attraction between the first nucleic acid bound positively charged surface and the second nucleic acid;
   wherein the positively charged surface of the solid changes the kinetics by lowering melting temperature (Tm), narrowing the temperature range of melting between one basepair mismatch and perfect match to detect the presence of wild type and mutations of the KRAS gene in the test sample;
   wherein the temperature is sufficient at a temperature high enough such that only the perfect match hybridizes.

2. The method of claim 1, wherein the first solution comprises a positively charged chemical selected from the group consisting of polyethyleneimine, epoxide, amine and any chemical compound with a positive charge.

3. The method of claim 2, wherein the positively charged chemical is polyethyleneimine.

4. The method of claim 3, wherein the polyethyleneimine is present in the amount from about 1% to about 10% vol/vol.

5. The method of claim 1, wherein the solid is selected from the group consisting of polystyrene, microbeads, glass, metal, charcoal, colloidal gold, bentonite, polypropylene, plastics and silica.

6. The method of claim 5, wherein the solid is a glass.

7. The method of claim 6, wherein the solid is a glass slide.

8. The method of claim 7, wherein the micro array glass slide comprises from about 10 to about 4.2 million probes.

9. The method of claim 1, wherein the first nucleic acid includes a label.

10. A method to enhance inter-nucleic acid binding at the surface of a solid, to detect the presence of wild type and mutations of the KRAS gene, the method comprising:
    exposing the surface with a first solution sufficient to attain a positively charged surface;
    exposing a first nucleic acid solution comprising a first nucleic acid to the positively charged surface to produce a first nucleic acid bound positively charged surface;
wherein the first nucleic acid comprises at least two probes, a first probe comprising wild type KRAS genes and a second probe comprising mutant KRAS genes;
whereby the mutant KRAS gene comprises at least one of 12 different activating mutations in KRAS codons 12 and 13;
    exposing a second nucleic acid solution comprising a second nucleic acid to the first nucleic acid bound positively charged surface to produce a hybridized nucleic acid pair;
whereby the second nucleic acid solution comprises a test sample from a patient;
    wherein the first solution further includes an ionic buffer, the ionic buffer comprises an ion concentration sufficient to provide a shielding effect and modulates hydrogen bond attraction between the first nucleic acid bound positively charged surface and the second nucleic acid; and,
    heating the hybridized nucleic acid pair at a temperature sufficient to induce specificity wherein the positively charged surface of the solid changes the kinetics by lowering melting temperature (Tm), narrowing the temperature range of melting between one basepair mismatch and perfect match to detect the presence of wild type and mutations of the KRAS gene.

11. The method of claim 10, wherein the first solution comprises a positively charged chemical selected from the group consisting of polyethyleneimine, epoxide, amine and any chemical compound with a positive charge.

12. The method of claim 11, wherein the positively charged chemical is polyethyleneimine.

13. The method of claim 12, wherein the polyethyleneimine is present in the amount from about 1% to about 10% vol/vol.

14. The method of claim 10, wherein the solid is selected from the group consisting of polystyrene, microbeads, glass, metal, charcoal, colloidal gold, bentonite, polypropylene, plastics and silica.

15. The method of claim 14, wherein the solid is a glass.

16. The method of claim 15, wherein the solid is a glass slide.

17. The method of claim 16, wherein the micro array glass slide comprises from about 10 to about 4.2 million probes.

18. The method of claim 10, wherein the first nucleic acid includes a label.

* * * * *

SEQUENCE LISTING

<160> NUMBER OF SEQ ID NOS: 19

<210> SEQ ID NO 1
<211> LENGTH: 25
<212> TYPE: DNA
<213> ORGANISM: Escherichia coli

```
<220> FEATURE:
<221> NAME/KEY: misc_feature
<223> OTHER INFORMATION: Cy3 Dye Control E. coli Ecs2686 Flagellar
      Biosynthesis Gene

<400> SEQUENCE: 1
tcttattcag cctgactggt gggaa                                            25

<210> SEQ ID NO 2
<211> LENGTH: 25
<212> TYPE: DNA
<213> ORGANISM: Mus
<220> FEATURE:
<221> NAME/KEY: misc_feature
<223> OTHER INFORMATION: Mouse GAPDH Gene Antisense Control

<400> SEQUENCE: 2
tgacaatctt gagtgagttg tcata                                            25

<210> SEQ ID NO 3
<211> LENGTH: 25
<212> TYPE: DNA
<213> ORGANISM: Mus
<220> FEATURE:
<221> NAME/KEY: misc_feature
<223> OTHER INFORMATION: Mouse GAPDH Gene

<400> SEQUENCE: 3
tatgacaact cactcaagat tgtca                                            25

<210> SEQ ID NO 4
<211> LENGTH: 25
<212> TYPE: DNA
<213> ORGANISM: Mus
<220> FEATURE:
<221> NAME/KEY: misc_feature
<223> OTHER INFORMATION: Mouse GAPDH Gene Antisense One bp Mismatch

<400> SEQUENCE: 4
tgacaatctt gaatgagttg tcata                                            25

<210> SEQ ID NO 5
<211> LENGTH: 25
<212> TYPE: DNA
<213> ORGANISM: Homo sapiens
<220> FEATURE:
<221> NAME/KEY: misc_feature
<223> OTHER INFORMATION: KRAS Wild Type

<400> SEQUENCE: 5
gttggagctg gtggcgtagg caaga                                            25

<210> SEQ ID NO 6
<211> LENGTH: 25
<212> TYPE: DNA
<213> ORGANISM: Homo sapiens
<220> FEATURE:
<221> NAME/KEY: misc_feature
<223> OTHER INFORMATION: Mutation  Gly12Ser (GGT>AGT)

<400> SEQUENCE: 6
gttggagcta gtggcgtagg caaga                                            25

<210> SEQ ID NO 7
<211> LENGTH: 25
<212> TYPE: DNA
<213> ORGANISM: Homo sapiens
```

```
<220> FEATURE:
<221> NAME/KEY: misc_feature
<223> OTHER INFORMATION: Mutation Gly12Arg (GGT>CGT)

<400> SEQUENCE: 7
gttggagctc gtggcgtagg caaga                                              25

<210> SEQ ID NO 8
<211> LENGTH: 25
<212> TYPE: DNA
<213> ORGANISM: Homo sapiens
<220> FEATURE:
<221> NAME/KEY: misc_feature
<223> OTHER INFORMATION: Mutation: Gly12Cys (GGT>TGT)

<400> SEQUENCE: 8
gttggagctt gtggcgtagg caaga                                              25

<210> SEQ ID NO 9
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly12Asp (GGT>GAT)

<400> SEQUENCE: 9
gttggagctg atggcgtagg caaga                                              25

<210> SEQ ID NO 10
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly12Ala (GGT>GCT)

<400> SEQUENCE: 10
gttggagctg ctggcgtagg caaga                                              25

<210> SEQ ID NO 11
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly12Val (GGT>GTT)

<400> SEQUENCE: 11
gttggagctg ttggcgtagg caaga                                              25

<210> SEQ ID NO 12
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly13Ser (GGC>AGC)

<400> SEQUENCE: 12
gttggagctg gtagcgtagg caaga                                              25

<210> SEQ ID NO 13
<211> LENGTH: 25
<212> TYPE: DNA
<213> ORGANISM: Homo sapiens
<220> FEATURE:
```

```
<221> NAME/KEY: misc_feature
<223> OTHER INFORMATION: Mutation Gly13Arg (GGC>CGC)

<400> SEQUENCE: 13
gttggagctg gtcgcgtagg caaga                                    25

<210> SEQ ID NO 14
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly13Cys (GGC>TGC)

<400> SEQUENCE: 14
gttggagctg gttgcgtagg caaga                                    25

<210> SEQ ID NO 15
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly13Asp (GGC>GAC)

<400> SEQUENCE: 15
gttggagctg gtgacgtagg caaga                                    25

<210> SEQ ID NO 16
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly13Ala (GGC>GCC)

<400> SEQUENCE: 16
gttggagctg gtgccgtagg caaga                                    25

<210> SEQ ID NO 17
<211> LENGTH: 25
<212> TYPE: DNA
<213> ORGANISM: Homo sapiens
<220> FEATURE:
<221> NAME/KEY: misc_feature
<223> OTHER INFORMATION: Mutation Gly13Val (GGC>GTC)

<400> SEQUENCE: 17
gttggagctg gtgtcgtagg caaga                                    25

<210> SEQ ID NO 18
<211> LENGTH: 25
<212> TYPE: DNA
<213> ORGANISM: Homo sapiens
<220> FEATURE:
<221> NAME/KEY: misc_feature
<223> OTHER INFORMATION: KRAS Wild Type Antisense

<400> SEQUENCE: 18
tcttgcctac gccaccagct ccaac                                    25

<210> SEQ ID NO 19
<211> LENGTH: 25
<212> TYPE: DNA
<213> ORGANISM: Homo sapiens
<220> FEATURE:
<221> NAME/KEY: misc_feature
```

```
<223> OTHER INFORMATION: KRAS S1 Mutation Antisense

<400> SEQUENCE: 19
tcttgcctac gccactagct ccaac                                              25
```